US006444440B1

(12) United States Patent
Young et al.

(10) Patent No.: US 6,444,440 B1
(45) Date of Patent: Sep. 3, 2002

(54) VANILLOID RECEPTOR-2

(75) Inventors: Paul E. Young, Gaithersburg; Steven M. Ruben, Olney, both of MD (US)

(73) Assignee: Human Genome Sciences, Inc.

( * ) Notice: Subject to any disclaimer, the term of this patent is extended or adjusted under 35 U.S.C. 154(b) by 0 days.

(21) Appl. No.: 09/132,316

(22) Filed: Aug. 11, 1998

Related U.S. Application Data

(63) Continuation-in-part of application No. PCT/US98/04493, filed on Mar. 6, 1998.
(60) Provisional application No. 60/040,163, filed on Mar. 7, 1997.

(51) Int. Cl.$^7$ .......................... C12P 21/06; C07H 21/04; C07K 1/00; G01N 33/566
(52) U.S. Cl. .......................... 435/69.1; 435/6; 435/7.21; 435/252.3; 536/23.5; 536/23.4; 536/24.2; 536/24.31; 436/501; 514/2; 514/44; 530/350
(58) Field of Search .............................. 536/23.5, 23.4, 536/24.2, 24.31; 514/44, 2; 435/7.21, 6, 69.1, 252.3; 530/350; 436/501

(56) References Cited

U.S. PATENT DOCUMENTS

| 5,762,963 A | 6/1998 | Byas-Smith ................ 424/472 |
| 5,840,720 A | 11/1998 | Chen ........................ 544/230.5 |
| 5,939,578 A | 8/1999 | Chen ............................ 560/42 |
| 6,080,408 A | * | 6/2000 | Rovinski ................. 424/188.1 |

FOREIGN PATENT DOCUMENTS

| EP | 0 943 683 A1 | 9/1999 |
| EP | 0 953 638 A1 | 11/1999 |
| WO | WO 98/20867 A1 | 5/1998 |
| WO | WO 98/39448 A2 | 9/1998 |
| WO | WO 98/51290 A2 | 11/1998 |
| WO | WO 98/53825 A1 | 12/1998 |
| WO | WO 99/00115 A1 | 1/1999 |
| WO | WO 99/09140 | 2/1999 |
| WO | WO 99/37675 A1 | 7/1999 |
| WO | WO 99/37765 A1 | 7/1999 |
| WO | WO 99/46377 A2 | 9/1999 |

OTHER PUBLICATIONS

Caterinal et al., Nature 398:436–441, Apr. 1999.*
Everett et al., Nat. Gen. 17:411–422, Dec. 1997.*
Scott et al., Nat. Gen. 21:440–442, Apr. 1999.*
GenBank Accession No. H20025, Jul. 3, 1995.*
Adams, MD et al., Science 252(1651–1656)1991.*
Williams, DP et al., Nucleic Acids Res. 16:22(10453–10467)1988.*
Caterina et al., Nature 398:436–441, 1999.*
Bowie et al., Science 247:1306–1310, 1990.*
Wells Biochemistry 29:8509–8517, 1990.*
Ngo et al., The Protein Folding Problem and Tertiary Structure, 1994.*

Caterina, M.J. et al., "The capsaicin receptor: a heat–activated ion channel in the pain pathway," *Nature* 389:816–824 (Oct. 1997).
Hardie, R.C. and B. Minke, "Novel $Ca^{2+}$ channels underlying transduction in Drosophila photoreceptors: implications for phosphoinositide–mediated $Ca^{2+}$ mobilization," *Trends in Neurosci.* 16:371–376 (1993).
Montell, C. and G.M. Rubin, "Molecular Characterization of the Drosophila trp Locus: A Putative Integral Membrane Protein Required for Phototransduction," *Neuron* 2:1313–1323 (1989).
GenBank Accession No. N29128, Hillier, L. et al. (1996).
GenBank Accession No. AA741232, NCI–CGAP (Feb. 1998).
GenBank Accession No. W44731, Hillier, L. et al. (1996).
GenBank Accession No. N28029, Hillier, L. et al. (1995).
GenBank Accession No. N35179, Hillier, L. et al. (1996).
GenBank Accession No. AA768829, NCI–CGAP (Feb. 1998).
GenBank Accession No. H20025, Hillier, L. et al. (1995).
GenBank Accession No. W38665, Hillier, L. et al. (1996).
GenBank Accession No. AA281348, NCI–CGAP (Aug. 1997).
GenBank Accession No. W92895, Hillier, L. et al. (May 1997).
GenBank Accession No. AA461295, Hillier, L. et al. (Jun. 1997).
GenBank Accession No. AA815110, NCI–CGAP (Mar. 1998).
GenBank Accession No. H20101, Hillier, L. et al. (1995).
GenBank Accession No. N23395, Hillier, L. et al. (1995).
GenBank Accession No. AA236417, Hillier, L. et al. (Aug. 1997).
GenBank Accession No. AA459710, Hillier, L. et al. (Jun. 1997).
GenBank Accession No. H51393, Hillier, L. et al. (1995).
GenBank Accession No. H49128, Hillier, L. et al. (1995).
GenBank Accession No. N26729, Hillier, L. et al. (1995).

(List continued on next page.)

*Primary Examiner*—Yvonne Eyler
*Assistant Examiner*—Michael Brannock
(74) *Attorney, Agent, or Firm*—Sterne, Kessler, Goldstein & Fox P.L.L.C.

(57) ABSTRACT

The present invention relates to vanilloid receptor-2, a novel member of the vanilloid receptor family. The invention provides isolated nucleic acid molecules encoding human VR2 receptors. VR2 polypeptides are also provided, as are vectors, host cells and recombinant methods for producing the same. The invention further relates to screening methods for identifying agonists and antagonists of VR2 receptor activity. Also provided are diagnostic methods for detecting disease states related to the aberrant expression of VR2 receptors. Further provided are therapeutic methods for treating disease states including, but not limited to, chronic pain syndromes, congenital pain insensitivity, inflammation, ischemia, host defense dysfunction, immune surveillance dysfunction, arthritis, multiple sclerosis, autoimmunity, immune dysfunction, and allergy.

33 Claims, 9 Drawing Sheets

OTHER PUBLICATIONS

GenBank Accession No. N21167, Hillier, L. et al. (1995).
GenBank Accession No. H50404, Hillier, L. et al. (1995).
GenBank Accession No. AA304033, Adams, M.D. et al. (Apr. 1997).
GenBank Accession No. N34617, Hillier, L. et al. (1996).
GenBank Accession No. H50364, Hillier, L. et al. (1995).
GenBank Accession No. AA281349, NCI–CGAP (Aug. 1997).
GenBank Accession No. N24224, Hillier, L. et al. (1995).
GenBank Accession No. AA357145, Adams, M.D. et al. (Apr. 1997).
GenBank Accession No. W82502, Marra, M. et al. (1996).
GenBank Accession No. H99578, Hillier, L. et al. (1995).
GenBank Accession No. N21284, Hillier, L. et al. (1995).
GenBank Accession No. H51392, Hillier, L. et al. (1995).
GenBank Accession No. H21490, Hillier, L. et al. (1995).
GenBank Accession No. H49060, Hillier, L. et al. (1995).
GenBank Accession No. AA476107, Marra, M. et al. (Jun. 1997).
GenBank Accession No. H27879, Hillier, L. et al. (1995).
GenBank Accession No. H40615, Hillier, L. et al. (1995).
GenBank Accession No. AA814328, NCI–CGAP (Feb. 1998).
GenBank Accession No. T12251, Liew, C.C. et al. (1994).
GenBank Accession No. T71250, Hillier, L. et al. (1995).
GenBank Accession No. H99192, Hillier, L. et al. (1995).
GenBank Accession No. T90814, Hillier, L. et al. (1995).
GenBank Accession No. N24475, Hillier, L. et al. (1995).
GenBank Accession No. AA121981, Hillier, L. et al. (Dec. 1997).
GenBank Accession No. AA121980, Hillier, L. et al. (Dec. 1997).
GenBank Accession No. T12252, Liew, C.C. et al. (1994).
GenBank Accession No. AA015295, Marra, M. et al. (Jan. 1997).
GenBank Accession No. AA274980, Marra, M. et al. (Mar. 1997).
GenBank Accession No. AA139413, Marra, M. et al. (Feb. 1997).
GenBank Accession No. AA236416, Hillier, L. et al. (Aug. 1997).
GenBank Accession No. W92818, Hillier, L. et al. (May 1997).

* cited by examiner

SEQUENCE LISTING

<160> NUMBER OF SEQ ID NOS: 67

<210> SEQ ID NO 1
<211> LENGTH: 2805
<212> TYPE: DNA
<213> ORGANISM: Homo sapiens
<220> FEATURE:
<221> NAME/KEY: CDS
<222> LOCATION: (5)..(2674)

<400> SEQUENCE: 1

```
gcag atg gtc agt ctc tgg tgg cta gcc tgt cct gac agg gga gag tta      49
     Met Val Ser Leu Trp Trp Leu Ala Cys Pro Asp Arg Gly Glu Leu
```

-continued

```
       1               5              10              15
agc tcc cgt tct cca ccg tgc cgg ctg gcc agg tgg gct gag ggt gac    97
Ser Ser Arg Ser Pro Pro Cys Arg Leu Ala Arg Trp Ala Glu Gly Asp
                20              25              30 cga gag acc aga acc tgc ttg ctg gag ctt agt gct cag agc tgg gga    145
Arg Glu Thr Arg Thr Cys Leu Leu Glu Leu Ser Ala Gln Ser Trp Gly
            35              40              45 ggg agg ttc cgc cgc tcc tct gct gtc agc acc ggc agc ccc tcc cgg    193
Gly Arg Phe Arg Arg Ser Ser Ala Val Ser Thr Gly Ser Pro Ser Arg
        50              55              60 ctt cac ttc ctc ccg cag ccc ctg cta ctg aga agc tcc ggg atc cca    241
Leu His Phe Leu Pro Gln Pro Leu Leu Arg Ser Ser Gly Ile Pro
    65              70              75 gca gcc gcc acg ccc tgg cct cag cct gcg ggg ctc cag tca ggc caa    289
Ala Ala Ala Thr Pro Trp Pro Gln Pro Ala Gly Leu Gln Ser Gly Gln
80              85              90              95 cac cga cgc gca cgt ggg agg aag aca gga ccc ttg aca tct cca tct    337
His Arg Arg Ala Arg Gly Arg Lys Thr Gly Pro Leu Thr Ser Pro Ser
                100             105             110 gca cag agg tcc tgg ctg gac cga gct atg cct cct cct cct agg atg    385
Ala Gln Arg Ser Trp Leu Asp Arg Ala Met Pro Pro Pro Pro Arg Met
            115             120             125 acc tca ccc tcc agc tct cca gtt ttc agg ttg gag aca tta gat gga    433
Thr Ser Pro Ser Ser Ser Pro Val Phe Arg Leu Glu Thr Leu Asp Gly
        130             135             140 ggc caa gaa gat ggc tct gag gcg gac aga gga aag ctg gat ttt ggg    481
Gly Gln Glu Asp Gly Ser Glu Ala Asp Arg Gly Lys Leu Asp Phe Gly
145             150             155 agc ggg ctg cct ccc atg gag tca cag ttc cag ggc gag gac cgg aaa    529
Ser Gly Leu Pro Pro Met Glu Ser Gln Phe Gln Gly Glu Asp Arg Lys
160             165             170             175 ttc gcc cct cag ata aga gtc aac ctc aac tac cga aag gga aca ggt    577
Phe Ala Pro Gln Ile Arg Val Asn Leu Asn Tyr Arg Lys Gly Thr Gly
            180             185             190 gcc agt cag ccg gat cca aac cga ttt gac cga gat cgg ctc ttc aat    625
Ala Ser Gln Pro Asp Pro Asn Arg Phe Asp Arg Asp Arg Leu Phe Asn
        195             200             205 gcg gtc tcc cgg ggt gtc ccc gag gat ctg gct gga ctt cca gag tac    673
Ala Val Ser Arg Gly Val Pro Glu Asp Leu Ala Gly Leu Pro Glu Tyr
    210             215             220 ctg agc aag acc agc aag tac ctc acc gac tcg gaa tac aca gag ggc    721
Leu Ser Lys Thr Ser Lys Tyr Leu Thr Asp Ser Glu Tyr Thr Glu Gly
225             230             235 tcc aca ggt aag acg tgc ctg atg aag gct gtg ctg aac ctt aag gac    769
Ser Thr Gly Lys Thr Cys Leu Met Lys Ala Val Leu Asn Leu Lys Asp
240             245             250             255 ggg gtc aat gcc tgc att ctg cca ctg ctg cag atc gac cgg gac tct    817
Gly Val Asn Ala Cys Ile Leu Pro Leu Leu Gln Ile Asp Arg Asp Ser
            260             265             270 ggc aat cct cag ccc ctg gta aat gcc cag tgc aca gat gac tat tac    865
Gly Asn Pro Gln Pro Leu Val Asn Ala Gln Cys Thr Asp Asp Tyr Tyr
        275             280             285 cga ggc cac agc gct ctg cac atc gcc att gag aag agg agt ctg cag    913
Arg Gly His Ser Ala Leu His Ile Ala Ile Glu Lys Arg Ser Leu Gln
    290             295             300 tgt gtg aag ctc ctg gtg gag aat ggg gcc aat gtg cat gcc cgg gcc    961
Cys Val Lys Leu Leu Val Glu Asn Gly Ala Asn Val His Ala Arg Ala
305             310             315 tgc ggc cgc ttc ttc cag aag ggc caa ggg act tgc ttt tat ttc ggt   1009
```

```
                Cys Gly Arg Phe Phe Gln Lys Gly Gln Gly Thr Cys Phe Tyr Phe Gly
                320                 325                 330                 335 gag cta ccc ctc tct ttg gcc gct tgc acc aag cag tgg gat gtg gta              1057
Glu Leu Pro Leu Ser Leu Ala Ala Cys Thr Lys Gln Trp Asp Val Val
                    340                 345                 350 agc tac ctc ctg gag aac cca cac cag ccc gcc agc ctg cag gcc act              1105
Ser Tyr Leu Leu Glu Asn Pro His Gln Pro Ala Ser Leu Gln Ala Thr
                355                 360                 365 gac tcc cag ggc aac aca gtc ctg cat gcc cta gtg atg atc tcg gac              1153
Asp Ser Gln Gly Asn Thr Val Leu His Ala Leu Val Met Ile Ser Asp
            370                 375                 380 aac tca gct gag aac att gca ctg gtg acc agc atg tat gat ggg ctc              1201
Asn Ser Ala Glu Asn Ile Ala Leu Val Thr Ser Met Tyr Asp Gly Leu
        385                 390                 395 ctc caa gct ggg gcc cgc ctc tgc cct acc gtg cag ctt gag gac atc              1249
Leu Gln Ala Gly Ala Arg Leu Cys Pro Thr Val Gln Leu Glu Asp Ile
400                 405                 410                 415 cgc aac ctg cag gat ctc acg cct ctg aag ctg gcc gcc aag gag ggc              1297
Arg Asn Leu Gln Asp Leu Thr Pro Leu Lys Leu Ala Ala Lys Glu Gly
                    420                 425                 430 aag atc gag att ttc agg cac atc ctg cag cgg gag ttt tca gga ctg              1345
Lys Ile Glu Ile Phe Arg His Ile Leu Gln Arg Glu Phe Ser Gly Leu
                435                 440                 445 agc cac ctt tcc cga aag ttc acc gag tgg tgc tat ggg cct gtc cgg              1393
Ser His Leu Ser Arg Lys Phe Thr Glu Trp Cys Tyr Gly Pro Val Arg
            450                 455                 460 gtg tcg ctg tat gac ctg gct tct gtg gac agc tgt gag gag aac tca              1441
Val Ser Leu Tyr Asp Leu Ala Ser Val Asp Ser Cys Glu Glu Asn Ser
        465                 470                 475 gtg ctg gag atc att gcc ttt cat tgc aag agc ccg cac cga cac cga              1489
Val Leu Glu Ile Ile Ala Phe His Cys Lys Ser Pro His Arg His Arg
480                 485                 490                 495 atg gtc gtt ttg gag ccc ctg aac aaa ctg ctg cag gcg aaa tgg gat              1537
Met Val Val Leu Glu Pro Leu Asn Lys Leu Leu Gln Ala Lys Trp Asp
                    500                 505                 510 ctg ctc atc ccc aag ttc ttc tta aac ttc ctg tgt aat ctg atc tac              1585
Leu Leu Ile Pro Lys Phe Phe Leu Asn Phe Leu Cys Asn Leu Ile Tyr
                515                 520                 525 atg ttc atc ttc acc gct gtt gcc tac cat cag cct acc ctg aag aag              1633
Met Phe Ile Phe Thr Ala Val Ala Tyr His Gln Pro Thr Leu Lys Lys
            530                 535                 540 gcc gcc cct cac ctg aaa gcg gag gtt gga aac tcc atg ctg ctg acg              1681
Ala Ala Pro His Leu Lys Ala Glu Val Gly Asn Ser Met Leu Leu Thr
        545                 550                 555 ggc cac atc ctt atc ctg cta ggg ggg atc tac ctc ctc gtg ggc cag              1729
Gly His Ile Leu Ile Leu Leu Gly Gly Ile Tyr Leu Leu Val Gly Gln
560                 565                 570                 575 ctg tgg tac ttc tgg cgg cgc cac gtg ttc atc tgg atc tcg ttc ata              1777
Leu Trp Tyr Phe Trp Arg Arg His Val Phe Ile Trp Ile Ser Phe Ile
                    580                 585                 590 gac agc tac ttt gaa atc ctc ttc ctg ttc cag gcc ctg ctc aca gtg              1825
Asp Ser Tyr Phe Glu Ile Leu Phe Leu Phe Gln Ala Leu Leu Thr Val
                595                 600                 605 gtg tcc cag gtg ctg tgt ttc ctg gcc atc gag tgg tac ctg ccc ctg              1873
Val Ser Gln Val Leu Cys Phe Leu Ala Ile Glu Trp Tyr Leu Pro Leu
            610                 615                 620 ctt gtg tct gcg ctg gtg ctg ggc tgg ctg aac ctg ctt tac tat aca              1921
Leu Val Ser Ala Leu Val Leu Gly Trp Leu Asn Leu Leu Tyr Tyr Thr
        625                 630                 635
```

```
cgt ggc ttc cag cac aca ggc atc tac agt gtc atg atc cag aag gtc    1969
Arg Gly Phe Gln His Thr Gly Ile Tyr Ser Val Met Ile Gln Lys Val
640             645                 650                 655 atc ctg cgg gac ctg ctg cgc ttc ctt ctg atc tac tta gtc ttc ctt    2017
Ile Leu Arg Asp Leu Leu Arg Phe Leu Leu Ile Tyr Leu Val Phe Leu
                660                 665                 670 ttc ggc ttc gct gta gcc ctg gtg agc ctg agc cag gag gct tgg cgc    2065
Phe Gly Phe Ala Val Ala Leu Val Ser Leu Ser Gln Glu Ala Trp Arg
            675                 680                 685 ccc gaa gct cct aca ggc ccc aat gcc aca gag tca gtg cag ccc atg    2113
Pro Glu Ala Pro Thr Gly Pro Asn Ala Thr Glu Ser Val Gln Pro Met
        690                 695                 700 gag gga cag gag gac gag ggc aac ggg gcc cag tac agg ggt atc ctg    2161
Glu Gly Gln Glu Asp Glu Gly Asn Gly Ala Gln Tyr Arg Gly Ile Leu
705                 710                 715 gaa gcc tcc ttg gag ctc ttc aaa ttc acc atc ggc atg ggc gag ctg    2209
Glu Ala Ser Leu Glu Leu Phe Lys Phe Thr Ile Gly Met Gly Glu Leu
720                 725                 730                 735 gcc ttc cag gag cag ctg cac ttc cgc ggc atg gtg ctg ctg ctg        2257
Ala Phe Gln Glu Gln Leu His Phe Arg Gly Met Val Leu Leu Leu Leu
                740                 745                 750 ctg gcc tac gtg ctg ctc acc tac atc ctg ctc aac atg ctc atc        2305
Leu Ala Tyr Val Leu Leu Thr Tyr Ile Leu Leu Leu Asn Met Leu Ile
            755                 760                 765 gcc ctc atg agc gag acc gtc aac agt gtc gcc act gac agc tgg agc    2353
Ala Leu Met Ser Glu Thr Val Asn Ser Val Ala Thr Asp Ser Trp Ser
        770                 775                 780 atc tgg aag ctg cag aaa gcc atc tct gtc ctg gag atg gag aat ggc    2401
Ile Trp Lys Leu Gln Lys Ala Ile Ser Val Leu Glu Met Glu Asn Gly
785                 790                 795 tat tgg tgg tgc agg aag aag cag cgg gca ggt gtg atg ctg acc gtt    2449
Tyr Trp Trp Cys Arg Lys Lys Gln Arg Ala Gly Val Met Leu Thr Val
800                 805                 810                 815 ggc act aag cca gat ggc agc ccc gat gag cgc tgg tgc ttc agg gtg    2497
Gly Thr Lys Pro Asp Gly Ser Pro Asp Glu Arg Trp Cys Phe Arg Val
                820                 825                 830 gag gag gtg aac tgg gct tca tgg gag cag acg ctg cct acg ctg tgt    2545
Glu Glu Val Asn Trp Ala Ser Trp Glu Gln Thr Leu Pro Thr Leu Cys
            835                 840                 845 gag gac ccg tca ggg gca ggt gtc cct cga act ctc gag aac cct gtc    2593
Glu Asp Pro Ser Gly Ala Gly Val Pro Arg Thr Leu Glu Asn Pro Val
        850                 855                 860 ctg gct tcc cct ccc aag gag gat gag gat ggt gcc tct gag gaa aac    2641
Leu Ala Ser Pro Pro Lys Glu Asp Glu Asp Gly Ala Ser Glu Glu Asn
865                 870                 875 tat gtg ccc gtc cag ctc ctc cag tcc aac tga tggcccagat gcagcaggag  2694
Tyr Val Pro Val Gln Leu Leu Gln Ser Asn
880                 885                 890 gccagaggac agagcagagg atctttccaa ccacatctgc tggctctggg gtcccagtga  2754
attctggtgg caaatatata ttttcactaa ctcaaaaaaa aaaaaaaaaa a           2805

<210> SEQ ID NO 2
<211> LENGTH: 889
<212> TYPE: PRT
<213> ORGANISM: Homo sapiens

<400> SEQUENCE: 2

Met Val Ser Leu Trp Trp Leu Ala Cys Pro Asp Arg Gly Glu Leu Ser
1               5                   10                  15
```

-continued

```
Ser Arg Ser Pro Pro Cys Arg Leu Ala Arg Trp Ala Glu Gly Asp Arg
         20                  25                  30
Glu Thr Arg Thr Cys Leu Leu Glu Leu Ser Ala Gln Ser Trp Gly Gly
         35                  40                  45
Arg Phe Arg Arg Ser Ser Ala Val Ser Thr Gly Ser Pro Ser Arg Leu
 50                  55                  60
His Phe Leu Pro Gln Pro Leu Leu Arg Ser Ser Gly Ile Pro Ala
 65                  70                  75                  80
Ala Ala Thr Pro Trp Pro Gln Pro Ala Gly Leu Gln Ser Gly Gln His
                 85                  90                  95
Arg Arg Ala Arg Gly Arg Lys Thr Gly Pro Leu Thr Ser Pro Ser Ala
             100                 105                 110
Gln Arg Ser Trp Leu Asp Arg Ala Met Pro Pro Pro Arg Met Thr
         115                 120                 125
Ser Pro Ser Ser Ser Pro Val Phe Arg Leu Glu Thr Leu Asp Gly Gly
         130                 135                 140
Gln Glu Asp Gly Ser Glu Ala Asp Arg Gly Lys Leu Asp Phe Gly Ser
145                 150                 155                 160
Gly Leu Pro Pro Met Glu Ser Gln Phe Gln Gly Glu Asp Arg Lys Phe
                 165                 170                 175
Ala Pro Gln Ile Arg Val Asn Leu Asn Tyr Arg Lys Gly Thr Gly Ala
             180                 185                 190
Ser Gln Pro Asp Pro Asn Arg Phe Asp Arg Asp Arg Leu Phe Asn Ala
         195                 200                 205
Val Ser Arg Gly Val Pro Glu Asp Leu Ala Gly Leu Pro Glu Tyr Leu
210                 215                 220
Ser Lys Thr Ser Lys Tyr Leu Thr Asp Ser Glu Tyr Thr Glu Gly Ser
225                 230                 235                 240
Thr Gly Lys Thr Cys Leu Met Lys Ala Val Leu Asn Leu Lys Asp Gly
                 245                 250                 255
Val Asn Ala Cys Ile Leu Pro Leu Leu Gln Ile Asp Arg Asp Ser Gly
             260                 265                 270
Asn Pro Gln Pro Leu Val Asn Ala Gln Cys Thr Asp Asp Tyr Tyr Arg
         275                 280                 285
Gly His Ser Ala Leu His Ile Ala Ile Glu Lys Arg Ser Leu Gln Cys
         290                 295                 300
Val Lys Leu Leu Val Glu Asn Gly Ala Asn Val His Ala Arg Ala Cys
305                 310                 315                 320
Gly Arg Phe Phe Gln Lys Gly Gln Gly Thr Cys Phe Tyr Phe Gly Glu
                 325                 330                 335
Leu Pro Leu Ser Leu Ala Ala Cys Thr Lys Gln Trp Asp Val Val Ser
             340                 345                 350
Tyr Leu Leu Glu Asn Pro His Gln Pro Ala Ser Leu Gln Ala Thr Asp
         355                 360                 365
Ser Gln Gly Asn Thr Val Leu His Ala Leu Val Met Ile Ser Asp Asn
370                 375                 380
Ser Ala Glu Asn Ile Ala Leu Val Thr Ser Met Tyr Asp Gly Leu Leu
385                 390                 395                 400
Gln Ala Gly Ala Arg Leu Cys Pro Thr Val Gln Leu Glu Asp Ile Arg
                 405                 410                 415
Asn Leu Gln Asp Leu Thr Pro Leu Lys Leu Ala Ala Lys Glu Gly Lys
             420                 425                 430
Ile Glu Ile Phe Arg His Ile Leu Gln Arg Glu Phe Ser Gly Leu Ser
```

-continued

```
            435                 440                 445
His Leu Ser Arg Lys Phe Thr Glu Trp Cys Tyr Gly Pro Val Arg Val
    450                 455                 460
Ser Leu Tyr Asp Leu Ala Ser Val Asp Ser Cys Glu Asn Ser Val
465                 470                 475                 480
Leu Glu Ile Ile Ala Phe His Cys Lys Ser Pro His Arg His Arg Met
                485                 490                 495
Val Val Leu Glu Pro Leu Asn Lys Leu Leu Gln Ala Lys Trp Asp Leu
            500                 505                 510
Leu Ile Pro Lys Phe Phe Leu Asn Phe Leu Cys Asn Leu Ile Tyr Met
            515                 520                 525
Phe Ile Phe Thr Ala Val Ala Tyr His Gln Pro Thr Leu Lys Lys Ala
    530                 535                 540
Ala Pro His Leu Lys Ala Glu Val Gly Asn Ser Met Leu Leu Thr Gly
545                 550                 555                 560
His Ile Leu Ile Leu Leu Gly Gly Ile Tyr Leu Leu Val Gly Gln Leu
                565                 570                 575
Trp Tyr Phe Trp Arg Arg His Val Phe Ile Trp Ile Ser Phe Ile Asp
            580                 585                 590
Ser Tyr Phe Glu Ile Leu Phe Leu Phe Gln Ala Leu Leu Thr Val Val
    595                 600                 605
Ser Gln Val Leu Cys Phe Leu Ala Ile Glu Trp Tyr Leu Pro Leu Leu
610                 615                 620
Val Ser Ala Leu Val Leu Gly Trp Leu Asn Leu Leu Tyr Tyr Thr Arg
625                 630                 635                 640
Gly Phe Gln His Thr Gly Ile Tyr Ser Val Met Ile Gln Lys Val Ile
                645                 650                 655
Leu Arg Asp Leu Leu Arg Phe Leu Leu Ile Tyr Leu Val Phe Leu Phe
            660                 665                 670
Gly Phe Ala Val Ala Leu Val Ser Leu Ser Gln Glu Ala Trp Arg Pro
    675                 680                 685
Glu Ala Pro Thr Gly Pro Asn Ala Thr Glu Ser Val Gln Pro Met Glu
    690                 695                 700
Gly Gln Glu Asp Glu Gly Asn Gly Ala Gln Tyr Arg Gly Ile Leu Glu
705                 710                 715                 720
Ala Ser Leu Glu Leu Phe Lys Phe Thr Ile Gly Met Gly Glu Leu Ala
                725                 730                 735
Phe Gln Glu Gln Leu His Phe Arg Gly Met Val Leu Leu Leu Leu Leu
            740                 745                 750
Ala Tyr Val Leu Leu Thr Tyr Ile Leu Leu Leu Asn Met Leu Ile Ala
            755                 760                 765
Leu Met Ser Glu Thr Val Asn Ser Val Ala Thr Asp Ser Trp Ser Ile
    770                 775                 780
Trp Lys Leu Gln Lys Ala Ile Ser Val Leu Glu Met Glu Asn Gly Tyr
785                 790                 795                 800
Trp Trp Cys Arg Lys Lys Gln Arg Ala Gly Val Met Leu Thr Val Gly
                805                 810                 815
Thr Lys Pro Asp Gly Ser Pro Asp Glu Arg Trp Cys Phe Arg Val Glu
            820                 825                 830
Glu Val Asn Trp Ala Ser Trp Glu Gln Thr Leu Pro Thr Leu Cys Glu
            835                 840                 845
Asp Pro Ser Gly Ala Gly Val Pro Arg Thr Leu Glu Asn Pro Val Leu
    850                 855                 860
```

-continued

```
Ala Ser Pro Pro Lys Glu Asp Glu Asp Gly Ala Ser Glu Glu Asn Tyr
865                 870                 875                 880

Val Pro Val Gln Leu Leu Gln Ser Asn
                885

<210> SEQ ID NO 3
<211> LENGTH: 838
<212> TYPE: PRT
<213> ORGANISM: Rattus norvegicus

<400> SEQUENCE: 3

Met Glu Gln Arg Ala Ser Leu Asp Ser Glu Glu Ser Glu Ser Pro Pro
  1               5                  10                  15

Gln Glu Asn Ser Cys Leu Asp Pro Pro Asp Arg Asp Pro Asn Cys Lys
                 20                  25                  30

Pro Pro Pro Val Lys Pro His Ile Phe Thr Thr Arg Ser Arg Thr Arg
             35                  40                  45

Leu Phe Gly Lys Gly Asp Ser Glu Glu Ala Ser Pro Leu Asp Cys Pro
 50                  55                  60

Tyr Glu Glu Gly Gly Leu Ala Ser Cys Pro Ile Ile Thr Val Ser Ser
 65                  70                  75                  80

Val Leu Thr Ile Gln Arg Pro Gly Asp Gly Pro Ala Ser Val Arg Pro
                 85                  90                  95

Ser Ser Gln Asp Ser Val Ser Ala Gly Glu Lys Pro Pro Arg Leu Tyr
                100                 105                 110

Asp Arg Arg Ser Ile Phe Asp Ala Val Ala Gln Ser Asn Cys Gln Glu
             115                 120                 125

Leu Glu Ser Leu Leu Pro Phe Leu Gln Arg Ser Lys Lys Arg Leu Thr
130                 135                 140

Asp Ser Glu Phe Lys Asp Pro Glu Thr Gly Lys Thr Cys Leu Leu Lys
145                 150                 155                 160

Ala Met Leu Asn Leu His Asn Gly Gln Asn Asp Thr Ile Ala Leu Leu
                165                 170                 175

Leu Asp Val Ala Arg Lys Thr Asp Ser Leu Lys Gln Phe Val Asn Ala
                180                 185                 190

Ser Tyr Thr Asp Ser Tyr Tyr Lys Gly Gln Thr Ala Leu His Ile Ala
             195                 200                 205

Ile Glu Arg Arg Asn Met Thr Leu Val Thr Leu Leu Val Glu Asn Gly
210                 215                 220

Ala Asp Val Gln Ala Ala Ala Asn Gly Asp Phe Phe Lys Lys Thr Lys
225                 230                 235                 240

Gly Arg Pro Gly Phe Tyr Phe Gly Glu Leu Pro Leu Ser Leu Ala Ala
                245                 250                 255

Cys Thr Asn Gln Leu Ala Ile Val Lys Phe Leu Leu Gln Asn Ser Trp
                260                 265                 270

Gln Pro Ala Asp Ile Ser Ala Arg Asp Ser Val Gly Asn Thr Val Leu
             275                 280                 285

His Ala Leu Val Glu Val Ala Asp Asn Thr Val Asp Asn Thr Lys Phe
290                 295                 300

Val Thr Ser Met Tyr Asn Glu Ile Leu Ile Leu Gly Ala Lys Leu His
305                 310                 315                 320

Pro Thr Leu Lys Leu Glu Glu Ile Thr Asn Arg Lys Gly Leu Thr Pro
                325                 330                 335

Leu Ala Leu Ala Ala Ser Ser Gly Lys Ile Gly Val Leu Ala Tyr Ile
```

-continued

```
            340                 345                 350
Leu Gln Arg Glu Ile His Glu Pro Glu Cys Arg His Leu Ser Arg Lys
            355                 360                 365
Phe Thr Glu Trp Ala Tyr Gly Pro Val His Ser Ser Leu Tyr Asp Leu
            370                 375                 380
Ser Cys Ile Asp Thr Cys Glu Lys Asn Ser Val Leu Glu Val Ile Ala
385                 390                 395                 400
Tyr Ser Ser Ser Glu Thr Pro Asn Arg His Asp Met Leu Leu Val Glu
                405                 410                 415
Pro Leu Asn Arg Leu Leu Gln Asp Lys Trp Asp Arg Phe Val Lys Arg
                420                 425                 430
Ile Phe Tyr Phe Asn Phe Phe Val Tyr Cys Leu Tyr Met Ile Ile Phe
            435                 440                 445
Thr Ala Ala Ala Tyr Tyr Arg Pro Val Glu Gly Leu Pro Pro Tyr Lys
            450                 455                 460
Leu Lys Asn Thr Val Gly Asp Tyr Phe Arg Val Thr Gly Glu Ile Leu
465                 470                 475                 480
Ser Val Ser Gly Gly Val Tyr Phe Phe Arg Gly Ile Gln Tyr Phe
                485                 490                 495
Leu Gln Arg Arg Pro Ser Leu Lys Ser Leu Phe Val Asp Ser Tyr Ser
                500                 505                 510
Glu Ile Leu Phe Phe Val Gln Ser Leu Phe Met Leu Val Ser Val Val
            515                 520                 525
Leu Tyr Phe Ser Gln Arg Lys Glu Tyr Val Ala Ser Met Val Phe Ser
            530                 535                 540
Leu Ala Met Gly Trp Thr Asn Met Leu Tyr Tyr Thr Arg Gly Phe Gln
545                 550                 555                 560
Gln Met Gly Ile Tyr Ala Val Met Ile Glu Lys Met Ile Leu Arg Asp
                565                 570                 575
Leu Cys Arg Phe Met Phe Val Tyr Leu Val Phe Leu Phe Gly Phe Ser
                580                 585                 590
Thr Ala Val Val Thr Leu Ile Glu Asp Gly Lys Asn Asn Ser Leu Pro
            595                 600                 605
Met Glu Ser Thr Pro His Lys Cys Arg Gly Ser Ala Cys Lys Pro Gly
            610                 615                 620
Asn Ser Tyr Asn Ser Leu Tyr Ser Thr Cys Leu Glu Leu Phe Lys Phe
625                 630                 635                 640
Thr Ile Gly Met Gly Asp Leu Glu Phe Thr Glu Asn Tyr Asp Phe Lys
                645                 650                 655
Ala Val Phe Ile Ile Leu Leu Leu Ala Tyr Val Ile Leu Thr Tyr Ile
                660                 665                 670
Leu Leu Leu Asn Met Leu Ile Ala Leu Met Gly Glu Thr Val Asn Lys
            675                 680                 685
Ile Ala Gln Glu Ser Lys Asn Ile Trp Lys Leu Gln Arg Ala Ile Thr
            690                 695                 700
Ile Leu Asp Thr Glu Lys Ser Phe Leu Lys Cys Met Arg Lys Ala Phe
705                 710                 715                 720
Arg Ser Gly Lys Leu Leu Gln Val Gly Phe Thr Pro Asp Gly Lys Asp
                725                 730                 735
Asp Tyr Arg Trp Cys Phe Arg Val Asp Glu Val Asn Trp Thr Thr Trp
            740                 745                 750
Asn Thr Asn Val Gly Ile Ile Asn Glu Asp Pro Gly Asn Cys Glu Gly
            755                 760                 765
```

```
            Val Lys Arg Thr Leu Ser Phe Ser Leu Arg Ser Gly Arg Val Ser Gly
                770                 775                 780

Arg Asn Trp Lys Asn Phe Ala Leu Val Pro Leu Leu Arg Asp Ala Ser
            785                 790                 795                 800

Thr Arg Asp Arg His Ala Thr Gln Gln Glu Glu Val Gln Leu Lys His
                                805                 810                 815

Tyr Thr Gly Ser Leu Lys Pro Glu Asp Ala Glu Val Phe Lys Asp Ser
                        820                 825                 830

Met Val Pro Gly Glu Lys
                    835

<210> SEQ ID NO 4
<211> LENGTH: 44
<212> TYPE: DNA
<213> ORGANISM: Homo sapiens

<400> SEQUENCE: 4
gcagcacata tggtcagtct ctggtggcta gcctgtcctg acag                    44

<210> SEQ ID NO 5
<211> LENGTH: 46
<212> TYPE: DNA
<213> ORGANISM: Homo sapiens

<400> SEQUENCE: 5
gcagcaggta cctcagttgg actggaggag ctggacgggc acatag                  46

<210> SEQ ID NO 6
<211> LENGTH: 53
<212> TYPE: DNA
<213> ORGANISM: Homo sapiens

<400> SEQUENCE: 6
gcagcaagat ctgccatcat ggtcagtctc tggtggctag cctgtcctga cag          53

<210> SEQ ID NO 7
<211> LENGTH: 46
<212> TYPE: DNA
<213> ORGANISM: Homo sapiens

<400> SEQUENCE: 7
gcagcatcta gatcagttgg actggaggag ctggacgggc acatag                  46

<210> SEQ ID NO 8
<211> LENGTH: 733
<212> TYPE: DNA
<213> ORGANISM: Homo sapiens

<400> SEQUENCE: 8
gggatccgga gcccaaatct tctgacaaaa ctcacacatg cccaccgtgc ccagcacctg    60
aattcgaggg tgcaccgtca gtcttcctct tccccccaaa acccaaggac accctcatga   120
tctcccggac tcctgaggtc acatgcgtgg tggtggacgt aagccacgaa gaccctgagg   180
tcaagttcaa ctggtacgtg gacggcgtgg aggtgcataa tgccaagaca aagccgcggg   240
aggagcagta caacagcacg taccgtgtgg tcagcgtcct caccgtcctg caccaggact   300
ggctgaatgg caaggagtac aagtgcaagg tctccaacaa agccctccca acccccatcg   360
agaaaaccat ctccaaagcc aaagggcagc ccgagaacca caggtgtac accctgcccc   420 catcccggga tgagctgacc aagaaccagg tcagcctgac ctgcctggtc aaaggcttct   480
```

-continued

| | |
|---|---|
| atccaagcga catcgccgtg gagtgggaga gcaatgggca gccggagaac aactacaaga | 540 |
| ccacgcctcc cgtgctggac tccgacggct ccttcttcct ctacagcaag ctcaccgtgg | 600 |
| acaagagcag gtggcagcag gggaacgtct tctcatgctc cgtgatgcat gaggctctgc | 660 |
| acaaccacta cacgcagaag agcctctccc tgtctccggg taaatgagtg cgacggccgc | 720 |
| gactctagag gat | 733 |

```
<210> SEQ ID NO 9
<211> LENGTH: 468
<212> TYPE: DNA
<213> ORGANISM: Homo sapiens
<220> FEATURE:
<221> NAME/KEY: Unsure
<222> LOCATION: 23
<223> OTHER INFORMATION: May be any nucleotide
<220> FEATURE:
<221> NAME/KEY: Unsure
<222> LOCATION: 309
<223> OTHER INFORMATION: May be any nucleotide
<220> FEATURE:
<221> NAME/KEY: Unsure
<222> LOCATION: 374
<223> OTHER INFORMATION: May be any nucleotide
<220> FEATURE:
<221> NAME/KEY: Unsure
<222> LOCATION: 378
<223> OTHER INFORMATION: May be any nucleotide
<220> FEATURE:
<221> NAME/KEY: Unsure
<222> LOCATION: 389
<223> OTHER INFORMATION: May be any nucleotide
<220> FEATURE:
<221> NAME/KEY: Unsure
<222> LOCATION: 423
<223> OTHER INFORMATION: May be any nucleotide
<220> FEATURE:
<221> NAME/KEY: Unsure
<222> LOCATION: 434
<223> OTHER INFORMATION: May be any nucleotide
<220> FEATURE:
<221> NAME/KEY: Unsure
<222> LOCATION: 443
<223> OTHER INFORMATION: May be any nucleotide
<220> FEATURE:
<221> NAME/KEY: Unsure
<222> LOCATION: 445
<223> OTHER INFORMATION: May be any nucleotide
<220> FEATURE:
<221> NAME/KEY: Unsure
<222> LOCATION: 464
<223> OTHER INFORMATION: May be any nucleotide

<400> SEQUENCE: 9
```

| | |
|---|---|
| aattccgtga aaatatatat ttnccaccag aattcactgg daccccagag ccagcagatg | 60 |
| tggttggaaa gatcctctgc tctgtcctct ggcctcctgc tgcatctggg ccatcagttg | 120 |
| gactggagga gctggacggg cacatagttt tcctcagagg caccatcctc atcctccttg | 180 |
| ggagggaag ccaggacagg gttctcgaga gttcgaggga cacctgcccc tgacgggtcc | 240 |
| tcacacagcg taggcagcgt ctgctcccat gaagcccagt tcaactcctc caccctgaag | 300 |
| caccagcgnt tcatcggggc tgccatcttg gcttagtgcc aaggttcagc atcaaaactg | 360 |
| cccgttgttt tttnctgnaa caccatagnc attttccatt ttcaggacag agatggtttt | 420 |
| tgnagttcca atgnttcagt ttnantgggg aaattttgac ggtntggt | 468 |

```
<210> SEQ ID NO 10
<211> LENGTH: 319
<212> TYPE: DNA
```

```
<213> ORGANISM: Homo sapiens
<220> FEATURE:
<221> NAME/KEY: Unsure
<222> LOCATION: 8
<223> OTHER INFORMATION: May be any nucleotide
<220> FEATURE:
<221> NAME/KEY: Unsure
<222> LOCATION: 57
<223> OTHER INFORMATION: May be any nucleotide
<220> FEATURE:
<221> NAME/KEY: Unsure
<222> LOCATION: 162
<223> OTHER INFORMATION: May be any nucleotide
<220> FEATURE:
<221> NAME/KEY: Unsure
<222> LOCATION: 167
<223> OTHER INFORMATION: May be any nucleotide
<220> FEATURE:
<221> NAME/KEY: Unsure
<222> LOCATION: 285
<223> OTHER INFORMATION: May be any nucleotide

<400> SEQUENCE: 10
ttccaggngc agctgcactt ccgcggcatg gtgctgctgc tgctgctggc ctacgtnctg      60
ctcacctaca tcctgctgct caacatgctc atcgccctca tgagcgagac cgtcaacagt    120
gtcgccactg acagctggag catctggaag ctgcagaaag cnatctntgt cctggagatg    180
gagaatggct attggtggtg caggaagaag cagcgggcag gtgtgatgct gaccgttggc    240
actaagccag atggcagccc cgatgagcgc tggtgcttca gggtngagga ggtgaactgg    300
gcttcatggg gagcagacg                                                 319

<210> SEQ ID NO 11
<211> LENGTH: 299
<212> TYPE: DNA
<213> ORGANISM: Homo sapiens
<220> FEATURE:
<221> NAME/KEY: Unsure
<222> LOCATION: 83
<223> OTHER INFORMATION: May be any nucleotide
<220> FEATURE:
<221> NAME/KEY: Unsure
<222> LOCATION: 95
<223> OTHER INFORMATION: May be any nucleotide

<400> SEQUENCE: 11
ttcaggactg agccacccttt cccgaaagtt caccgagtgg tgctatgggc ctgtccgggt     60
gtcgctgtat gacctggctt ctntggacag ctgtnaggag aactcagtgc tggagatcat    120
tgcctttcat tgcaagagcc cgcaccgaca ccgaatggtc gttttggagc ccctgaacaa    180
actgctgcag gcggaaatgg gatctgctca tccccaagtt cttcttaaac ttcctgtgta    240
atctgatcta catgttcatc ttcaacgctg ttgcctacca tcagcctacc ctgaagaag     299

<210> SEQ ID NO 12
<211> LENGTH: 466
<212> TYPE: DNA
<213> ORGANISM: Homo sapiens
<220> FEATURE:
<221> NAME/KEY: Unsure
<222> LOCATION: 297
<223> OTHER INFORMATION: May be any nucleotide
<220> FEATURE:
<221> NAME/KEY: Unsure
<222> LOCATION: 322
<223> OTHER INFORMATION: May be any nucleotide
<220> FEATURE:
<221> NAME/KEY: Unsure
<222> LOCATION: 387
<223> OTHER INFORMATION: May be any nucleotide
```

```
<220> FEATURE:
<221> NAME/KEY: Unsure
<222> LOCATION: 406
<223> OTHER INFORMATION: May be any nucleotide
<220> FEATURE:
<221> NAME/KEY: Unsure
<222> LOCATION: 427
<223> OTHER INFORMATION: May be any nucleotide
<220> FEATURE:
<221> NAME/KEY: Unsure
<222> LOCATION: 439
<223> OTHER INFORMATION: May be any nucleotide
<220> FEATURE:
<221> NAME/KEY: Unsure
<222> LOCATION: 461
<223> OTHER INFORMATION: May be any nucleotide

<400> SEQUENCE: 12
aattcggcag aggccacgcc ctggcctcag cctgcggggc tccagtcagg ccaacaccga      60
cgcgcatggg aggaagacag gacccttgac atctccatct gcacagaggt cctggctgga     120
ccagacagcc tcctcctcct aggatgacct caccctccag ctctccagtt ttcaggttgg     180
agacattaga tggaggccaa gaagatggct ctgaggcgga cagaggaaag ctggattttg     240
ggagcgggct gcctcccatg gagttcacag ttccagggcg aggaccggaa atttggncct     300
tcagataaga gtcaacctca ataccgaaa gggaacaggt gccattcagc cggattccaa      360
accgtttttg accggatcgg tttttnaat ggggttttcc ggggtnttcc cgaggatttg      420
gttgganttc caggtactna gcaagaccag aatacttacg nttggt                    466

<210> SEQ ID NO 13
<211> LENGTH: 497
<212> TYPE: DNA
<213> ORGANISM: Homo sapiens
<220> FEATURE:
<221> NAME/KEY: Unsure
<222> LOCATION: 112
<223> OTHER INFORMATION: May be any nucleotide
<220> FEATURE:
<221> NAME/KEY: Unsure
<222> LOCATION: 129
<223> OTHER INFORMATION: May be any nucleotide
<220> FEATURE:
<221> NAME/KEY: Unsure
<222> LOCATION: 208
<223> OTHER INFORMATION: May be any nucleotide
<220> FEATURE:
<221> NAME/KEY: Unsure
<222> LOCATION: 228
<223> OTHER INFORMATION: May be any nucleotide
<220> FEATURE:
<221> NAME/KEY: Unsure
<222> LOCATION: 298
<223> OTHER INFORMATION: May be any nucleotide
<220> FEATURE:
<221> NAME/KEY: Unsure
<222> LOCATION: 309
<223> OTHER INFORMATION: May be any nucleotide
<220> FEATURE:
<221> NAME/KEY: Unsure
<222> LOCATION: 313
<223> OTHER INFORMATION: May be any nucleotide
<220> FEATURE:
<221> NAME/KEY: Unsure
<222> LOCATION: 324
<223> OTHER INFORMATION: May be any nucleotide
<220> FEATURE:
<221> NAME/KEY: Unsure
<222> LOCATION: 333
<223> OTHER INFORMATION: May be any nucleotide
<220> FEATURE:
<221> NAME/KEY: Unsure
<222> LOCATION: 353
```

```
<223> OTHER INFORMATION: May be any nucleotide
<220> FEATURE:
<221> NAME/KEY: Unsure
<222> LOCATION: 372
<223> OTHER INFORMATION: May be any nucleotide
<220> FEATURE:
<221> NAME/KEY: Unsure
<222> LOCATION: 385
<223> OTHER INFORMATION: May be any nucleotide
<220> FEATURE:
<221> NAME/KEY: Unsure
<222> LOCATION: 390
<223> OTHER INFORMATION: May be any nucleotide
<220> FEATURE:
<221> NAME/KEY: Unsure
<222> LOCATION: 396
<223> OTHER INFORMATION: May be any nucleotide
<220> FEATURE:
<221> NAME/KEY: Unsure
<222> LOCATION: 399
<223> OTHER INFORMATION: May be any nucleotide
<220> FEATURE:
<221> NAME/KEY: Unsure
<222> LOCATION: 401
<223> OTHER INFORMATION: May be any nucleotide
<220> FEATURE:
<221> NAME/KEY: Unsure
<222> LOCATION: 407
<223> OTHER INFORMATION: May be any nucleotide
<220> FEATURE:
<221> NAME/KEY: Unsure
<222> LOCATION: 424
<223> OTHER INFORMATION: May be any nucleotide
<220> FEATURE:
<221> NAME/KEY: Unsure
<222> LOCATION: 432
<223> OTHER INFORMATION: May be any nucleotide
<220> FEATURE:
<221> NAME/KEY: Unsure
<222> LOCATION: 440
<223> OTHER INFORMATION: May be any nucleotide
<220> FEATURE:
<221> NAME/KEY: Unsure
<222> LOCATION: 444
<223> OTHER INFORMATION: May be any nucleotide
<220> FEATURE:
<221> NAME/KEY: Unsure
<222> LOCATION: 466
<223> OTHER INFORMATION: May be any nucleotide
<220> FEATURE:
<221> NAME/KEY: Unsure
<222> LOCATION: 481
<223> OTHER INFORMATION: May be any nucleotide
<220> FEATURE:
<221> NAME/KEY: Unsure
<222> LOCATION: 487
<223> OTHER INFORMATION: May be any nucleotide
<220> FEATURE:
<221> NAME/KEY: Unsure
<222> LOCATION: 492
<223> OTHER INFORMATION: May be any nucleotide
<220> FEATURE:
<221> NAME/KEY: Unsure
<222> LOCATION: 497
<223> OTHER INFORMATION: May be any nucleotide

<400> SEQUENCE: 13
aattcggcac gagatcctgc gggacctgct gcgcttcctt ctgatctact tagtcttcct      60
tttcggcttc gctgtagccc tggtgagcct gagccaggag gcttggcgcc cnggaagctc     120
ctacaggcnc cattgccaca gagtcagtgc agcccatgga gggacaggag gacgagggca     180
acggggccca gtacagggt atcctggnaa gcctccttgg agctcttnaa attcaccatc      240
ggcatgggcg agctggcctt ccaggagcag ctgcacttcc gcggcatggt gctgctgntg     300
ctgttgggnt tangtgctgc tcanctacat ccngttgctt caacatgttc atnggccttc     360
```

```
atggagcgag ancgttaaaa aattnttggn caattnaana nttgggngca ttttggaagt      420
ttgnaagaaa gncatttttn tccntgggga tggggaatg ggtttnttt ggggttcaag        480 naggaangca angggn                                                      497
```

```
<210> SEQ ID NO 14
<211> LENGTH: 362
<212> TYPE: DNA
<213> ORGANISM: Homo sapiens
<220> FEATURE:
<221> NAME/KEY: Unsure
<222> LOCATION: 305
<223> OTHER INFORMATION: May be any nucleotide
<220> FEATURE:
<221> NAME/KEY: Unsure
<222> LOCATION: 311
<223> OTHER INFORMATION: May be any nucleotide
<220> FEATURE:
<221> NAME/KEY: Unsure
<222> LOCATION: 340
<223> OTHER INFORMATION: May be any nucleotide
<220> FEATURE:
<221> NAME/KEY: Unsure
<222> LOCATION: 348
<223> OTHER INFORMATION: May be any nucleotide
<220> FEATURE:
<221> NAME/KEY: Unsure
<222> LOCATION: 358
<223> OTHER INFORMATION: May be any nucleotide
<220> FEATURE:
<221> NAME/KEY: Unsure
<222> LOCATION: 359
<223> OTHER INFORMATION: May be any nucleotide
<220> FEATURE:
<221> NAME/KEY: Unsure
<222> LOCATION: 360
<223> OTHER INFORMATION: May be any nucleotide

<400> SEQUENCE: 14
ggcagagact gcagtgtgtg aagctcctgg tggagaatgg ggccaatgtg catgcccggg      60
tctgcggcga cttcttccag aagggccaag ggacttgctt ttatttcggt gaagctaccc     120
ctctctttgg ccgcttgcac caagcagtgg gatgtggtaa gctacctcct ggagaaccca     180
caccagcccg ccagcctggc aggccactgg actcccaggg gcaacacagt cctgcatgcc     240
ctagtggatg gatctcggga caacttcagc tgaggaacat tgcactggtg gaccagcatg     300
tatgnttggg ntccttccaa ggttgggggc ccgtctttgn ccctaacntg gcaatttnnn     360
gg                                                                    362
```

```
<210> SEQ ID NO 15
<211> LENGTH: 187
<212> TYPE: DNA
<213> ORGANISM: Homo sapiens
<220> FEATURE:
<221> NAME/KEY: Unsure
<222> LOCATION: 22
<223> OTHER INFORMATION: May be any nucleotide
<220> FEATURE:
<221> NAME/KEY: Unsure
<222> LOCATION: 107
<223> OTHER INFORMATION: May be any nucleotide
<220> FEATURE:
<221> NAME/KEY: Unsure
<222> LOCATION: 129
<223> OTHER INFORMATION: May be any nucleotide
<220> FEATURE:
<221> NAME/KEY: Unsure
<222> LOCATION: 134
<223> OTHER INFORMATION: May be any nucleotide
<220> FEATURE:
```

```
<221> NAME/KEY: Unsure
<222> LOCATION: 150
<223> OTHER INFORMATION: May be any nucleotide
<220> FEATURE:
<221> NAME/KEY: Unsure
<222> LOCATION: 151
<223> OTHER INFORMATION: May be any nucleotide
<220> FEATURE:
<221> NAME/KEY: Unsure
<222> LOCATION: 173
<223> OTHER INFORMATION: May be any nucleotide
<220> FEATURE:
<221> NAME/KEY: Unsure
<222> LOCATION: 183
<223> OTHER INFORMATION: May be any nucleotide

<400> SEQUENCE: 15
ggcagaggga aattcgcccc tnaaataaga gtcaacctca actaccgaaa ggaaacaggt    60
gccagtaagc cggatccaaa ccgatttaac cgagatcggc tcttcantgc ggtctcccgg   120
ggtgtcccna aggntctggc tggacttccn nagtacctga agccaagacc agncaagtac   180 ctnaccg                                                             187

<210> SEQ ID NO 16
<211> LENGTH: 298
<212> TYPE: DNA
<213> ORGANISM: Homo sapiens
<220> FEATURE:
<221> NAME/KEY: Unsure
<222> LOCATION: 40
<223> OTHER INFORMATION: May be any nucleotide
<220> FEATURE:
<221> NAME/KEY: Unsure
<222> LOCATION: 67
<223> OTHER INFORMATION: May be any nucleotide
<220> FEATURE:
<221> NAME/KEY: Unsure
<222> LOCATION: 72
<223> OTHER INFORMATION: May be any nucleotide
<220> FEATURE:
<221> NAME/KEY: Unsure
<222> LOCATION: 81
<223> OTHER INFORMATION: May be any nucleotide
<220> FEATURE:
<221> NAME/KEY: Unsure
<222> LOCATION: 82
<223> OTHER INFORMATION: May be any nucleotide
<220> FEATURE:
<221> NAME/KEY: Unsure
<222> LOCATION: 101
<223> OTHER INFORMATION: May be any nucleotide
<220> FEATURE:
<221> NAME/KEY: Unsure
<222> LOCATION: 109
<223> OTHER INFORMATION: May be any nucleotide
<220> FEATURE:
<221> NAME/KEY: Unsure
<222> LOCATION: 153
<223> OTHER INFORMATION: May be any nucleotide
<220> FEATURE:
<221> NAME/KEY: Unsure
<222> LOCATION: 154
<223> OTHER INFORMATION: May be any nucleotide
<220> FEATURE:
<221> NAME/KEY: Unsure
<222> LOCATION: 158
<223> OTHER INFORMATION: May be any nucleotide
<220> FEATURE:
<221> NAME/KEY: Unsure
<222> LOCATION: 162
<223> OTHER INFORMATION: May be any nucleotide
<220> FEATURE:
<221> NAME/KEY: Unsure
<222> LOCATION: 164
<223> OTHER INFORMATION: May be any nucleotide
```

```
<220> FEATURE:
<221> NAME/KEY: Unsure
<222> LOCATION: 179
<223> OTHER INFORMATION: May be any nucleotide
<220> FEATURE:
<221> NAME/KEY: Unsure
<222> LOCATION: 195
<223> OTHER INFORMATION: May be any nucleotide
<220> FEATURE:
<221> NAME/KEY: Unsure
<222> LOCATION: 196
<223> OTHER INFORMATION: May be any nucleotide
<220> FEATURE:
<221> NAME/KEY: Unsure
<222> LOCATION: 197
<223> OTHER INFORMATION: May be any nucleotide
<220> FEATURE:
<221> NAME/KEY: Unsure
<222> LOCATION: 225
<223> OTHER INFORMATION: May be any nucleotide
<220> FEATURE:
<221> NAME/KEY: Unsure
<222> LOCATION: 241
<223> OTHER INFORMATION: May be any nucleotide
<220> FEATURE:
<221> NAME/KEY: Unsure
<222> LOCATION: 246
<223> OTHER INFORMATION: May be any nucleotide
<220> FEATURE:
<221> NAME/KEY: Unsure
<222> LOCATION: 271
<223> OTHER INFORMATION: May be any nucleotide
<220> FEATURE:
<221> NAME/KEY: Unsure
<222> LOCATION: 282
<223> OTHER INFORMATION: May be any nucleotide

<400> SEQUENCE: 16
gccacgccct ggcctcagcc tgcgggggct ccagtcaggn caacaccgac gcgcactggg      60
gaggaanaac angacccttg nncatctcca tctgcacaga ngtcctggnt gggaccgagc     120
aagcctcctc ctcctaagga tgacctcacc ctnnaagntt cncnagtttt caagttggna    180
gacattagat ggaannnaag aaagatgggt ctgaagcgga cagaggaaa actggatttt    240 ngaacngggt aggttcccaa tggagtaaca ntttccaagg gngaaggacc gggaaatt     298

<210> SEQ ID NO 17
<211> LENGTH: 534
<212> TYPE: DNA
<213> ORGANISM: Homo sapiens
<220> FEATURE:
<221> NAME/KEY: Unsure
<222> LOCATION: 3
<223> OTHER INFORMATION: May be any nucleotide
<220> FEATURE:
<221> NAME/KEY: Unsure
<222> LOCATION: 4
<223> OTHER INFORMATION: May be any nucleotide
<220> FEATURE:
<221> NAME/KEY: Unsure
<222> LOCATION: 396
<223> OTHER INFORMATION: May be any nucleotide
<220> FEATURE:
<221> NAME/KEY: Unsure
<222> LOCATION: 397
<223> OTHER INFORMATION: May be any nucleotide
<220> FEATURE:
<221> NAME/KEY: Unsure
<222> LOCATION: 409
<223> OTHER INFORMATION: May be any nucleotide
<220> FEATURE:
<221> NAME/KEY: Unsure
<222> LOCATION: 433
<223> OTHER INFORMATION: May be any nucleotide
<220> FEATURE:
```

```
<221> NAME/KEY: Unsure
<222> LOCATION: 434
<223> OTHER INFORMATION: May be any nucleotide
<220> FEATURE:
<221> NAME/KEY: Unsure
<222> LOCATION: 444
<223> OTHER INFORMATION: May be any nucleotide
<220> FEATURE:
<221> NAME/KEY: Unsure
<222> LOCATION: 498
<223> OTHER INFORMATION: May be any nucleotide
<220> FEATURE:
<221> NAME/KEY: Unsure
<222> LOCATION: 505
<223> OTHER INFORMATION: May be any nucleotide
<220> FEATURE:
<221> NAME/KEY: Unsure
<222> LOCATION: 516
<223> OTHER INFORMATION: May be any nucleotide
<220> FEATURE:
<221> NAME/KEY: Unsure
<222> LOCATION: 524
<223> OTHER INFORMATION: May be any nucleotide

<400> SEQUENCE: 17
gcnncaggca cgaccctgac catggccacc gggtccatac tcaatccata ctctagtccc     60
atccaagacg gggatcatgc caagggcctc gtggcaacca tccaggtcct ctctgttaac    120
cagcatctca tttggagggc aagcccctta gtcacactgt agctgggagg gttggcgtga    180
ggtcctttgg ggctcctggg gtgtggaagc ctgctccctg tcctctctcc tcatttcctg    240
ggcccttgct ttgatcttga catggagtgg gcagccatt tgcaattgtt gagtgtaccc     300
atggctctcc cctccccaac ccagcaacga caccgaaggt cgttttggag ccctgaaca    360 aatgctgcag ggaaggggga tctgctcatc ccaatnnttc taaatttcng tgtaatccga    420
tccaaaagtt canntcaacg gtgntggcta acaacagcta accgaagaag gcaaggcgtg   480
aagtttgggg ggcaaatntg ggggnaggct gcttgnaaaa aacnggggg aaaa           534

<210> SEQ ID NO 18
<211> LENGTH: 496
<212> TYPE: DNA
<213> ORGANISM: Homo sapiens
<220> FEATURE:
<221> NAME/KEY: Unsure
<222> LOCATION: 44
<223> OTHER INFORMATION: May be any nucleotide
<220> FEATURE:
<221> NAME/KEY: Unsure
<222> LOCATION: 47
<223> OTHER INFORMATION: May be any nucleotide
<220> FEATURE:
<221> NAME/KEY: Unsure
<222> LOCATION: 269
<223> OTHER INFORMATION: May be any nucleotide
<220> FEATURE:
<221> NAME/KEY: Unsure
<222> LOCATION: 273
<223> OTHER INFORMATION: May be any nucleotide
<220> FEATURE:
<221> NAME/KEY: Unsure
<222> LOCATION: 457
<223> OTHER INFORMATION: May be any nucleotide

<400> SEQUENCE: 18
gacaggggag agttaagctc ccggttctcc accgtgccgg ctgncanggt gggctgaggg     60
tgaccgagag accagaacct gcttgctgga gcttagtgct cagagctggg gagggaggtt    120
ccgccgctcc tctgctgtca gcgccggcag ccctccgg cttcacttcc tcccgcagcc     180
cctgctactg agaagctccg ggatcccagc agccgccacg ccctggcctc agcctgcggg    240
```

```
gctccagtca ggccaacacc gacgcgcant ggngaggaag acaggaccct tgacatctcc    300
atctgcacag aggtcctggc tggaccgagc agcctcctcc tcctaggatg acctcaccct    360
ccagctctcc agttttcagg ttggagacat tagatggagg ccaagaagat ggctctgagg    420
cggacagagg aaagctggat tttgggagcg ggctgcntcc catggagtca cagttccagg    480
gcgaggaccg gaaatt                                                    496
```

<210> SEQ ID NO 19
<211> LENGTH: 454
<212> TYPE: DNA
<213> ORGANISM: Homo sapiens

<400> SEQUENCE: 19

```
aatggcgatg tgcagagcgc tgtggcctcg gtaatagtca tctgtgcact gggcatttac     60
caggggctga ggattgccag agtccctgtc gatctgcagc agtggcagaa tgcaggcatt    120
gactccgtcc ttaaggttca gcacagcctt catcaggcac gtcttacctg tggagccctc    180
tgtgtattcc gagtcggtga ggtacttgct ggtcttgctc aggtactctg gaagtccagc    240
cagatcctcg gggacacccc gggagaccgc attgaagagc cgatctcggt caaatcggtt    300
tggatccggc tgactggcac ctgttccctt tcggtagttg aggttgactc ttatctgagg    360
ggcgaatttc cggtcctcgc cctggaactg tgactccatg ggaggcagcc cgctcccaaa    420
atccagcttt cctctgtccg cctcagagcc atct                                454
```

<210> SEQ ID NO 20
<211> LENGTH: 461
<212> TYPE: DNA
<213> ORGANISM: Homo sapiens
<220> FEATURE:
<221> NAME/KEY: Unsure
<222> LOCATION: 96
<223> OTHER INFORMATION: May be any nucleotide
<220> FEATURE:
<221> NAME/KEY: Unsure
<222> LOCATION: 461
<223> OTHER INFORMATION: May be any nucleotide

<400> SEQUENCE: 20

```
tcggtgagct accctctct ttggccgctt gcaccaagca gtgggatgtg gtaagctacc      60
tcctggagaa cccacaccag cccgccagcc tgcagncact gactcccagg gcaacacagt    120
cctgcatgcc ctagtgatga tctcggacaa ctcagctgag aacattgcac tggtgaccag    180
catgtatgat gggctcctcc aagctggggc ccgcctctgc cctaccgtgc agcttgagga    240
catccgcaac ctgcaggatc tcacgcctct gaagctggcc gccaaggagg caagatcga    300 gattttcagg cacatcctgc agcgggagtt ttcaggactg agccaccttt cccgaaagtt    360
caccgagtgg tgctatgggc ctgtccgggt gtcgctgtat gacctggctt ctgtggacag    420
ctgtgaggag aactcagtgc tggagatcat tgcctttcaa n                        461
```

<210> SEQ ID NO 21
<211> LENGTH: 478
<212> TYPE: DNA
<213> ORGANISM: Homo sapiens
<220> FEATURE:
<221> NAME/KEY: Unsure
<222> LOCATION: 77
<223> OTHER INFORMATION: May be any nucleotide
<220> FEATURE:
<221> NAME/KEY: Unsure
<222> LOCATION: 249

```
<223> OTHER INFORMATION: May be any nucleotide
<220> FEATURE:
<221> NAME/KEY: Unsure
<222> LOCATION: 279
<223> OTHER INFORMATION: May be any nucleotide
<220> FEATURE:
<221> NAME/KEY: Unsure
<222> LOCATION: 283
<223> OTHER INFORMATION: May be any nucleotide
<220> FEATURE:
<221> NAME/KEY: Unsure
<222> LOCATION: 338
<223> OTHER INFORMATION: May be any nucleotide
<220> FEATURE:
<221> NAME/KEY: Unsure
<222> LOCATION: 477
<223> OTHER INFORMATION: May be any nucleotide

<400> SEQUENCE: 21
gctagcctgt cctgacaggg agagttaagc tcccgttctc caccgtgccg gctggcaggt    60
gggctgaggg tgaccgngag accagaacct gcttgctgga gcttagtgct cagagctggg   120
gagggaggtt ccgccgctcc tctgctgtca gcgccggcag cccctcccgg cttcacttcc   180
tcccgcagcc cctgctactg agaagctccg ggatcccagc agccgccacg ccctggcctc   240
agcctgcgng gctccagtca ggccaacacc gacgcgcant ggngaggaag acaggaccct   300
tgacatctcc atctgcacag aggtcctggc tggacgangc agcctcctcc tcctaggatg   360
acctcaacct ccagctctcc agttttcagg ttggagacat tagatggagg ccaagaagat   420
ggctctgagg cggacagagg aaagctggat tttgggaagc gggctgcctc ccatggnt    478

<210> SEQ ID NO 22
<211> LENGTH: 433
<212> TYPE: DNA
<213> ORGANISM: Homo sapiens
<220> FEATURE:
<221> NAME/KEY: Unsure
<222> LOCATION: 312
<223> OTHER INFORMATION: May be any nucleotide
<220> FEATURE:
<221> NAME/KEY: Unsure
<222> LOCATION: 341
<223> OTHER INFORMATION: May be any nucleotide
<220> FEATURE:
<221> NAME/KEY: Unsure
<222> LOCATION: 427
<223> OTHER INFORMATION: May be any nucleotide

<400> SEQUENCE: 22
attcactggg accccagagc cagcagatgt ggttggaaag atcctctgct ctgtcctctg    60
gcctcctgct gcatctgggc catcagttgg actggaggag ctggacgggc acatagtttt   120
cctcagaggc accatcctca tcctccttgg gaggggaagc caggacaggg ttctcgagag   180
ttcgagggac acctgcccct gacgggtcct cacacagcgt aggcagcgtc tgctcccatg   240
aagcccagtt cacctcctcc accctgaagc accagcgctc atccgggctg ccatctggct   300
tagtgccaac gntcagcatc acacctgccc gctgcttctt nctgcaccac caatagccat   360
tctccatctc caggacagga gatggctttc tgcagcttcc agatgctcca gctgtcagtg   420
gcgacantgt tga                                                    433

<210> SEQ ID NO 23
<211> LENGTH: 430
<212> TYPE: DNA
<213> ORGANISM: Homo sapiens

<400> SEQUENCE: 23
```

```
aatggcgatg tgcagacgct gtggcctcgg taatagtcat ctgtgcactg ggcatttacc      60 agggggctgag gattgccaga gtccctgtcg atctgcagca gtggcagaat gcaggcattg    120
accccgtcct taaggttcag cacagccttc atcaggcacg tcttacctgt ggagccctct    180
gtgtattccg agtcggtgag gtacttgctg gtcttgctca ggtactctgg aagtccagcc    240
agatcctcgg ggacaccccg ggagaccgca ttgaagagcg atctcggtc aaatcggttt     300 ggatccggct gactggcatc tgttcccttt cggtagttga ggttgactct tatctgaggg    360
gcgaatttcc ggtcctcgcc ctggaactgt gactccatgg gaggcagccc gctcccaaaa    420
tccagctttc                                                           430

<210> SEQ ID NO 24
<211> LENGTH: 408
<212> TYPE: DNA
<213> ORGANISM: Homo sapiens

<400> SEQUENCE: 24
aatggcgatg tgcagagcgc tgtggcctcg gtaatagtca tctgtgcact gggcatttac      60
caggggctga ggattgccag agtcccggtc gatctgcagc agtggcagaa tgcaggcatt    120
gaccccgtcc ttaaggttca gcacagcctt catcaggcac gtcttacctg tggagccctc    180
tgtgtattcc gagtcggtga ggtacttgct ggtcttgctc aggtactctg gaagtccagc    240
cagatcctcg gggacacccc gggagaccgc attgaagagc cgatctcggt caaatcggtt    300
tggatccggc tgactggcac ctgttccctt tcggtagttg aggttgactc ttatctgagg    360
ggcgaatttc cggtcctcgc cctgggaact gtgactccat gggaggca                 408

<210> SEQ ID NO 25
<211> LENGTH: 422
<212> TYPE: DNA
<213> ORGANISM: Homo sapiens
<220> FEATURE:
<221> NAME/KEY: Unsure
<222> LOCATION: 7
<223> OTHER INFORMATION: May be any nucleotide
<220> FEATURE:
<221> NAME/KEY: Unsure
<222> LOCATION: 297
<223> OTHER INFORMATION: May be any nucleotide
<220> FEATURE:
<221> NAME/KEY: Unsure
<222> LOCATION: 354
<223> OTHER INFORMATION: May be any nucleotide

<400> SEQUENCE: 25
ttcttcnggg taggctgatg gtaggcaaca gagttgaaga tgaacatgta gatcagatta      60
cacaggaagt ttaagaagaa cttggggatg agcagatccc atttcgcctg cagcagtttg    120 ttcagggggct ccaaaacgac cattcggtgt cggtgcgggc tcttgcaatg aaaggcaatg    180
atctccagca ctgagttctc ctcacagctg tccacagaag ccaggtcata cagcgacacc    240
cggacaggcc catagcacca ctcggtgaac tttcgggaaa ggtggctcag tcctganaac    300
tccccgctgc aggatgtgcc tgaaaatctc gatcttgccc tccttggcgg ccantttcag    360
aggcgtgaga tcctgcaggt tgcggatgtc ctcaagctgc acggtagggc agagggcggg    420
cc                                                                   422

<210> SEQ ID NO 26
<211> LENGTH: 424
<212> TYPE: DNA
```

```
<213> ORGANISM: Homo sapiens

<400> SEQUENCE: 26
gtttttgagg ttagtgaaaa tatatatttg ccaccagaat tcactgggac cccagagcca      60
gcagatgtgg ttggaaagat cctctgctct gtcctctggc ctcctgctgc atctgggcca     120
tcagttggac tggaggagct ggacgggcac atagttttcc tcagaggcac catcctcatc     180
ctccttggga ggggaagcca ggacagggtt ctcgagagtt cgaggacac ctgcccctga      240 cgggtcctca cacagcgtag gcagcgtctg ctcccatgaa gcccagttca cctcctccac     300
cctgaagcac cagcgctcat ccgggctgcc atctggctta gtgccaacgg tcagcatcac     360
acctgcccgc tgcttcttcc tgcaccacca atagccattc tccatctcca ggacagagat     420
ggct                                                                  424

<210> SEQ ID NO 27
<211> LENGTH: 432
<212> TYPE: DNA
<213> ORGANISM: Homo sapiens
<220> FEATURE:
<221> NAME/KEY: Unsure
<222> LOCATION: 149
<223> OTHER INFORMATION: May be any nucleotide
<220> FEATURE:
<221> NAME/KEY: Unsure
<222> LOCATION: 150
<223> OTHER INFORMATION: May be any nucleotide
<220> FEATURE:
<221> NAME/KEY: Unsure
<222> LOCATION: 350
<223> OTHER INFORMATION: May be any nucleotide
<220> FEATURE:
<221> NAME/KEY: Unsure
<222> LOCATION: 428
<223> OTHER INFORMATION: May be any nucleotide

<400> SEQUENCE: 27
tgtttcctgg ccatcgagtg gtacctgccc ctgcttgtgt ctgcgctggt gctgggctgg      60
ctgaacctgc tttactatac acgtggcttc cagcacacag gcatctacag tgtcatgatc     120
cagaagccct ggtgagcctg agccaggann ttggcgcccc gaagctccta caggccccaa     180
tgccacagag tcagtgcagc ccatggaggg acaggaggac gagggcaacg gggcccagta     240 cagggtatc ctggaagcct ccttggagct cttcaaattc accatcggca tgggcgagct      300
ggccttccag gagcagctgc acttccgcgc catgggtgct gctgctgctn ctggcctacg     360
tgctgctcac ctacatcctg ctgctcaaca tgctcatcgc cctcatggag cgagaccgtc     420
aacaggtntc gc                                                         432

<210> SEQ ID NO 28
<211> LENGTH: 383
<212> TYPE: DNA
<213> ORGANISM: Homo sapiens

<400> SEQUENCE: 28
aatggcgatg tgcagagcgc tgtggcctcg gtaatagtca tctgtgcact gggcatttac      60
caggggctga ggattgccag agtccctgtc gatctgcagc agtggcagaa tgcaggcatt     120
gactccgtcc ttaaggttca gcacagcctt catcaggcac gtcttacctg tggagccctc     180
tgtgtattcc gagtcggtga ggtacttgct ggtcttgctc aggtactctg gaagtccagc     240
cagatcctcg gggacacccc gggagaccgc attgaagagc cgatctcggt caaatcggtt     300
tggatccggc tgactggcac ctgttccctt tcggtagttg aggttgactc ttatctgagg     360
```

```
ggcgaatttc cggtcctcgc cct                                            383

<210> SEQ ID NO 29
<211> LENGTH: 375
<212> TYPE: DNA
<213> ORGANISM: Homo sapiens

<400> SEQUENCE: 29
aatggcgatg tgcagagcgc tgtggcctcg gtaatagtca tctgtgcact gggcatttac     60 cagggctga ggattgccag agtccctgtc gatctgcagc agtggcagaa tgcaggcatt    120
gaccccgtcc ttaaggttca gcacagcctt catcaggcac gtcttacctg tggagccctc   180
tgtgtattcc gagtcggtga ggtacttgct ggtcttgctc aggtactctg gaagtccagc   240
cagatcctcg gggacacccg ggagaccgca ttgaagagcc gatctcggtc aaatcggttt   300
ggatccggct gactggcacc tgttcccttt cggtagttga ggttgactct tatctgaggg   360
gcgaatttcc ggtcc                                                    375

<210> SEQ ID NO 30
<211> LENGTH: 463
<212> TYPE: DNA
<213> ORGANISM: Homo sapiens
<220> FEATURE:
<221> NAME/KEY: Unsure
<222> LOCATION: 21
<223> OTHER INFORMATION: May be any nucleotide
<220> FEATURE:
<221> NAME/KEY: Unsure
<222> LOCATION: 305
<223> OTHER INFORMATION: May be any nucleotide
<220> FEATURE:
<221> NAME/KEY: Unsure
<222> LOCATION: 453
<223> OTHER INFORMATION: May be any nucleotide

<400> SEQUENCE: 30
gagaggtcct ggctggacca ngcagcctcc tcctcctagg atgacctcac cctccagctc     60
tccagttttc aggttggaga cattagatgg aggccaagaa gatggctctg aggcggacag    120
aggaaagctg gattttggga gcgggctgcc tcccatggag tcacagttcc agggcgagga    180
ccggaaattc gcccctcaga taagagtcaa cctcaactac cgaaagggaa caggtgccag    240
tcagccggat ccaaaccgat ttgaccgaga tcggctcttc aatgcggtct cccgggggtgt   300 ccccnaggat ctggctggac ttccagagta cctgagcaag accagcaagt accttaccga    360
cttggaatta cacagagggc ttccacaggt taagacgttg cctgatggaa ggctgtgttg    420
aactttaagg acggggttca attgcttgct ttntgccatt gtt                     463

<210> SEQ ID NO 31
<211> LENGTH: 484
<212> TYPE: DNA
<213> ORGANISM: Homo sapiens
<220> FEATURE:
<221> NAME/KEY: Unsure
<222> LOCATION: 300
<223> OTHER INFORMATION: May be any nucleotide

<400> SEQUENCE: 31
ggtgagctac ccctctcttt ggccgcttgc accaagcagt gggatgtggt aagctacctc     60
ctggagaacc cacaccagcc cgccagcctg caggcactga ctcccagggc aacacagtcc    120
tgcatgccct agtgatgatc tcggacaact cagctgagaa cattgcactg gtgaccagca    180
```

| | |
|---|---|
| tgtatgatgg gctcctccaa gctggggccc gcctctgccc taccgtgcaa gcttgaggac | 240 |
| atccgcaacc tgcaggatct cacgcctctg aaagctggcc gccaaggagg gcaagatcgn | 300 |
| gattttcaag gcacatcctt gcaagcggga gttttcagga ctgaagccac cttttccccg | 360 |
| aaagttcacc gagtggtggc taatgggccc tgtccgggtt gtcgctgtaa tgacctgggc | 420 |
| tttctgtgga cagctgtgag gagaactcag tgctgggaat cattgccttt catttgcaaa | 480 |
| agcc | 484 |

<210> SEQ ID NO 32
<211> LENGTH: 370
<212> TYPE: DNA
<213> ORGANISM: Homo sapiens

<400> SEQUENCE: 32

| | |
|---|---|
| aatggcgatg tgcagacgct gtggcctcgg taatagtcat ctgtgcactg ggcatttacc | 60 |
| aggggctgag gattgccaga gtcccggtcg atctgcagca gtggcagaat gcaggcattg | 120 |
| accccgtcct taaggttcag cacagccttc atcaggcacg tcttacctgt ggagccctct | 180 |
| gtgtattccg agtcggtgag gtacttgctg gtcttgctca ggtactctgg aagtccagcc | 240 |
| agatcctcgg ggacaccccg ggagaccgca ttgaagagcc gatctcggtc aaatcggttt | 300 |
| ggatccggct gactggcacc tgttcccttt cggtagttga ggttgactct tatctgaggg | 360 |
| gcgactcgtg | 370 |

<210> SEQ ID NO 33
<211> LENGTH: 375
<212> TYPE: DNA
<213> ORGANISM: Homo sapiens

<400> SEQUENCE: 33

| | |
|---|---|
| gcagccgcac gccctggcct cagcctgcgt ggctccagtc aggccaacac cgacgcgcac | 60 |
| tggcgaggaa gacaggaccc ttgacatctc catctgcaca gaggtcctgg ctggccgagc | 120 |
| agcctcctcc tcctaggatg acctcaccct ccagctctcc agttttcagg ttggagacat | 180 |
| tagatggagg ccaagaagat ggctctgagg cggacagagg aaagctggat tttgggagcg | 240 |
| ggctgcctcc catggagtca cagttccagg gcgaggaccg gaaattcgcc cctcagataa | 300 |
| gagtcaacct caactaccga aaggaacagg tgccagtcag ccggatccaa accgatttga | 360 |
| ccgagatcgg ctctt | 375 |

<210> SEQ ID NO 34
<211> LENGTH: 401
<212> TYPE: DNA
<213> ORGANISM: Homo sapiens
<220> FEATURE:
<221> NAME/KEY: Unsure
<222> LOCATION: 275
<223> OTHER INFORMATION: May be any nucleotide
<220> FEATURE:
<221> NAME/KEY: Unsure
<222> LOCATION: 366
<223> OTHER INFORMATION: May be any nucleotide
<220> FEATURE:
<221> NAME/KEY: Unsure
<222> LOCATION: 376
<223> OTHER INFORMATION: May be any nucleotide
<220> FEATURE:
<221> NAME/KEY: Unsure
<222> LOCATION: 389
<223> OTHER INFORMATION: May be any nucleotide
<220> FEATURE:
<221> NAME/KEY: Unsure

```
<222> LOCATION: 396
<223> OTHER INFORMATION: May be any nucleotide

<400> SEQUENCE: 34
aatggcgatg tgcagagcgc tgtggcctcg gtaatagtca tctgtgcact gggcatttac      60
caggggctga ggattgccag agtcccggtc gatctgcagc agtggcagaa tgcaggcatt     120
gaccccgtcc ttaaggttca gcacagcctt catcaggcac gtcttacctg tggagccctc    180
tgtgtattcc gagtcggtga ggtacttgct ggtcttgctc aggtactctg gaagtccagc    240
cagatcctcg gggacacccc ggggagaccg cattnaagag ccgatcttgg gtcaaatcgg    300
tttggatccg gctgactggc acctgttccc tttcggtagt tgaggttgac tcttattctg    360 agggngcga attttncggt ccttcgccng gggaantttg a                          401

<210> SEQ ID NO 35
<211> LENGTH: 463
<212> TYPE: DNA
<213> ORGANISM: Homo sapiens
<220> FEATURE:
<221> NAME/KEY: Unsure
<222> LOCATION: 420
<223> OTHER INFORMATION: May be any nucleotide
<220> FEATURE:
<221> NAME/KEY: Unsure
<222> LOCATION: 449
<223> OTHER INFORMATION: May be any nucleotide

<400> SEQUENCE: 35
agaggtcctg gctggacatg cagcctcctc ctcctaggat gacctcaccc tccagctctc      60
cagttttcag gttggagaca ttagatggag gccaagaaga tggctctgag gcggacagag    120
gaaagctgga tttttgggagc gggctgcctc ccatggagtc acagttccag ggcgaggacc    180
ggaaattcgc ccctcagata agagtcaacc tcaactaccg aaagggaaca ggtgccagtc    240
agccggatcc aaaccgattt gaccgagatc ggctcttcaa tgcggtctcc cggggtgtcc    300
ccgaggatct ggctggactt ccagagtacc tgagcaagac cagcaagtaa cctcaccgac    360
ttggaattac acagagggt tccacaggtt aagacgttgc ctgattgaaa gggttgttgn    420
tgaaacttta aggacgggg tcaattgcnt gcattttgc ctt                        463

<210> SEQ ID NO 36
<211> LENGTH: 374
<212> TYPE: DNA
<213> ORGANISM: Homo sapiens
<220> FEATURE:
<221> NAME/KEY: Unsure
<222> LOCATION: 112
<223> OTHER INFORMATION: May be any nucleotide
<220> FEATURE:
<221> NAME/KEY: Unsure
<222> LOCATION: 318
<223> OTHER INFORMATION: May be any nucleotide

<400> SEQUENCE: 36
aatggcgatg tgcagagcgc tgtggcctcg gtaatagtca tctgtgcact gggcatttac      60
caggggctga ggattgccag agtcccggtc gatctgcagc agtggcagaa tncaggcatt    120
gaccccgtcc ttaaggttca gcacagcctt catcaggcac gtcttacctg tggagccctc    180
tgtgtattcc gagtcggtga ggtacttgct ggtcttgctc aggtactctg gaagtccagc    240
cagatcctcg gggacacccc ggggagaccgc atttgaagag ccgatctcgg tcaaatcagg    300
tttggatccg gctgactngg cacctgttcc ctttcggtag tttgaggttg actcttatct    360
``` gagggggcgaa tttc    374

<210> SEQ ID NO 37
<211> LENGTH: 401
<212> TYPE: DNA
<213> ORGANISM: Homo sapiens
<220> FEATURE:
<221> NAME/KEY: Unsure
<222> LOCATION: 267
<223> OTHER INFORMATION: May be any nucleotide
<220> FEATURE:
<221> NAME/KEY: Unsure
<222> LOCATION: 333
<223> OTHER INFORMATION: May be any nucleotide
<220> FEATURE:
<221> NAME/KEY: Unsure
<222> LOCATION: 352
<223> OTHER INFORMATION: May be any nucleotide

<400> SEQUENCE: 37
aatcggcgat gtgcagaggc tcgtggcctc ggtaatagtc atctgtgcac tgggcattta    60
ccaggggctg aggattgcca gagtccctgt cgatctgcag cagtggcaga atgcaggcat    120
tcgactccgt ccttaaggtt cagcacagcc ttcatcaggc acgtcttacc tgtggagccc    180
tctgtgtatt ccgagtcggt gaggtacttg ctggtcttgc tcaggtactc tggaagtcca    240
gccagatcct cggggacacc ccgggangac cgcattgaag agccgatctc ggtcaaatcg    300
gtttggatcc ggctgacttg gcacctgttc ccnttcggta gttgaggttg antcttatct    360
gagggggcga atttccggtc ctcgccctgg aactgtgact c    401

<210> SEQ ID NO 38
<211> LENGTH: 403
<212> TYPE: DNA
<213> ORGANISM: Homo sapiens
<220> FEATURE:
<221> NAME/KEY: Unsure
<222> LOCATION: 179
<223> OTHER INFORMATION: May be any nucleotide

<400> SEQUENCE: 38
agtgaaaata tatatttgcc accagaattc actgggaccc cagagccagc agatgtggtt    60
ggaaagatcc tctgctctgt cctctggcct cctgctgcat ctgggccatc agttggactg    120
gaggagctgg acgggcacat agtttcctc agaggcacca tcctcatcct ccttgggang    180
gcgaagccag acagggttc tcgagagttc gagggacacc tgcccctgac gggtcctcac    240
acagcgtagg cacgcgtctg ctcccatgaa gcccaagttc acctcctcca ccctgaagca    300
ccaagcgctt cattcggggc tgccatctgg ctttagtgcc aacggtcagc atcacacctg    360
cccgctgctt tcttcctgca ccaccaatag ccattctcca tct    403

<210> SEQ ID NO 39
<211> LENGTH: 406
<212> TYPE: DNA
<213> ORGANISM: Homo sapiens
<220> FEATURE:
<221> NAME/KEY: Unsure
<222> LOCATION: 18
<223> OTHER INFORMATION: May be any nucleotide
<220> FEATURE:
<221> NAME/KEY: Unsure
<222> LOCATION: 353
<223> OTHER INFORMATION: May be any nucleotide
<220> FEATURE:
<221> NAME/KEY: Unsure
<222> LOCATION: 375
<223> OTHER INFORMATION: May be any nucleotide
<220> FEATURE:
<221> NAME/KEY: Unsure
<222> LOCATION: 396
<223> OTHER INFORMATION: May be any nucleotide
<220> FEATURE:
<221> NAME/KEY: Unsure
<222> LOCATION: 402
<223> OTHER INFORMATION: May be any nucleotide

<400> SEQUENCE: 39

```
agaggtcctg gctggacncg cagcctcctc ctcctaggat gacctcaccc tccagctctc      60
cagttttcag gttggagaca ttagatggag gccaagaaga tggctctgag gcggacagag     120
gaaagctgga ttttgggagc gggctgcctc ccatggagtc acagttccag ggcgaggacc     180
ggaaattcgc ccctcagata agagtcaacc tcaactaccg aaagggaaca ggtgccagtc     240
agccggatcc aaaccgattt gaccgagatc ggcttcttca atgcggtctc ccggggtgtc     300
cccgaggatc tggctgggat ttccagagta accttgagca agaccagcaa gtnacttcac     360
cgatttggga ataanacaga ggggtttcca gaagtnaagg antttg                    406
```

<210> SEQ ID NO 40
<211> LENGTH: 319
<212> TYPE: DNA
<213> ORGANISM: Homo sapiens
<220> FEATURE:
<221> NAME/KEY: Unsure
<222> LOCATION: 8
<223> OTHER INFORMATION: May be any nucleotide
<220> FEATURE:
<221> NAME/KEY: Unsure
<222> LOCATION: 57
<223> OTHER INFORMATION: May be any nucleotide
<220> FEATURE:
<221> NAME/KEY: Unsure
<222> LOCATION: 162
<223> OTHER INFORMATION: May be any nucleotide
<220> FEATURE:
<221> NAME/KEY: Unsure
<222> LOCATION: 167
<223> OTHER INFORMATION: May be any nucleotide
<220> FEATURE:
<221> NAME/KEY: Unsure
<222> LOCATION: 285
<223> OTHER INFORMATION: May be any nucleotide

<400> SEQUENCE: 40

```
ttccaggngc agctgcactt ccgcggcatg gtgctgctgc tgctgctggc ctacgtnctg      60
ctcacctaca tcctgctgct caacatgctc atcgccctca tgagcgagac cgtcaacagt     120
gtcgccactg acagctggag catctggaag ctgcagaaag cnatctntgt cctggagatg     180
gagaatggct attggtggtg caggaagaag cagcgggcag gtgtgatgct gaccgttggc     240
actaagccag atggcagccc cgatgagcgc tggtgcttca gggtngagga ggtgaactgg     300
gcttcatggg gagcagacg                                                  319
```

<210> SEQ ID NO 41
<211> LENGTH: 423
<212> TYPE: DNA
<213> ORGANISM: Homo sapiens
<220> FEATURE:
<221> NAME/KEY: Unsure
<222> LOCATION: 23
<223> OTHER INFORMATION: May be any nucleotide
<220> FEATURE:
<221> NAME/KEY: Unsure
<222> LOCATION: 42
<223> OTHER INFORMATION: May be any nucleotide
<220> FEATURE:

```
<221> NAME/KEY: Unsure
<222> LOCATION: 59
<223> OTHER INFORMATION: May be any nucleotide
<220> FEATURE:
<221> NAME/KEY: Unsure
<222> LOCATION: 266
<223> OTHER INFORMATION: May be any nucleotide
<220> FEATURE:
<221> NAME/KEY: Unsure
<222> LOCATION: 270
<223> OTHER INFORMATION: May be any nucleotide
<220> FEATURE:
<221> NAME/KEY: Unsure
<222> LOCATION: 353
<223> OTHER INFORMATION: May be any nucleotide
<220> FEATURE:
<221> NAME/KEY: Unsure
<222> LOCATION: 417
<223> OTHER INFORMATION: May be any nucleotide

<400> SEQUENCE: 41
acaggggaga gttaagctcc cgntctccac cgtgccggct gncaggtggg ctgagggtna      60
ccgagagacc agaacctgct tgctggagct tagtgctcag agctggggag ggaggttccg     120
ccgctcctct gctgtcagcg ccggcagccc ctcccggctt cacttcctcc cgcagcccct     180
gctactgaga agctccggga tcccagcagc cgccacgccc tggcctcagc ctgcggggct     240
ccagtcaggc caacaccgac gcgcantggn gaggaagaca ggaccttga catctccatc      300 tgcacagagg tcctggctgg acgagcagcc tcctcctcct tagggatgaa ctnaaccttc     360
caagctcttc cagttttaa ggtttggaga acatttagat tggagggcca agaagantgg      420
ctt                                                                   423

<210> SEQ ID NO 42
<211> LENGTH: 386
<212> TYPE: DNA
<213> ORGANISM: Homo sapiens
<220> FEATURE:
<221> NAME/KEY: Unsure
<222> LOCATION: 304
<223> OTHER INFORMATION: May be any nucleotide
<220> FEATURE:
<221> NAME/KEY: Unsure
<222> LOCATION: 310
<223> OTHER INFORMATION: May be any nucleotide
<220> FEATURE:
<221> NAME/KEY: Unsure
<222> LOCATION: 318
<223> OTHER INFORMATION: May be any nucleotide
<220> FEATURE:
<221> NAME/KEY: Unsure
<222> LOCATION: 345
<223> OTHER INFORMATION: May be any nucleotide

<400> SEQUENCE: 42
aatggcgatg tgcagagcgc tgtggcctcg gtaatagtca tctgtgcact gggcatttac      60 cagggggctga ggattgccag agtcccggtc gatctgcagc agtggcagaa tgcaggcatt    120
gaccccgtcc ttaaggttca gcacagcctt catcaggcac gtcttacctg tggagccctc     180
tgtgtattcc gagtcggtga ggtacttgct ggtcttgctc aggtactctg gaagtccagc     240
cagatcctcg gggacacccc ggggagaccg cattgaagag ccgatcttgg gtcaaatcgg     300
tttngatccn gctgactngg cacctgtttc cctttcggta gtttnaggtt gaattttatt     360 ctgaggggc gaattttccg gtcctc                                           386

<210> SEQ ID NO 43
<211> LENGTH: 294
```

```
<212> TYPE: DNA
<213> ORGANISM: Homo sapiens

<400> SEQUENCE: 43
tcggtgagct acccctctct ttggccgctt gcaccaagca gtgggatgtg gtaagctacc    60
tcctggagaa cccacaccag cccgccagcc tgcaggccac tgactcccag ggcaacacag   120
tcctgcatgc cctagtgatg atctcggaca actcagctga gaacattgca ctggtgacca   180
gcatgtatga tgggctcctc caagctgggg cccgcctctg ccctaccgtg cagcttgagg   240
acatccgcaa cctgcaggat ctcacgcctc tgaagctggc cgccaaggag ggca         294

<210> SEQ ID NO 44
<211> LENGTH: 326
<212> TYPE: DNA
<213> ORGANISM: Homo sapiens
<220> FEATURE:
<221> NAME/KEY: Unsure
<222> LOCATION: 26
<223> OTHER INFORMATION: May be any nucleotide
<220> FEATURE:
<221> NAME/KEY: Unsure
<222> LOCATION: 46
<223> OTHER INFORMATION: May be any nucleotide
<220> FEATURE:
<221> NAME/KEY: Unsure
<222> LOCATION: 150
<223> OTHER INFORMATION: May be any nucleotide
<220> FEATURE:
<221> NAME/KEY: Unsure
<222> LOCATION: 301
<223> OTHER INFORMATION: May be any nucleotide
<220> FEATURE:
<221> NAME/KEY: Unsure
<222> LOCATION: 308
<223> OTHER INFORMATION: May be any nucleotide
<220> FEATURE:
<221> NAME/KEY: Unsure
<222> LOCATION: 323
<223> OTHER INFORMATION: May be any nucleotide

<400> SEQUENCE: 44
gagaactcag tgctggagat cattgncttt cattgcaaga gcccgnaccg acaccgaatg    60
gtcgttttgg agcccctgaa caaactgctg caggcgaaat gggatctgct catccccaag   120
ttcttcttaa acttcctgtg taatctgatn tacatgttca tcttcaccgc tgttgcctac   180
catcagccta ccctgaagaa gcaggccgcc ctcacctga aagcggaggt tggaaactcc    240
atgctgctga cgggccacat ccttatcctg ctagggggga tctacctcct cgtggggcaa   300
naagtggnaa attttggggg ggnaat                                        326

<210> SEQ ID NO 45
<211> LENGTH: 299
<212> TYPE: DNA
<213> ORGANISM: Homo sapiens
<220> FEATURE:
<221> NAME/KEY: Unsure
<222> LOCATION: 83
<223> OTHER INFORMATION: May be any nucleotide
<220> FEATURE:
<221> NAME/KEY: Unsure
<222> LOCATION: 95
<223> OTHER INFORMATION: May be any nucleotide

<400> SEQUENCE: 45
ttcaggactg agccaccttt cccgaaagtt caccgagtgg tgctatgggc ctgtccgggt    60
gtcgctgtat gacctggctt ctntggacag ctgtnaggag aactcagtgc tggagatcat   120
```

```
tgcctttcat tgcaagagcc cgcaccgaca ccgaatggtc gttttggagc ccctgaacaa      180
actgctgcag gcggaaatgg gatctgctca tccccaagtt cttcttaaac ttcctgtgta      240
atctgatcta catgttcatc ttcaacgctg ttgcctacca tcagcctacc ctgaagaag       299
```

<210> SEQ ID NO 46
<211> LENGTH: 451
<212> TYPE: DNA
<213> ORGANISM: Homo sapiens

<400> SEQUENCE: 46

```
attcggcaca ggctcttcag tgtggtctcc cggggtgtcc caggagctga ctggactgct      60
agagtacctg cgccggacca gcaagtacct cactgactcg gcatacacag aaggctccac     120
tggaaagacg tgcctgatga aggctgtgct gaaccttcag gatgggtca atgcctgtat     180 cctgccgctg ctgcagattg acaggggattc cggcaatcct cagccccttg tcaatgccca     240
gtgcaccgat gagttctacc gaggccacag tgcgctgcac atcgccatag agaagaggag     300
cctgtggtgc gtgaactgct ggtagagaat ggagcgaatg ttcacatccg agcctgtggc     360
gcttcttcca aaagcaccaa ggaacttgtt tctattttgg gagagctacc tctttctctg     420
gcagcgtgca ccaagcagtg ggatgtggtg a                                    451
```

<210> SEQ ID NO 47
<211> LENGTH: 305
<212> TYPE: DNA
<213> ORGANISM: Homo sapiens
<220> FEATURE:
<221> NAME/KEY: Unsure
<222> LOCATION: 256
<223> OTHER INFORMATION: May be any nucleotide

<400> SEQUENCE: 47

```
gagttagtga aaatatatat ttgccaccag aattcactgg daccccagag ccagcagatg      60
tggttggaaa gatcctctgc tctgtcctct ggcctcctgc tgcatctggg ccatcagttg     120
gactggagga gctggacggg cacatagttt tcctcagagg caccatcctc atcctccttg     180
ggaggggaag ccaggacagg gttctcgaga gttcgaggga cacctgcccc tgacgggtcc     240
tcacacagcg taggangcgt ctgctcccat gaagcccagt tcacctcctc caccctgaag     300
cacca                                                                 305
```

<210> SEQ ID NO 48
<211> LENGTH: 333
<212> TYPE: DNA
<213> ORGANISM: Homo sapiens
<220> FEATURE:
<221> NAME/KEY: Unsure
<222> LOCATION: 259
<223> OTHER INFORMATION: May be any nucleotide
<220> FEATURE:
<221> NAME/KEY: Unsure
<222> LOCATION: 325
<223> OTHER INFORMATION: May be any nucleotide

<400> SEQUENCE: 48

```
gagttagtga aaatatatat ttgccaccag aattcactgg daccccagag ccagcagatg      60
tggttggaaa gatcctctgc tctgtcctct ggcctcctgc tgcatctggg ccatcagttg     120
gactggagga gctggacggg cacatagttt tcctcagagg caccatcctc atcctccttg     180
ggaggggaag ccaggacagg gttctcgaga gttcgaggga cacctgcccc tgacgggtc     240 ctcacacagc gtaggcagng tctgctccca tgaagcccag ttcacctcct ccaccctgaa     300
```

```
gcaccagcgc ctcatccggg ctgcnatctt ggt                                    333
```

```
<210> SEQ ID NO 49
<211> LENGTH: 317
<212> TYPE: DNA
<213> ORGANISM: Homo sapiens
<220> FEATURE:
<221> NAME/KEY: Unsure
<222> LOCATION: 26
<223> OTHER INFORMATION: May be any nucleotide
<220> FEATURE:
<221> NAME/KEY: Unsure
<222> LOCATION: 78
<223> OTHER INFORMATION: May be any nucleotide
<220> FEATURE:
<221> NAME/KEY: Unsure
<222> LOCATION: 114
<223> OTHER INFORMATION: May be any nucleotide
<220> FEATURE:
<221> NAME/KEY: Unsure
<222> LOCATION: 222
<223> OTHER INFORMATION: May be any nucleotide
<220> FEATURE:
<221> NAME/KEY: Unsure
<222> LOCATION: 279
<223> OTHER INFORMATION: May be any nucleotide
<220> FEATURE:
<221> NAME/KEY: Unsure
<222> LOCATION: 297
<223> OTHER INFORMATION: May be any nucleotide

<400> SEQUENCE: 49
cagcctcctc ctcctaggat gacctnaccc tccagctctc cagttttcag gttggagaca       60
ttagatggag gccaaganga tggctctgag gcggacagag gaaagctgga tttngggagc      120
gggctgcctc ccatggagtc acagttccag ggcgaggacc ggaaattcgc ccctcagata      180
agagtcaacc tcaactaccg aaaggaacag gtgccagtca gncggatcca aaccgatttg      240
accgagatcg gctcttcaat gcggtctccc tggggtgtnc ccgaaggatc ttggctngac      300
tttcagagta cctgagc                                                    317
```

```
<210> SEQ ID NO 50
<211> LENGTH: 379
<212> TYPE: DNA
<213> ORGANISM: Homo sapiens

<400> SEQUENCE: 50
aatggcgatg tgcagagcgc tgtggcctcg gtaatagtca tctgtgcact gggcatttac       60
caggggctga ggattgccag agtcccggtc gatctgcagc agtggcagaa tgcaggcatt      120
gaccccgtcc ttaaggttca gcacagcctt catcaggcac gtcttacctg tggagccctc      180
tgtgtattcc gagtcggtga ggtacttgct gggtcttgct cagggtactc tgggaagtcc      240
agccagatcc tcgggacac cccggggagg accgcattga aggagccgat ctcgggtcaa       300
atcggtttgg gatccgggct gactgggcac ctgttccctt tcggtagttg agggttgact      360
cttaatctga gggggcga                                                   379
```

```
<210> SEQ ID NO 51
<211> LENGTH: 357
<212> TYPE: DNA
<213> ORGANISM: Homo sapiens
<220> FEATURE:
<221> NAME/KEY: Unsure
<222> LOCATION: 313
<223> OTHER INFORMATION: May be any nucleotide
<220> FEATURE:
```

<221> NAME/KEY: Unsure
<222> LOCATION: 329
<223> OTHER INFORMATION: May be any nucleotide
<220> FEATURE:
<221> NAME/KEY: Unsure
<222> LOCATION: 338
<223> OTHER INFORMATION: May be any nucleotide

<400> SEQUENCE: 51

```
aatggcgatg tgcagagcgc tgtggcctcg gtaatagtca tctgtgcact gggcatttac    60
caggggctga ggattgccag agtcccggtc gatctgcagc agtggcagaa tgcaggcatt   120
gaccccgtcc ttaaggttca gcacagcctt catcaggcac gtcttacctg tgggagccct   180
ctgtgtattc cgagtcggtg aggtacttgc tggtcttgct caggtactct gggaagtcca   240
gccagatcct cggggacacc ccggggagac cgcattgaag gagccgatct tcgggtcaaa   300
tcggttttgg atnccggctg acttggcanc tgtttccntt tcggtagttt gaggttg      357
```

<210> SEQ ID NO 52
<211> LENGTH: 463
<212> TYPE: DNA
<213> ORGANISM: Homo sapiens

<400> SEQUENCE: 52

```
ctcccctgt tagtgtcatc cctagtgctg ggctggctga acctgcttta ttatacacgt    60
ggctttcagc acacaggcat ctacagtgtc atgatccaaa aggtcattct gcgagacctg   120
ctccgcttcc tgctggtcta cctagtcttc cttttcggct ttgctgtagc cctagtaagc   180
ttgagccggg acggccgaag tcccaaagcc cctgaagata gcaacaccac tgtgacggaa   240
aagcccacgc tgggtcagga ggaggagcca gtcccatatg ggggcattct ggatgctccc   300
tagagctgtt caagttcacc attggtatgg gtgagctggc tttccaggaa cagctgcctt   360
tcgtggggtg gtgctgctgt tgctgttggc ctacgtcctc ctcacctacg tcctactgct   420
caacatgctc attgccctca tgagtgagac tgtcaacagc gtt                    463
```

<210> SEQ ID NO 53
<211> LENGTH: 354
<212> TYPE: DNA
<213> ORGANISM: Homo sapiens
<220> FEATURE:
<221> NAME/KEY: Unsure
<222> LOCATION: 290
<223> OTHER INFORMATION: May be any nucleotide
<220> FEATURE:
<221> NAME/KEY: Unsure
<222> LOCATION: 311
<223> OTHER INFORMATION: May be any nucleotide
<220> FEATURE:
<221> NAME/KEY: Unsure
<222> LOCATION: 318
<223> OTHER INFORMATION: May be any nucleotide

<400> SEQUENCE: 53

```
aatggcgatg tgcagaggct gtggcctcgg taatagtcat ctgtgcactg ggcatttacc    60
aggggctgag gattgccaga gtcccggtcg atctgcagca gtggcagaat gcaggcattg   120
accccgtcct taaggttcag cacagccttc atcaggcacg tcttacctgt gggagccctc   180
tgtgtattcc gagtcggtga ggtacttgct ggtcttgctc aggtactctg gaagtccagc   240
cagatcctcg ggacaaccc gggaggaccg cattgaagga gccgattttn ggtcaaaatc   300
gggtttggat nccggttnat ttgggaaccg tttccctttt gggtagtttt aggg         354
```

<210> SEQ ID NO 54
<211> LENGTH: 275
<212> TYPE: DNA
<213> ORGANISM: Homo sapiens
<220> FEATURE:
<221> NAME/KEY: Unsure
<222> LOCATION: 16
<223> OTHER INFORMATION: May be any nucleotide
<220> FEATURE:
<221> NAME/KEY: Unsure
<222> LOCATION: 230
<223> OTHER INFORMATION: May be any nucleotide
<220> FEATURE:
<221> NAME/KEY: Unsure
<222> LOCATION: 244
<223> OTHER INFORMATION: May be any nucleotide
<220> FEATURE:
<221> NAME/KEY: Unsure
<222> LOCATION: 263
<223> OTHER INFORMATION: May be any nucleotide

<400> SEQUENCE: 54
agaggtcctg gctggnaccg agcagcctcc tcctcctagg atgacctcac cctccagctc    60
tccagttttc aggttggaga cattagatgg aggccaagaa gatggctctg aggcggacag   120
aggaaagctg gattttggga gcgggctgcc tcccatggag tcacagttcc agggcgagga   180
ccggaaattc gcccctcaga taagagtcaa cctcaactac cgaaagggan caggtgccag   240
taanccgggt ccaaaccgat ttnaccaaga tcggg                              275

<210> SEQ ID NO 55
<211> LENGTH: 256
<212> TYPE: DNA
<213> ORGANISM: Homo sapiens

<400> SEQUENCE: 55
aatggcgatg tgcagacgct gtggcctcgg taatagtcat ctgtgcactg ggcatttacc    60
aggggctgag gattgccaga gtccctgtcg atctgcagca gtggcagaat gtaggcattg   120
actccgtcct taaggttcag cacagccttc atcaggcacg tcttacctgt ggagccctct   180
gtgtattccg agtcggtgag gtacttgctg gtcttgctca ggtactctgg aagtccagcc   240
agatcctcgg ggacac                                                   256

<210> SEQ ID NO 56
<211> LENGTH: 220
<212> TYPE: DNA
<213> ORGANISM: Homo sapiens

<400> SEQUENCE: 56
acgagggcaa cggggcccag tacaggggta tcctggtagc ctccttggag ctcttcaaat    60
tcaccatcgg catgggcgag ctggccttcc aggagcagct gcacttccgc ggcatggtgc   120
tgctgctgct gctggcctac gtgctgctca cctacatcct gctgctcaac atgctcatcg   180
ccctcatgag cgagaccgtc aacagtgtcg ccactgacag                         220

<210> SEQ ID NO 57
<211> LENGTH: 444
<212> TYPE: DNA
<213> ORGANISM: Homo sapiens
<220> FEATURE:
<221> NAME/KEY: Unsure
<222> LOCATION: 6
<223> OTHER INFORMATION: May be any nucleotide
<220> FEATURE:
<221> NAME/KEY: Unsure
<222> LOCATION: 374

```
<223> OTHER INFORMATION: May be any nucleotide
<220> FEATURE:
<221> NAME/KEY: Unsure
<222> LOCATION: 412
<223> OTHER INFORMATION: May be any nucleotide
<220> FEATURE:
<221> NAME/KEY: Unsure
<222> LOCATION: 423
<223> OTHER INFORMATION: May be any nucleotide
<220> FEATURE:
<221> NAME/KEY: Unsure
<222> LOCATION: 431
<223> OTHER INFORMATION: May be any nucleotide

<400> SEQUENCE: 57
tagttngtga aaatatatat ttgccaccag aattcactgg gacccccagag ccagcagatg      60 tggttggaaa gatcctctgc tctgtcctct ggcctcctgc tgcatctggg ccatcagttg     120
gactggagga gctggacggg cacatagttt tcctcagagg caccatcctc atcctccttg     180 ggagggaag ccaggacagg gttctcgaga gttcctgtaa acagatggca agcactgtag     240 cttaacccctt gagtgtgtcc ccaggaagca ggcaccaggg aaacgggcc acagtcatga     300 aaacacgtca tgccgtgggg acagcctcag cgatcctggg aggccagcaa tccttctccc     360 tgcttcctc actncacaag catttcccaa tcccttgcc atatccaggg gntttcccct     420
tgnccccttt ncaccctcaa gggg                                            444

<210> SEQ ID NO 58
<211> LENGTH: 200
<212> TYPE: DNA
<213> ORGANISM: Homo sapiens
<220> FEATURE:
<221> NAME/KEY: Unsure
<222> LOCATION: 192
<223> OTHER INFORMATION: May be any nucleotide

<400> SEQUENCE: 58
gtgagttagt gaaaatatat atttgccacc agaattcact gggacccccag agccagcaga     60 tgtggttgga aagatcctct gctctgtcct ctggcctcct gctgcatctg gccatcagt    120 tggactggag gagctggacg ggcacatagt tttcctcaga ggcaccatcc tcatcctcct    180
tgggagggga anccaggacg                                                 200

<210> SEQ ID NO 59
<211> LENGTH: 369
<212> TYPE: DNA
<213> ORGANISM: Homo sapiens
<220> FEATURE:
<221> NAME/KEY: Unsure
<222> LOCATION: 27
<223> OTHER INFORMATION: May be any nucleotide
<220> FEATURE:
<221> NAME/KEY: Unsure
<222> LOCATION: 50
<223> OTHER INFORMATION: May be any nucleotide
<220> FEATURE:
<221> NAME/KEY: Unsure
<222> LOCATION: 191
<223> OTHER INFORMATION: May be any nucleotide
<220> FEATURE:
<221> NAME/KEY: Unsure
<222> LOCATION: 225
<223> OTHER INFORMATION: May be any nucleotide
<220> FEATURE:
<221> NAME/KEY: Unsure
<222> LOCATION: 241
<223> OTHER INFORMATION: May be any nucleotide
<220> FEATURE:
<221> NAME/KEY: Unsure
```

```
<222> LOCATION: 271
<223> OTHER INFORMATION: May be any nucleotide
<220> FEATURE:
<221> NAME/KEY: Unsure
<222> LOCATION: 328
<223> OTHER INFORMATION: May be any nucleotide
<220> FEATURE:
<221> NAME/KEY: Unsure
<222> LOCATION: 350
<223> OTHER INFORMATION: May be any nucleotide
<220> FEATURE:
<221> NAME/KEY: Unsure
<222> LOCATION: 355
<223> OTHER INFORMATION: May be any nucleotide
<220> FEATURE:
<221> NAME/KEY: Unsure
<222> LOCATION: 364
<223> OTHER INFORMATION: May be any nucleotide

<400> SEQUENCE: 59
agagccagca gatgtggttg gaaagancct ctgctctgtc ctctggcctn ctgctgcatc    60
tgggccatca gttggactgg aggagctgga cgggcacata gttttcctca gaggcaccat   120
cctcatcctc cttgggaggt gaagccagga cagggttctc gagagttcct gtaaacagat   180
ggcaagcact ntagcttaac ccttgagtgt gtccccagga agcangcacc agggaaacgg   240
ngccacagtc atgaaaacac gtcatgccgt ngggacagcc tcagcgatcc tggaaggcca   300
gcaatccttc tccctgcttc cctcactnca caaggcattt cccaatcccn tgccntttca   360 gggnttttc                                                          369

<210> SEQ ID NO 60
<211> LENGTH: 322
<212> TYPE: DNA
<213> ORGANISM: Homo sapiens
<220> FEATURE:
<221> NAME/KEY: Unsure
<222> LOCATION: 17
<223> OTHER INFORMATION: May be any nucleotide
<220> FEATURE:
<221> NAME/KEY: Unsure
<222> LOCATION: 70
<223> OTHER INFORMATION: May be any nucleotide
<220> FEATURE:
<221> NAME/KEY: Unsure
<222> LOCATION: 108
<223> OTHER INFORMATION: May be any nucleotide
<220> FEATURE:
<221> NAME/KEY: Unsure
<222> LOCATION: 109
<223> OTHER INFORMATION: May be any nucleotide
<220> FEATURE:
<221> NAME/KEY: Unsure
<222> LOCATION: 113
<223> OTHER INFORMATION: May be any nucleotide
<220> FEATURE:
<221> NAME/KEY: Unsure
<222> LOCATION: 116
<223> OTHER INFORMATION: May be any nucleotide
<220> FEATURE:
<221> NAME/KEY: Unsure
<222> LOCATION: 120
<223> OTHER INFORMATION: May be any nucleotide
<220> FEATURE:
<221> NAME/KEY: Unsure
<222> LOCATION: 127
<223> OTHER INFORMATION: May be any nucleotide
<220> FEATURE:
<221> NAME/KEY: Unsure
<222> LOCATION: 131
<223> OTHER INFORMATION: May be any nucleotide
<220> FEATURE:
<221> NAME/KEY: Unsure
<222> LOCATION: 133
```

```
<223> OTHER INFORMATION: May be any nucleotide
<220> FEATURE:
<221> NAME/KEY: Unsure
<222> LOCATION: 226
<223> OTHER INFORMATION: May be any nucleotide
<220> FEATURE:
<221> NAME/KEY: Unsure
<222> LOCATION: 295
<223> OTHER INFORMATION: May be any nucleotide
<220> FEATURE:
<221> NAME/KEY: Unsure
<222> LOCATION: 317
<223> OTHER INFORMATION: May be any nucleotide

<400> SEQUENCE: 60
gggaagaatc cccatcnatg gcagcttcca tgggtggcaa gtcccagca tccaagggct      60 gcctctgagn gtcacccacc cccacctgag accttagtgg ctagaatnng ganggntggn   120
ggtggancct nantcgcagc agggtgtgtc cagatggtca gtctctggtg gctagcctgt   180
cctgacaggg gagagttaag ctcccgctct ccaccgtgcc ggctgncaga gtgggctgag   240
ggtgaccgag agaccagaac ctgcttgctg gagcttagtg ctcagagctg gggangggagg   300 ttccgccgct cctctgntgt ca                                             322

<210> SEQ ID NO 61
<211> LENGTH: 155
<212> TYPE: DNA
<213> ORGANISM: Homo sapiens
<220> FEATURE:
<221> NAME/KEY: Unsure
<222> LOCATION: 33
<223> OTHER INFORMATION: May be any nucleotide

<400> SEQUENCE: 61
aaccctgtcc tggcttcccc tcccaaggag gantgaggat ggtgcctctg aggaaaacta    60
tgtgcccgtc cagctcctcc agtccaactg atggcccaga tgcagcagga ggccagagga   120
cagagcagag gatctttcca accacatctg ctggc                              155

<210> SEQ ID NO 62
<211> LENGTH: 144
<212> TYPE: DNA
<213> ORGANISM: Homo sapiens

<400> SEQUENCE: 62
aattcactgg gacccagag ccagcagatg tggttggaaa gatcctctgc tctgtcctct     60
ggcctcctgc tgcatctggg ccatcagttg gactggagga gctggacggg cacatagttt   120
tcctcagagg caccatcctc atcc                                          144

<210> SEQ ID NO 63
<211> LENGTH: 144
<212> TYPE: DNA
<213> ORGANISM: Homo sapiens

<400> SEQUENCE: 63
actgggaccc cagagccagc agatgtggtt ggaaagatcc tctgctctgt cctctggcct    60
cctgctgcat ctgggccatc agttggactg gaggtgctgg acgggcacat agttttcctc   120
agaggcacca tcctcatcct tctt                                          144

<210> SEQ ID NO 64
<211> LENGTH: 310
<212> TYPE: DNA
<213> ORGANISM: Mus musculus
```

<400> SEQUENCE: 64

```
gagaatggtt actggtggtg caggaggaaa aggcatcgcg cagggaggct gctgaaagtt      60
ggcaccaaag gggatggtat acctgatgag cgctggtgct tcagggtgga ggaagtaaac     120
tgggctgcat gggagaagac ccttcccacc ttatctgagg atccatcagg ggcaggcatc     180
actggttata aaagaaccc aacctctaaa cctgggaaga acagtgcctc agaggaagac     240
catctgcctc ttcaggtcct ccagtcccac tgacggtcca gatgcggcac agcaggctgg     300
cagggtagag                                                            310
```

<210> SEQ ID NO 65
<211> LENGTH: 334
<212> TYPE: DNA
<213> ORGANISM: Mus musculus

<400> SEQUENCE: 65

```
ggaaaaggca tccgcaggga ggctgctgaa agttggcacc aaagggatg gtatacctga      60
tgagcgctgg tgcttcaggg tggaggaagt aaactgggct gcatgggaga agacccttcc     120
caccttatct gaggatccat caggggcagg catcactggt tataaaaga acccaacctc     180
taaacctggg aagaacagtg cctcagagga agaccatctg cctcttcagg tcctccagtc     240
ccactgacgg tccagatgcg gcacagcagg ctggcagggt agagtaggga atttgccag     300
ccacacccga ggctactgaa ttttggtgga aata                                 334
```

<210> SEQ ID NO 66
<211> LENGTH: 447
<212> TYPE: DNA
<213> ORGANISM: Mus musculus

<400> SEQUENCE: 66

```
ttcggatcca tgcccgagag aacaccaacg tctgtcacca agatgtacga cctgctgctt      60
ctcaagtgtt cacgcctctt ccccgccagc aacctggaga cagttctcaa caatgatggc     120
ctttcgcctc tcatgatggc tgccaagaca ggcaagatcg ggtctttca gcacatcatc     180
cgacgtgagg tgacagatga ggacacccgg catctgtctc gcaagttcaa ggactgggcc     240
tatgggcctg tgtattcttc tctctacgac ctctcctccc tggacacatg cggggaggag     300
gtgtccgtgc tggagatcct ggtgtacaac agcaagatcg agaaccgcca tgagatgctg     360
gctgtagagc cattaacgaa ctgttgagag acaagtggcg taagtttggg gctgtgtcct     420
tctacatcaa cgtggtctcc tatctgt                                         447
```

<210> SEQ ID NO 67
<211> LENGTH: 431
<212> TYPE: DNA
<213> ORGANISM: Homo sapiens

<400> SEQUENCE: 67

```
tcgcccctca gataagagtc aacctcaact accgaaagga acaggtgcca gtcagccgga      60
tccaaaccga tttgaccgag atcggctctt caatgcggtc tcccggggtg tcccgaggat     120
ctggctggac ttccagagta cctgagcaag accagcaagt acctcaccga ctcggaatac     180
acagagggct ccacaggtaa gacgtgcctg atgaaggctg tgctgaacct taaggacggg     240
gtcaatgcct gcattctgcc actgctgcag atcgaccggg actctggcaa tcctcagccc     300
ctggtaaatg cccagtgcac agatgactat taccgaggcc acagcgctct gcacatcgcc     360
```

-continued

```
attgagaaga ggagtctgca gtgtgtgaag ctcctggtgg agaatggggc caatgtgcat    420
gcccgggcct g                                                         431
```

Vanilloid Receptor-2

```
  1 GCAGATGGTCAGTCTCTGGTGGCTAGCCTGTCCTGACAGGGGAGAGTTAAGCTCCCGTTC  60
  1     M  V  S  L  W  W  L  A  C  P  D  R  G  E  L  S  S  R  S   19

61 TCCACCGTGCCGGCTGGCCAGGTGGGCTGAGGGTGACCGAGAGACCAGAACCTGCTTGCT 120
 20  P  P  C  R  L  A  R  W  A  E  G  D  R  E  T  R  T  C  L  L   39

121 GGAGCTTAGTGCTCAGAGCTGGGGAGGGAGGTTCCGCCGCTCCTCTGCTGTCAGCACCGG 180
 40  E  L  S  A  Q  S  W  G  G  R  F  R  R  S  S  A  V  S  T  G   59

181 CAGCCCCTCCCGGCTTCACTTCCTCCCGCAGCCCCTGCTACTGAGAAGCTCCGGGATCCC 240
 60  S  P  S  R  L  H  F  L  P  Q  P  L  L  L  R  S  S  G  I  P   79

241 AGCAGCCGCCACGCCCTGGCCTCAGCCTGCGGGGCTCCAGTCAGGCCAACACCGACGCGC 300
 80  A  A  A  T  P  W  P  Q  P  A  G  L  Q  S  G  Q  H  R  R  A   99

301 ACGTGGGAGGAAGACAGGACCCTTGACATCTCCATCTGCACAGAGGTCCTGGCTGGACCG 360
100  R  G  R  K  T  G  P  L  T  S  P  S  A  Q  R  S  W  L  D  R  119

361 AGCTATGCCTCCTCCTCCTAGGATGACCTCACCCTCCAGCTCTCCAGTTTTCAGGTTGGA 420
120  A  M  P  P  P  P  R  M  T  S  P  S  S  S  P  V  F  R  L  E  139

421 GACATTAGATGGAGGCCAAGAAGATGGCTCTGAGGCGGACAGAGGAAAGCTGGATTTTGG 480
140  T  L  D  G  G  Q  E  D  G  S  E  A  D  R  G  K  L  D  F  G  159

481 GAGCGGGCTGCCTCCCATGGAGTCACAGTTCCAGGGCGAGGACCGGAAATTCGCCCCTCA 540
160  S  G  L  P  P  M  E  S  Q  F  Q  G  E  D  R  K  F  A  P  Q  179

541 GATAAGAGTCAACCTCAACTACCGAAAGGGAACAGGTGCCAGTCAGCCGGATCCAAACCG 600
180  I  R  V  N  L  N  Y  R  K  G  T  G  A  S  Q  P  D  P  N  R  199

601 ATTTGACCGAGATCGGCTCTTCAATGCGGTCTCCCGGGGTGTCCCCGAGGATCTGGCTGG 660
200  F  D  R  D  R  L  F  N  A  V  S  R  G  V  P  E  D  L  A  G  219

661 ACTTCCAGAGTACCTGAGCAAGACCAGCAAGTACCTCACCGACTCGGAATACACAGAGGG 720
220  L  P  E  Y  L  S  K  T  S  K  Y  L  T  D  S  E  Y  T  E  G  239
```

FIG.1A

```
 721 CTCCACAGGTAAGACGTGCCTGATGAAGGCTGTGCTGAACCTTAAGGACGGGGTCAATGC  780
 240  S  T  G  K  T  C  L  M  K  A  V  L  N  L  K  D  G  V  N  A  259

781 CTGCATTCTGCCACTGCTGCAGATCGACCGGGACTCTGGCAATCCTCAGCCCCTGGTAAA  840
 260  C  I  L  P  L  L  Q  I  D  R  D  S  G  N  P  Q  P  L  V  N  279

841 TGCCCAGTGCACAGATGACTATTACCGAGGCCACAGCGCTCTGCACATCGCCATTGAGAA  900
 280  A  Q  C  T  D  D  Y  Y  R  G  H  S  A  L  H  I  A  I  E  K  299

901 GAGGAGTCTGCAGTGTGTGAAGCTCCTGGTGGAGAATGGGGCCAATGTGCATGCCCGGGC  960
 300  R  S  L  Q  C  V  K  L  L  V  E  N  G  A  N  V  H  A  R  A  319

961 CTGCGGCCGCTTCTTCCAGAAGGGCCAAGGGACTTGCTTTTATTTCGGTGAGCTACCCCT 1020
 320  C  G  R  F  F  Q  K  G  Q  G  T  C  F  Y  F  G  E  L  P  L  339

1021 CTCTTTGGCCGCTTGCACCAAGCAGTGGGATGTGGTAAGCTACCTCCTGGAGAACCCACA 1080
 340  S  L  A  A  C  T  K  Q  W  D  V  V  S  Y  L  L  E  N  P  H  359

1081 CCAGCCCGCCAGCCTGCAGGCCACTGACTCCCAGGGCAACACAGTCCTGCATGCCCTAGT 1140
 360  Q  P  A  S  L  Q  A  T  D  S  Q  G  N  T  V  L  H  A  L  V  379

1141 GATGATCTCGGACAACTCAGCTGAGAACATTGCACTGGTGACCAGCATGTATGATGGGCT 1200
 380  M  I  S  D  N  S  A  E  N  I  A  L  V  T  S  M  Y  D  G  L  399

1201 CCTCCAAGCTGGGGCCCGCCTCTGCCCTACCGTGCAGCTTGAGGACATCCGCAACCTGCA 1260
 400  L  Q  A  G  A  R  L  C  P  T  V  Q  L  E  D  I  R  N  L  Q  419

1261 GGATCTCACGCCTCTGAAGCTGGCCGCCAAGGAGGGCAAGATCGAGATTTTCAGGCACAT 1320
 420  D  L  T  P  L  K  L  A  A  K  E  G  K  I  E  I  F  R  H  I  439

1321 CCTGCAGCGGGAGTTTTCAGGACTGAGCCACCTTTCCCGAAAGTTCACCGAGTGGTGCTA 1380
 440  L  Q  R  E  F  S  G  L  S  H  L  S  R  K  F  T  E  W  C  Y  459

1381 TGGGCCTGTCCGGGTGTCGCTGTATGACCTGGCTTCTGTGGACAGCTGTGAGGAGAACTC 1440
 460  G  P  V  R  V  S  L  Y  D  L  A  S  V  D  S  C  E  E  N  S  479
```

FIG.1B

```
1441 AGTGCTGGAGATCATTGCCTTTCATTGCAAGAGCCCGCACCGACACCGAATGGTCGTTTT 1500
 480  V  L  E  I  I  A  F  H  C  K  S  P  H  R  H  R  M  V  V  L  499

1501 GGAGCCCCTGAACAAACTGCTGCAGGCGAAATGGGATCTGCTCATCCCCAAGTTCTTCTT 1560
 500  E  P  L  N  K  L  L  Q  A  K  W  D  L  L  I  P  K  F  F  L  519

1561 AAACTTCCTGTGTAATCTGATCTACATGTTCATCTTCACCGCTGTTGCCTACCATCAGCC 1620
 520  N  F  L  C  N  L  I  Y  M  F  I  F  T  A  V  A  Y  H  Q  P  539

1621 TACCCTGAAGAAGGCCGCCCCTCACCTGAAAGCGGAGGTTGGAAACTCCATGCTGCTGAC 1680
 540  T  L  K  K  A  A  P  H  L  K  A  E  V  G  N  S  M  L  L  T  559

1681 GGGCCACATCCTTATCCTGCTAGGGGGGATCTACCTCCTCGTGGGCCAGCTGTGGTACTT 1740
 560  G  H  I  L  I  L  L  G  G  I  Y  L  L  V  G  Q  L  W  Y  F  579

1741 CTGGCGGCGCCACGTGTTCATCTGGATCTCGTTCATAGACAGCTACTTTGAAATCCTCTT 1800
 580  W  R  R  H  V  F  I  W  I  S  F  I  D  S  Y  F  E  I  L  F  599

1801 CCTGTTCCAGGCCCTGCTCACAGTGGTGTCCCAGGTGCTGTGTTTCCTGGCCATCGAGTG 1860
 600  L  F  Q  A  L  L  T  V  V  S  Q  V  L  C  F  L  A  I  E  W  619

1861 GTACCTGCCCCTGCTTGTGTCTGCGCTGGTGCTGGGCTGGCTGAACCTGCTTTACTATAC 1920
 620  Y  L  P  L  L  V  S  A  L  V  L  G  W  L  N  L  L  Y  Y  T  639

1921 ACGTGGCTTCCAGCACACAGGCATCTACAGTGTCATGATCCAGAAGGTCATCCTGCGGGA 1980
 640  R  G  F  Q  H  T  G  I  Y  S  V  M  I  Q  K  V  I  L  R  D  659

1981 CCTGCTGCGCTTCCTTCTGATCTACTTAGTCTTCCTTTTTCGGCTTCGCTGTAGCCCTGGT 2040
 660  L  L  R  F  L  L  I  Y  L  V  F  L  F  G  F  A  V  A  L  V  679

2041 GAGCCTGAGCCAGGAGGCTTGGCGCCCCGAAGCTCCTACAGGCCCCAATGCCACAGAGTC 2100
 680  S  L  S  Q  E  A  W  R  P  E  A  P  T  G  P  N  A  T  E  S  699

2101 AGTGCAGCCCATGGAGGGACAGGAGGACGAGGGCAACGGGGCCCAGTACAGGGGTATCCT 2160
 700  V  Q  P  M  E  G  Q  E  D  E  G  N  G  A  Q  Y  R  G  I  L  719
```

FIG. 1C

```
2161 GGAAGCCTCCTTGGAGCTCTTCAAATTCACCATCGGCATGGGCGAGCTGGCCTTCCAGGA 2220
 720    E  A  S  L  E  L  F  K  F  T  I  G  M  G  E  L  A  F  Q  E  739

2221 GCAGCTGCACTTCCGCGGCATGGTGCTGCTGCTGCTGCTGGCCTACGTGCTGCTCACCTA 2280
 740    Q  L  H  F  R  G  M  V  L  L  L  L  L  A  Y  V  L  L  T  Y  759

2281 CATCCTGCTGCTCAACATGCTCATCGCCCTCATGAGCGAGACCGTCAACAGTGTCGCCAC 2340
 760    I  L  L  L  N  M  L  I  A  L  M  S  E  T  V  N  S  V  A  T  779

2341 TGACAGCTGGAGCATCTGGAAGCTGCAGAAAGCCATCTCTGTCCTGGAGATGGAGAATGG 2400
 780    D  S  W  S  I  W  K  L  Q  K  A  I  S  V  L  E  M  E  N  G  799

2401 CTATTGGTGGTGCAGGAAGAAGCAGCGGGCAGGTGTGATGCTGACCGTTGGCACTAAGCC 2460
 800    Y  W  W  C  R  K  K  Q  R  A  G  V  M  L  T  V  G  T  K  P  819

2461 AGATGGCAGCCCCGATGAGCGCTGGTGCTTCAGGGTGGAGGAGGTGAACTGGGCTTCATG 2520
 820    D  G  S  P  D  E  R  W  C  F  R  V  E  E  V  N  W  A  S  W  839

2521 GGAGCAGACGCTGCCTACGCTGTGTGAGGACCCGTCAGGGGCAGGTGTCCCTCGAACTCT 2580
 840    E  Q  T  L  P  T  L  C  E  D  P  S  G  A  G  V  P  R  T  L  859

2581 CGAGAACCCTGTCCTGGCTTCCCCTCCCAAGGAGGATGAGGATGGTGCCTCTGAGGAAAA 2640
 860    E  N  P  V  L  A  S  P  P  K  E  D  E  D  G  A  S  E  E  N  879

2641 CTATGTGCCCGTCCAGCTCCTCCAGTCCAACTGATGGCCCAGATGCAGCAGGAGGCCAGA 2700
 880    Y  V  P  V  Q  L  L  Q  S  N  *                          890

2701 GGACAGAGCAGAGGATCTTTCCAACCACATCTGCTGGCTCTGGGGTCCCAGTGAATTCTG 2760

2761 GTGGCAAATATATATTTTTCACTAACTCAAAAAAAAAAAAAAAAAAA 2805
```

```
241  TGKTCLMKAVLNLKDEVNACILPLQIDRDSGNPQPLVNAQCTDDYYRGHSALHIAIEKR  VR2.prot
153  TGKTCLKAMLNLHNGQNDTIALLDVARKTDSLKQFVNASYTDSYYKQTALHIAIERR   VR1prot 301  SLQCVKLLVENGANVHARACERFFQKGQ-TCFYFGELPLSLAACTKQWDVVSYLLENPH  VR2.prot
213  NMTLVTLLVENGADVQAANGDFFKKTKGRPGFYFGELPLSLAACTNQLAIVKFLLQNSW  VR1prot 360  QPASLQATDSQGNTVLHALVMISDNSAENIALVTSMYDGLLQAGARLCPTVQLEDIRNLQ  VR2.prot
273  QPADISARDSVGNTVLHALVEVADNTVDNTKFVTSMYNEILILGAKLHPTLKLEEITNRK  VR1prot 420  DLTPLKLAAKEGKIEIFRHILQREFSGLS--HLSRKFTEWCYGPVRVSLYDLASVDSCEE  VR2.prot
333  GLTPLALAASSGKIGVLAYILQREIHEPECRHLSRKFTEWAYGPVHSSLYDLSCIDTCEK  VR1prot
```

FIG.2B

```
478  NSVLEIIAFHCK-SPHRHMVVLEPLNKLLQAKWDLLIPK-FFLNFLCNLIYMFIFTAVA  VR2.prot
393  NSVLEVIAYSSSETPNRHDLLLVEPLNRLLQDKWDRFVKRIFYFNFFVYCLYMIFTAAA  VRlprot 536  YHQPTLKKAAPHLKAEVGNSMLLTGHILLLGGIYLLVGQLWYFWRRHVFIWISFIDSYF  VR2.prot
453  YRPVEGLPPYKLKNTVGDYFRVTGEILSVSGGVFFFRGIQYFLQRRPSLKSLFVDSYS  VRlprot 596  EILFFQALLTVSQVLCFLAIEWLPLLVSALVLGWLLLYYTRGFQHTGIYSVMIQKV  VR2.prot
513  EILFFVQSLFMLVSVLYFSQRKEYVASMVFSLAMGWTNMLYYTRGFQQMGIYAVMIEKM  VRlprot 656  ILRDLLRFLLIYLVFLFGFAVALVSLSQEAWRPEAPTGPNATESVQPMEGQEDEGNGAQV  VR2.prot
573  ILRDLCRFMFVYLVFLFGFSTAVVTLIEDGKNNSLPMESTPHKCRGS----ACKPENSV  VRlprot
```

FIG.2C

```
716 R G I L E A S L E L F K F T I G M G E L A F Q E Q L H F R G M V L L L L A Y V L L T Y I L L L N M L I A L M S E T V N   VR2.prot
628 N S L Y S T C L E L F K F T I G M G D L E F T E N Y D F K A V F I I L L L A Y V I L T Y I L L L N M L I A L M G E T V N   VR1prot 776 S V A T D S W S I W K L Q K A I S V L E M E N G Y W C R K K Q - R A G V M L T V G T K P D G S P D E R W C F R V E E V   VR2.prot
688 K I A Q E S K N I W K L Q R A I T I L D T E K S F L K C M R K A F R S E K L L Q V E F T P D E K D D Y R W C F R V D E V   VR1prot 835 N A S W E Q T L P T L C E D P S G - A G V P R T L E - - - - - - - - - - - - N P V L A S P P K E D E D G A   VR2.prot
748 N W T T N V G I I N E D P G N C E G V K R T L S F S L R S G R V S G R N W K N F A L V P L L R D A S T R D R H A T   VR1prot 876 S E E N - - - - - - - - - - - - - - Y V P V Q L L Q S N   VR2.prot
808 Q Q E E V Q L K H Y T G S L K P E D A E V F K D S M V P G E K   VR1prot
```

FIG.2D

VANILLOID RECEPTOR-2

The present application hereby claims priority benefit to U.S. appl. Ser. No. 60/040,163, filed Mar. 7, 1997, which is herein incorporated by reference; and the present application is a continuation-in-part of PCT/US98/04493, filed Mar. 6, 1998, which is herein incorporated by reference.

BACKGROUND OF THE INVENTION

1. Field of the Invention

The present invention relates to a novel member of the vanilloid receptor family. More specifically, the present invention relates to the discovery, identification and characterization of nucleotides that encode vanilloid receptor-2 (VR2), a receptor having homology with the rat vanilloid receptor-1 protein. The invention encompasses VR2 polynucleotides, host cell expression systems, VR2 polypeptides (including fragments, variants, derivatives and analogs thereof), VR2 fusion proteins, antibodies to VR2, agonists and antagonists of VR2, and other compounds that modulate VR2 gene expression or VR2 activity, that can be used for diagnosis, drug screening, and treatment or prevention of disorders which include, but are not limited to, chronic pain syndromes, congenital pain insensitivity, inflammation, ischemia, host defense dysfunction, immune surveillance dysfunction, arthritis, multiple sclerosis, autoimmunity, immune dysfunction, and allergy.

2. Related Art

The concentration of free $Ca^{+2}$ in the cytosol of any cell is extremely low ($\approx 10^{-7}$ M), whereas the concentration of free $Ca^{+2}$ in the extracellular fluid ($\approx 10^{-3}$ M) and in the endoplasmic reticulum is quite high. Thus, there is a large gradient tending to drive $Ca^{+2}$ into the cytosol across both the plasma membrane and the endoplasmic reticulum membrane. When a signal transiently opens $Ca^{+2}$ channels in either of these membranes, $Ca^{+2}$ rushes into the cytosol, dramatically increasing the local $Ca^{+2}$ concentration and triggering $Ca^{+2}$-responsive proteins in the cell. $Ca^{+2}$ has been demonstrated to act as an intracellular messenger in a wide variety of cellular responses, such as, for example, transmission of an action potential in nerve cells, muscular contraction, and cell secretion, activation, survival, proliferation, migration, and differentiation.

Pain is initiated when a subgroup of sensory neurons, called nociceptors, are activated by noxious chemical, thermal or mechanical stimuli. The activated nociceptors convey information regarding the noxious stimuli to pain processing centers in the spinal cord and brain (Fields, H., *Pain* (McGraw-Hill, New York, 1987). Nociceptors are characterized in part, by their sensitivity to vanilloids (i.e., chemicals containing vanillyl groups), such as, for example, capsaicin, the main pungent ingredient in capsaicin peppers. In mammals, exposure of nociceptor terminals to capsaicin leads to excitation of the neuron and the consequent perception of pain and local release of inflammatory mediators. Prolonged exposure of nociceptor terminals to capsaicin leads to the desensitization of these neurons to capsaicin and other noxious stimuli (Szolcsanyi, Y., in *Capsaicin and the Study of Pain* (ed. Wood J.) 255–272 (Academic, London, 1993). This phenomenon of desensitization has led to the use of capsaicin as an analgesic agent in the treatment of painful disorders ranging from viral and diabetic neuropathies to rheumatoid arthritis (Campbell, E., in *Capsaicin and the Study of Pain* (ed. Wood J.) 255–272 (Academic, London, 1993; Szallasi et al., *Pain* 68:195–208 (1996)).

Recently, a cDNA encoding vanilloid receptor subtype-1 (VR1), has been isolated from a rodent dorsal root ganglion plasmid cDNA library (Caterina et al., *Nature* 389:816–824 (1997). This clone encodes a polytopic integral membrane protein containing six transmembrane domains, four extracellular domains, four intracellular domains, and an additional short hydrophobic region between transmembrane domains five and six that may contribute to an ion permeation path (Hardie et al., *Trends Neurosci.* 16:371–376 (1993)). The product of this clone is a calcium permeable, non-selective cation channel that is structurally related to members of the TRP family of ion channels (see, e.g., Montell et al., *Neuron* 2:1313–1333 (1989); and Hardie et al., *Trends Neurosci.* 16:371–376 (1993)).

Capsaicin binding to VR1 has been demonstrated to trigger an increase in intracellular free calcium. Additionally, transfection of VR1 into non-neuronal cells has been shown to induce cytotoxicity upon continuous exposure to capsaicin. These observations are consistent with necrotic cell death resulting from excessive ion influx.

VR1 is activated (i.e., the VR1 cation-selective channel is opened), by capsaicin, capsaicin agonists, and other vanilloid compounds (e.g., resiniferatoxin), and antagonized by capsaicin antagonists (e.g., capsazepine and ruthenium red). Further, hydrogen ions potentiate the response of VR1 to low concentrations of capsaicin: thus, VR1 may be involved in the detection of noxious stimuli that accompany such conditions as inflammation and ischemia (Caterina et al, *Nature* 389:819–824 (1997).

Additionally, VR1 is activated when ambient temperatures are elevated to elicit pain in humans or pain associated behaviors in animals, indicating that, in addition to its role in transducing noxious chemical stimuli, VR1 functions as a transducer of painful thermal stimuli in vivo (Caterina et al., *Nature* 389:816–824 (1997).

The involvement of a vanilloid receptor family member in transducing thermal and chemical stimuli suggests that members of this family of cation channels are involved in diverse human disease states ranging from congenital pain insensitivity, to chronic pain syndromes and more generally that members of this family mediate cellular responses such as cell secretion, activation, survival, proliferation, migration and differentiation; that vanilloid receptor family members provide an important model system for the in vitro study of hyperalgesia; and that vanilloid receptors provide defined targets for the development of new analgesic agents.

SUMMARY OF THE INVENTION

The present invention provides isolated nucleic acid molecules comprising polynucleotides encoding a VR2 receptor having the amino acid sequence shown in FIGS. 1A–1D (SEQ ID NO:2) or the amino acid sequence encoded by the cDNA clone encoding the VR2 receptor deposited in a vector as ATCC Deposit Number 263082 on Jul. 30, 1998. The present invention also relates to recombinant vectors, which include the isolated nucleic acid molecules of the present invention, and to host cells containing the recombinant vectors, as well as to methods of making such vectors and host cells and for using them or other genetically modified host cells to produce VR2 polypeptides (including fragments, variants, derivatives, and analogs thereof) by recombinant techniques.

The invention further provides isolated VR2 polypeptides having amino acid sequences encoded by the polynucleotides described herein.

The present invention also provides a screening method for identifying compounds capable of eliciting a cellular response induced by VR2, which involves contacting cells which express VR2 with the candidate compound, assaying a cellular response (e.g., ion flux, such as, $Ca^{+2}$ flux), and comparing the cellular response to a standard cellular response, the standard being assayed in absence of the candidate compound; whereby, an increased cellular response over the standard indicates that the compound is an agonist.

The present invention also provides a screening method for identifying compounds capable of enhancing or inhibiting a cellular response induced by VR2 receptors, which involves contacting cells which express VR2 receptors with the candidate compound in the presence of a VR2 agonist (e.g., a vanilloid compound, such as capsaicin) or other stimulus (e.g., thermal stimuli), assaying a cellular response (e.g., ion flux, such as, $Ca^{+2}$ flux), and comparing the cellular response to a standard cellular response, the standard being assayed when contact is made between the agonist and VR2 or when VR2 is exposed to the stimulus, in absence of the candidate compound; whereby, an increased cellular response over the standard indicates that the compound is an agonist and a decreased cellular response over the standard indicates that the compound is an agonist In another embodiment, a screening assay for agonists and antagonists is provided which involves determining the effect a candidate compound has on the binding of cellular ligands (e.g., vanilloid compounds, such as, capsaicin) to VR2. In particular, the method involves contacting VR2 with a ligand or other stimulus (e.g., thermal stimuli) and a candidate compound and determining whether ligand binding to the VR2 receptors is increased or decreased due to the presence of the candidate compound.

The invention further provides a diagnostic method useful during diagnosis or prognosis of disease states resulting from aberrant pain sensitivity, or aberrant cell secretion, activation, survival, migration, differentiation and/or proliferation, due to alterations in VR2 coding sequences and/or receptor expression.

An additional embodiment of the invention is related to a method for treating an individual in need of an increased level of VR2 activity in the body comprising administering to such an individual a composition comprising a therapeutically effective amount of VR2 polypeptides or polynucleotides of the invention or a VR2 agonist.

A still further embodiment of the invention is related to a method for treating an individual in need of a decreased level of a VR2 receptor activity in the body comprising, administering to such an individual a composition comprising a therapeutically effective amount of VR2 polypeptides or polynucleotides of the invention a VR2 antagonist.

The invention additionally provides soluble forms of the polypeptides of the present invention. Soluble peptides are defined by amino acid sequences wherein the sequence comprises the polypeptide sequence lacking a transmembrane domain (e.g., VR2 polypeptide fragments corresponding to intracellular and/or extracellular domains). Such soluble forms of the VR2 receptor are useful as antagonists of the membrane bound forms of the receptor.

BRIEF DESCRIPTION OF THE FIGURES

FIGS. 1A–D show the nucleotide sequence (SEQ ID NO:1) and deduced amino acid sequence (SEQ ID NO:2) of the VR2 receptor. The deduced complete amino acid sequence includes 889 amino acid residues and has a deduced molecular weight of about 99,765 Da. The predicted domains of the VR2 polypeptide are: N-terminal intracellular domain 1 (amino acid residues M-1 to about N-520 of SEQ ID NO:2), ankyrin repeat domain 1 (within N-terminal intracellular domain; amino acid residues from about R-288 to about C-320 of SEQ ID NO:2), ankyrin repeat domain 2 (within N-terminal intracellular domain; amino acid residues from about F-334 to about A-366 of SEQ ID NO:2), ankyrin repeat domain 3 (within N-terminal intracellular domain; amino acid residues from about Q-419 to about H-449 of SEQ ID NO:2), transmembrane domain 1 (amino acid residues from about F-517 to about H-537 of SEQ ID NO:2); extracellular domain 1 (amino acid residues from about Q-538 to about I-562 of SEQ ID NO:2), transmembrane domain 2 (amino acid residues from about L-563 to about Y-578 of SEQ ID NO:2); intracellular domain 2 (amino acid residues from about F-579 to about D-592 of SEQ ID NO:2), transmembrane domain 3 (amino acid residues from about S-593 to about F-614 of SEQ ID NO:2); extracellular domain 2 (amino acid residues from about L-615 to about V-625 of SEQ ID NO:2), transmembrane domain 4 (amino acid residues from about S-626 to about I-652 of SEQ ID NO:2); intracellular domain 3 (amino acid residues from about Q-653 to about D-659 of SEQ ID NO:2), transmembrane domain 5 (amino acid residues from about L-660 to about V-679 of SEQ ID NO:2); extracellular domain 3 (amino acid residues from about S-680 to about N-711 of SEQ ID NO:2), pore loop (amino acid residues from about G-712 to about G-733 of SEQ ID NO:2), extracellular domain 4 (amino acid residues from about E-734 to about H-742 of SEQ ID NO:2), transmembrane domain 6 (amino acid residues from about F-743 to about S-771 of SEQ ID NO:2); and C-terminal intracellular domain 4 (amino acids from about E-772 to about N-889 of SEQ ID NO:2). The transmembrane domains are underscored.

FIGS. 2A–2D show the regions of similarity between the amino acid sequences of the VR2 receptor protein of FIGS. 1A–1D (labeled VR2.prot; SEQ ID NO:2) and rat vanilloid receptor subtype 1 protein (SEQ ID NO:3) which is labeled "VR1prot" (GenBank Accession Number 2570933 (AF029310)). Identical amino acid residues between VR1 and VR2 are shaded.

DETAILED DESCRIPTION OF THE PREFERRED EMBODIMENTS

Figure 2A:
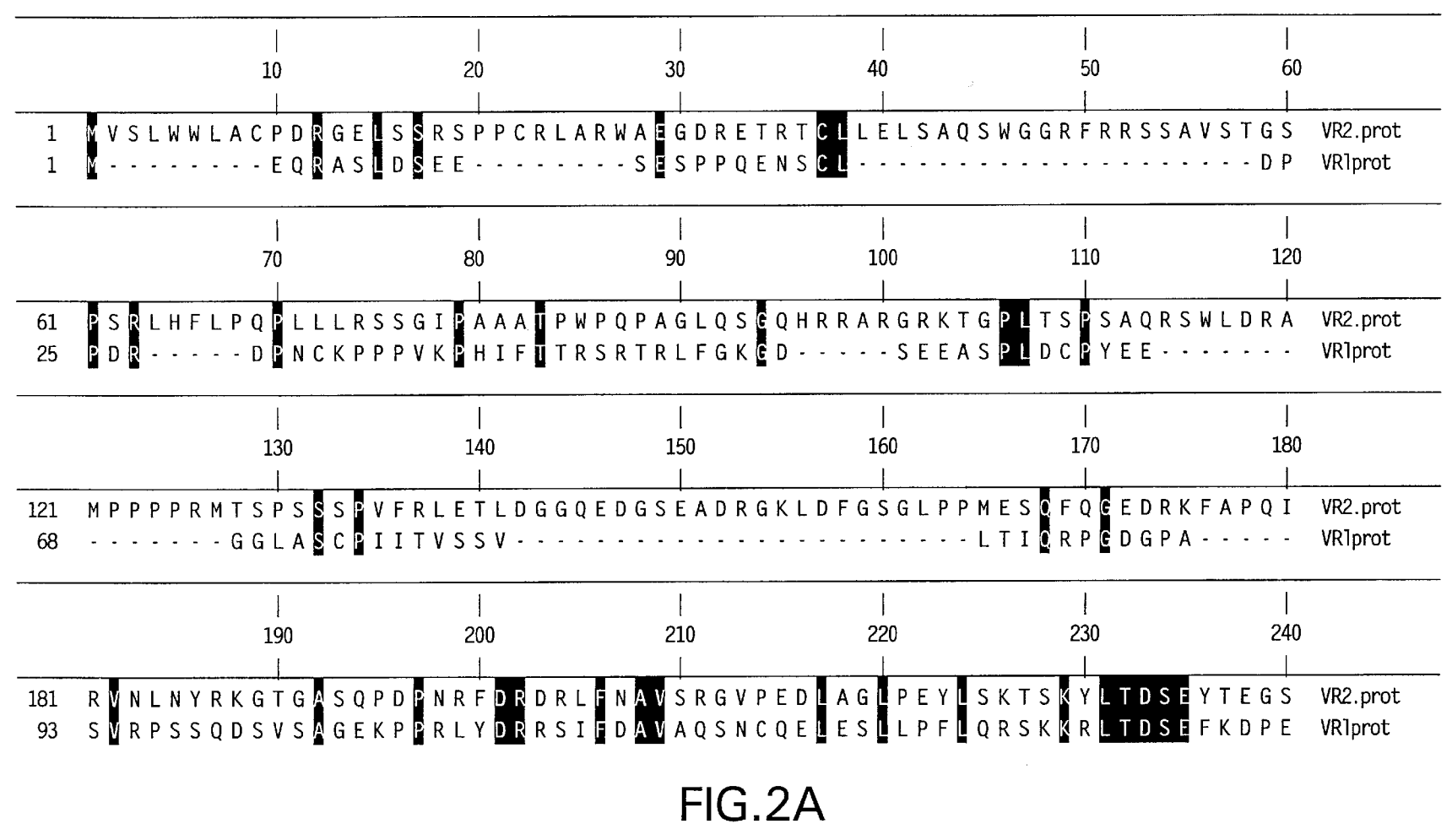
Figure 3:
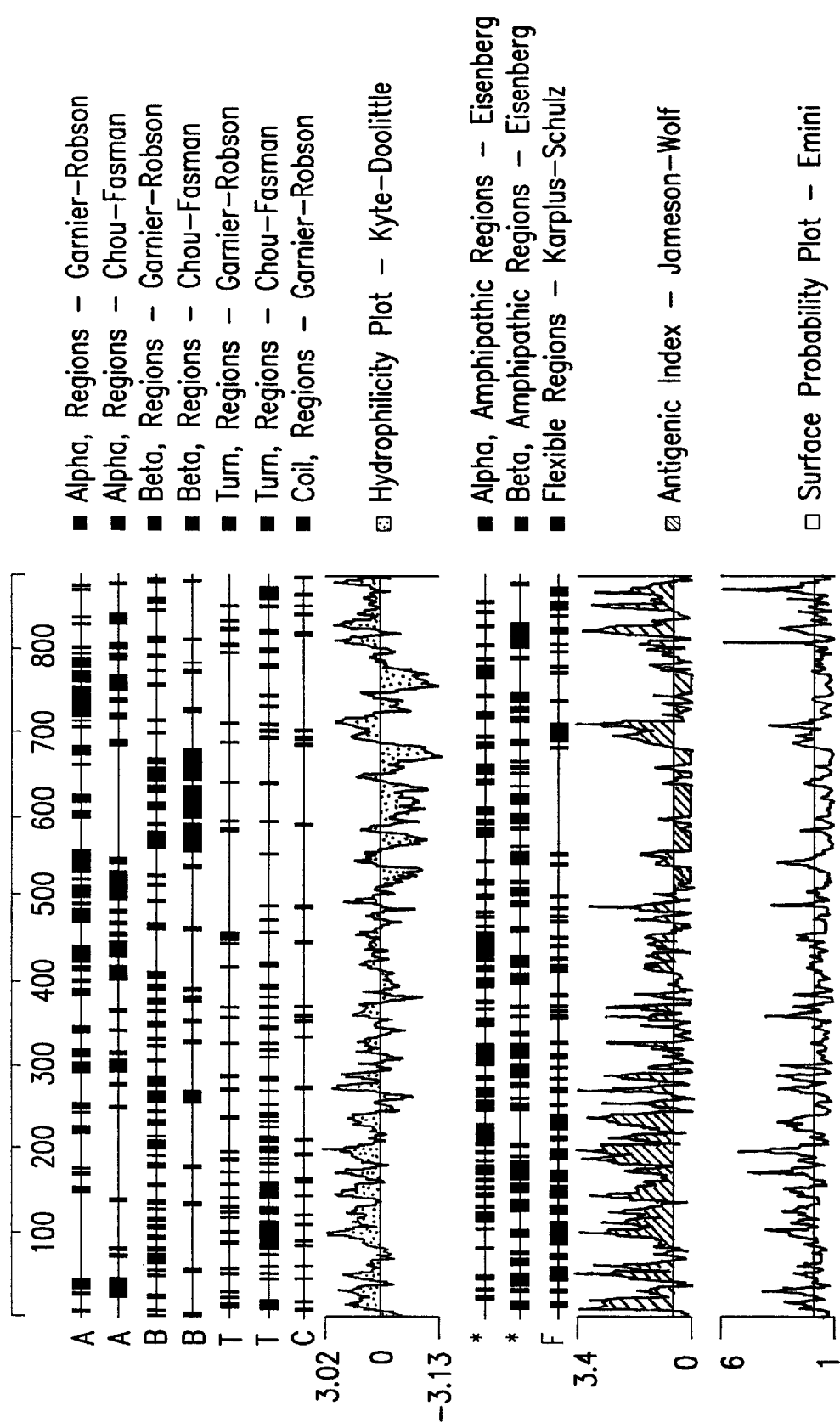
FIG. 3 shows a structural analysis of the VR2 receptor amino acid sequence of FIGS. 1A–1D (SEQ ID NO:2), generated using the default parameters of the recited computer programs. Alpha, beta, turn and coil regions; hydrophilicity and hydrophobicity; amphipathic regions; flexible regions; antigenic index and surface probability are shown. In the "Antigenic Index-Jameson-Wolf" graph, amino acid residues: C-9 to L-24; from A-28 to C-37, from W-46 to H-65, from T-83 to P-134; from E-139 to P-178; from R-181 to N-207; from V-209 to G-219; from E-222 to L-246; from L-251 to N-258; from Q-266 to P-274; from T-283 to S-291; from 1-297 to Q-303; from V-309 to A-313; from R-318 to T-330; from C-344 to D-349; from L-355 to A-362; from Q-365 to N-372; from S-382 to E-387; from Q-411 to E-434; from R-442 to G-446; from L-450 to T-455; from A-470 to V-480; from C-488 to R-495; from P-539 to N-554; from E-684 to Q-714; from R-804 to A-809; from G-816 to E-833; and from E-840 to Y-880 as depicted in FIGS. 1A–1D (SEQ ID NO:2) correspond to the shown highly antigenic regions of the VR2 receptor protein.

The present invention provides isolated nucleic acid molecules comprising polynucleotides encoding a VR2 polypeptide (FIGS. 1A–1D (SEQ ID NO:2)), the amino acid sequence of which was determined by sequencing a cloned cDNA (Clone HMAJ106). The VR2 protein shown in FIGS. 1A–1D shares sequence homology with rat vanilloid receptor subtype 1 (FIGS. 2A–2D (SEQ ID NO:3)). The nucleotide sequence shown in FIGS. 1A–1D (SEQ ID NO:1) was obtained by sequencing a cDNA clone (Clone HMAJI06). On Jul. 30, 1998, the plasmid corresponding to this clone was deposited with the American Type Culture Collection, 10801 University Blvd, Manassas, Va., 20110-2209, and was assigned accession number 263052. The deposited cDNA is contained in the UniZAP XR plasmid (Stratagene, La Jolla, Calif.).

As used herein, "VR2 protein", "VR2 receptor", "receptor protein", "VR2", and "VR2 polypeptide" refer to all polypeptides resulting from the alternate splicing of the genomic DNA sequences encoding proteins having regions of amino acid sequence identity and receptor activity which correspond to the protein shown in FIGS. 1A–1D (SEQ ID NO:2). The VR2 protein shown in FIGS. 1A–1D is an example of such a receptor protein.

Nucleic Acid Molecule

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleotide sequence in FIGS. 1A–1D (SEQ ID NO: 1), nucleic acid molecules of the present invention encoding VR2 polypeptides may be obtained using standard cloning and screening procedures, such as those used for cloning cDNAs using MRNA as starting material. Northern analysis has revealed expression of the VR2 transcript in a variety of tissues, with highest levels in the spleen, lymph node, peripheral blood leukocytes, and lung; next highest levels of expression were observed in the thymus, heart, placenta, brain, bone marrow and fetal liver; and lower expression in other tissues. Thus, any of these tissues or cell types provide a source of VR2 mRNA. Additionally, any tissue or cell source may be utilized to routinely clone VR2 genomic DNA using techniques known in the art. Illustrative of the invention, the nucleic acid molecule described in FIGS. 1A–1D (SEQ ID NO:1) was discovered in a cDNA library derived from GM-CSF treated macrophages.

The determined nucleotide sequence of the VR2 cDNA of FIGS. 1A–1D (SEQ ID NO: 1) contains an open reading frame encoding a polytopic polypeptide of about 889 amino acid residues, with 4 intracellular domains, 6 transmembrane domains, 4 extracellular domains, and a pore loop, and having a deduced molecular weight of about 99,765 Da. The VR2 protein shown in FIGS. 1A–1D (SEQ ID NO:2) is predicted to be about 51% identical and about 60% similar to the rat VR1 protein depicted in SEQ ID NO:3 (see FIGS. 2A–2D) using the computer program "Bestfit" (see below). In addition to having homology, VR1 and VR2 share the same predicted topological organization. For example, like VR1, VR2 contains 4 intracellular and 4 extracellular domains, 6 transmembrane domains with a pore loop between transmembrane regions 5 and 6, and three ankyrin repeat motifs in the amino terminal hydrophilic domain. As discussed above, VR1 has been shown to be a cation selective heat and chemical activated ion channel in the pain pathway.

Nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand or complementary strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Isolated RNA molecules include in vivo or in vitro RNA transcripts of the DNA molecules of the present invention. Further examples of isolated DNA molecules include recombinant DNA molecules maintained in heterologous host cells or purified (partially or substantially) DNA molecules in solution. However, a nucleic acid contained in a clone that is a member of a library (e.g., a genomic or cDNA library) that has not been isolated from other members of the library (e.g., in the form of a homogeneous solution containing the clone and other members of the library) or which is contained on a chromosome preparation (e.g., a chromosome spread), is not "isolated" for the purposes of this invention. Isolated nucleic acid molecules according to the present invention may be produced naturally, recombinantly, or synthetically.

In one embodiment, nucleic acid molecules of the present invention include DNA molecules comprising an open reading frame (ORF) shown in FIGS. 1A–1D (SEQ ID NO:1); and DNA molecules which comprise a sequence substantially different from those described above, but which, due to the degeneracy of the genetic code, still encode the VR2 receptor polypeptide shown in FIGS. 1A–1D (SEQ ID NO:2). Of course, the genetic code is well known in the art. Thus, it would be routine for one skilled in the art to generate such degenerate variants.

In another embodiment, the invention provides isolated nucleic acid molecules encoding the VR2 polypeptide having the amino acid sequence encoded by the cDNA clone contained in the plasmid deposited as ATCC Deposit No. 203082 on Jul. 30, 1998. In a further embodiment, these nucleic acid molecules encode the full-length polypeptide lacking the N-terminal methionine (amino acid residues 2 to 889 of SEQ ID NO:2). The invention further provides isolated nucleic acid molecules having the nucleotide sequences shown in FIGS. 1A–1D (SEQ ID NO:1), the nucleotide sequence of the cDNA contained in the above-described deposited clone (clone HMAJI06); or nucleic acid molecules having a sequence complementary to one of the above sequences. Such isolated molecules, particularly DNA molecules, have uses that include, but are not limited to, probes for gene mapping by in situ hybridization with chromosomes, and for detecting expression of the VR2 genes of the present invention in human tissue, for instance, by Northern blot analysis.

The present invention is further directed to fragments of the isolated nucleic acid molecules (i.e. polynucleotides) described herein. By a fragment of an isolated nucleic acid molecule having, for example, the nucleotide sequence of the deposited cDNA (clone HMAJI06), a nucleotide sequence encoding the polypeptide sequence encoded by the deposited cDNA, a nucleotide sequence encoding the polypeptide sequence depicted in FIGS. 1A–1D (SEQ ID NO:2), the nucleotide sequence shown in FIGS. 1A–1D (SEQ ID NO:1), or the complementary strand thereto, is intended fragments at least 15 nt, and more preferably at least about 20 nt, still more preferably at least 30 nt, and even more preferably, at least about 40, 50, 100, 150, 200, 250, 300, 325, 350, 375, 400, 450, 500, 550, or 600 nt in length. These fragments have numerous uses which include, but are not limited to, diagnostic probes and primers as discussed herein. Of course, larger fragments, such as those of 501–1500 nt in length are also useful according to the present invention as are fragments corresponding to most, if not all, of the nucleotide sequences of the deposited cDNA (clone HMAJI06) or as shown in FIGS. 1A–1D (SEQ ID NO:1). By a fragment at least 20 nt in length, for example, is intended fragments which include 20 or more contiguous bases from, for example, the nucleotide sequence of the deposited cDNA, or the nucleotide sequence as shown in FIGS. 1A–1D (SEQ ID NO:1).

Representative examples of VR2 polynucleotide fragments of the invention include, for example, fragments that comprise, or alternatively, consist of, a sequence from about nucleotide 1 to 50, 51 to 100, 101 to 150, 151 to 200, 201 to 250, 251 to 300, 301 to 350, 351 to 400, 401 to 450, 451 to 500, 501 to 550, 551 to 600, 600 to 650, 651 to 700, 701 to 750, 751 to 800, 800 to 850, 851 to 900, 901 to 950, 951 to 1000, 1001 to 1050, 1051 to 1100, 1101 to 1150, 1151 to 1200, 1201 to 1250, 1251 to 1300, 1301 to 1350, 1351 to 1400, 1401 to 1450, 1451 to 1500, 1501 to 1550, 1551 to 1600, 1601 to 1650, 1651 to 1700, 1701 to 1750, 1751 to 1800, 1801 to 1850, 1851 to 1900, 1901 to 1950, 1951 to 2000, 2001 to 2050, 2051 to 2100, 2101 to 2150, 2151 to 2200, 2201 to 2250, 2251 to 2300, 2301 to 2350, 2351 to 2400, 2401 to 2450, 2451 to 2500, 2501 to 2550, 2551 to 2600, 2601 to 2650, 2651 to 2700, and/or 2701 to 2750, of SEQ ID NO:1, or the complementary strand thereto, or the cDNA contained in the deposited clone. In this context "about" includes the particularly recited ranges, larger or smaller by several (5, 4, 3, 2, or 1) nucleotides, at either terminus or at both termini.

In specific embodiments, the polynucleotide fragments of the invention comprise, or alternatively, consist of, a sequence from nucleotide 961 to 1000, 1730 to 1770, 1770 to 1800, and/or 1800 to 1840, of SEQ ID NO:1, or the complementary strand thereto.

Preferably, the polynucleotide fragments of the invention encode a polypeptide which demonstrates a VR2 functional activity. By a polypeptide demonstrating "functional activity" is meant, a polypeptide capable of displaying one or more known functional activities associated with a full-length VR2 polypeptide. Such functional activities include, but are not limited to, biological activity (e.g., ion flux (e.g, $Ca^{+2}$ flux)), antigenicity [ability to bind (or compete with a VR2 polypeptide for binding) to an anti-VR2 antibody], immunogenicity (ability to generate antibody which binds to a VR2 polypeptide), and ability to bind to a receptor or ligand for a VR2 polypeptide (e.g., a vanilloid compound (e.g., capsaicin, resiniferatoxin, and capsazepine)).

Preferred nucleic acid fragments of the invention include nucleic acid molecules encoding one or more VR2 receptor domains. In particular embodiments, such nucleic acid fragments comprise, or alternatively consist of, nucleic acid molecules encoding: a polypeptide selected from the group consisting of: (a) N-terminal intracellular domain 1 (amino acid residues M-1 to about N-520 of SEQ ID NO:2); (b) ankyrin repeat domain 1 (within N-terminal intracellular domain; amino acid residues from about R-288 to about C-320 of SEQ ID NO:2); (c) ankyrin repeat domain 2 (within N-terminal intracellular domain; amino acid residues from about F-334 to about A-366 of SEQ ID NO:2); (d) ankyrin repeat domain 3 (within N-terminal intracellular domain; (e) amino acid residues from about Q-419 to about H-449 of SEQ ID NO:2); (f) transmembrane domain 1 (amino acid residues from about F-517 to about H-537 of SEQ ID NO:2); (g) extracellular domain 1 (amino acid residues from about Q-538 to I-562 of SEQ ID NO:2); (h) transmembrane domain 2 (about L-563 to about Y-578 of SEQ ID NO:2); (i) intracellular domain 2 (amino acid residues from about F-579 to about D-592 of SEQ ID NO:2); (j) transmembrane domain 3 (amino acid residues from about S-593 to about F-614 of SEQ ID NO:2); (k) extracellular domain 2 (amino acid residues from about L-615 to about V-625 of SEQ ID NO:2); (l) transmembrane domain 4 (amino acid residues from about S-626 to about 1-652 of SEQ ID NO:2); (m) intracellular domain 3 (amino acid residues from about Q-653 to about D-659 of SEQ ID NO:2); (n) transmembrane domain 5 (amino acid residues from about L-660 to about V-679 of SEQ ID NO:2); (o) extracellular domain 3 (amino acid residues from about S-680 to about N-711 of SEQ ID NO:2); (p) pore loop (amino acid residues from about G-712 to about G-733 of SEQ ID NO:2); (q) extracellular domain 4 (amino acid residues from about E-734 to about H-742 of SEQ ID NO:2); (r) transmembrane domain 6 (amino acid residues from about F-743 to about S-771 of SEQ ID NO:2); (s) C-terminal intracellular domain 4 (amino acid residues from about E-772 to about N-889 of SEQ ID NO:2); (t) any combination of polypeptides (a)–(s); and (u) the complementary strand of the sense strand encoding any of polypeptides (a)–(s).

The amino acid residues constituting the extracellular, transmembrane and intracellular domains have been predicted by computer analysis. Thus, as one of ordinary skill would appreciate, the amino acid residues constituting these domains may vary slightly (e.g., by about 1 to about 15 amino acid residues) depending on the criteria used to define each domain.

Preferred nucleic acid fragments of the invention also include nucleic acid molecules encoding epitope-bearing portions of the VR2 receptor. In particular, such nucleic acid fragments of the present invention include nucleic acid molecules encoding: a polypeptide comprising, or alternatively consisting of, amino acid residues: from C-9 to L-24; from A-28 to C-37; from W-46 to H-65; from T-83 to P-134; from E-139 to P-178; from R-181 to N-207; from V-209 to G-219; from E-222 to L-246; from L-251 to N-258; from Q-266 to P-274; from T-283 to S-291; from I-297 to Q-303; from V-309 to A-313; from R-318 to T-330; from C-344 to D-349; from L-355 to A-362; from Q-365 to N-372; from S-382 to E-387; from Q-411 to E-434; from R-442 to G-446; from L-450 to T-455; from A-470 to V-480; from C-488 to R-495; from P-539 to N-554; from E-684 to Q-714; from R-804 to A-809; from G-816 to E-833; and/or from E-840 to Y-880 of SEQ ID NO:2. The inventors have determined that the above polypeptides are antigenic regions of the VR2 polypeptide. Methods for determining other such epitope-bearing portions of VR2 polypeptides are described in detail below.

In addition, the present inventors have identified the following cDNA clones related to portions of the sequence shown in SEQ ID NO: 1: HMSBA20R (SEQ ID NO:9); HAFAU18R (SEQ ID NO: 10); HJPAK91R (SEQ ID NO:11); HCETB29R (SEQ ID NO: 12); HBGBT42R (SEQ ID NO:13); HTOFC66R (SEQ ID NO: 14); HTPCA74R (SEQ ID NO: 15); HWABR13R (SEQ ID NO: 16) and HDPMS61R (SEQ ID NO:17). ID NO:60); GenBank Accession No. AA121981 (SEQ ID NO:61); GenBank Accession No. AA121980 (SEQ ID NO:62); GenBank Accession No. T12252 (SEQ ID NO:63); GenBank Accession No. AA015295 (SEQ ID NO:64); GenBank Accession No. AA274980 (SEQ ID NO:65); GenBank Accession No. AA139413 (SEQ ID NO:66); and GenBank Accession No. AA236416 (SEQ ID NO:67).

In another embodiment, the invention provides isolated nucleic acid molecules comprising polynucleotides which hybridize, preferably under stringent hybridization conditions, to a portion of one or more of the nucleic acids (i.e., polynucleotides) described herein, such as, for instance, the cDNA clone contained in ATCC Deposit 203082, the polynucleotide sequence depicted in FIGS. 1A–1D (SEQ ID NO: 1) or the complementary strand thereto, and/or any of the polynucleotide fragments as described herein. By "stringent hybridization conditions" is intended overnight incubation at 42° C. in a solution comprising: 50% formamide, 5×SSC (750 mM Nacl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C. By a polynucleotide which hybridizes to a "portion" of a polynucleotide is intended a polynucleotide (either DNA or RNA) hybridizing to at least 15 nucleotides (nt), and more preferably at least 20 nt, still more preferably at least 30 nt, and even more preferably 30–70, or 80–150 nt, or the entire length of the reference polynucleotide. By a portion of a polynucleotide of "at least 20 nt in length," for example, is intended 20 or more contiguous nucleotides from the nucleotide sequence of the reference polynucleotide (e.g., the deposited cDNA or the complementary strand of the nucleotide sequence shown in FIGS. 1A–1D (SEQ ID NO: 1)). Of course, a polynucleotide which hybridizes only to a poly A sequence (such as the 3' terminal poly(A) tail of a cDNA sequence), or to a complementary stretch of T (or U) residues, would not be included in a polynucleotide of the invention used to hybridize to a portion of a nucleic acid of the invention, since such a polynucleotide would hybridize to any nucleic acid molecule containing a The following public ESTs, which relate to portions of SEQ ID NO:1, have also been identified: GenBank Accession No. N29128 (SEQ ID NO:18); GenBank Accession No. AA741232 (SEQ ID NO: 19); GenBank Accession No. W44731 (SEQ ID NO:20); GenBank Accession No. N28029 (SEQ ID NO:21), GenBank Accession No. N35179 (SEQ ID NO:22); GenBank Accession No. AA768829 (SEQ ID NO:23); GenBank Accession No. H20025 (SEQ ID NO:24); GenBank Accession No. W38665 (SEQ ID NO:25), GenBank Accession No. AA281348 (SEQ ID NO:26), GenBank Accession No. W92895 (SEQ ID NO:27); GenBank Accession No. AA461295 (SEQ ID NO:28); GenBank Accession No. AA815110 (SEQ ID NO:29); GenBank Accession No. H20101 (SEQ ID NO:30); GenBank Accession No. N23395 (SEQ ID NO:31); GenBank Accession No. AA236417 (SEQ ID NO:32); GenBank Accession No. AA459710 (SEQ ID NO:33); GenBank Accession No. H51393 (SEQ ID NO:34); GenBank Accession No. H49128 (SEQ ID NO:35); GenBank Accession No. N26729 (SEQ ID NO:36); GenBank Accession No. N21167 (SEQ ID NO:37); GenBank Accession No. W92818 (SEQ ID NO:38); GenBank Accession No. H50404 (SEQ ID NO:39); GenBank Accession No. AA304033 (SEQ ID NO:40); GenBank Accession No. N34617 (SEQ ID NO:41); GenBank Accession No. H50364 (SEQ ID NO:42); GenBank Accession No. AA281349 (SEQ ID NO:43); GenBank Accession No. N24224 (SEQ ID NO:44); GenBank Accession No. AA357145 (SEQ ID NO:45); GenBank Accession No. W82502 (SEQ ID NO:46); GenBank Accession No. H99578 (SEQ ID NO:47); GenBank Accession no. N21284 (SEQ ID NO:48); GenBank Accession No. H51392 (SEQ ID NO:49); GenBank Accession No. H21490 (SEQ ID NO:50); GenBank Accession No. H49060 (SEQ ID NO:51); GenBank Accession No. AA476107 (SEQ ID NO:52); GenBank Accession No. H27879 (SEQ ID NO:53); GenBank Accession No. H40615 (SEQ ID NO:54); GenBank Accession No. AA814328 (SEQ ID NO:55); GenBank Accession No. T12251 (SEQ ID NO:56); GenBank Accession No. T71250 (SEQ ID NO:57); GenBank Accession No. H99192 (SEQ ID NO:58); GenBank Accession No. T90814 (SEQ ID NO:59); GenBank Accession No. N24475 (SEQ poly (A) stretch or the complement thereof (i.e., practically any double-stranded cDNA clone generated using oligo dT as a primer). These polynucleotides have uses which include, but are not limited to, diagnostic probes and primers as discussed above and in more detail below.

In specific embodiments, the nucleic acid molecules of the invention hybridize to the complementary strand of nucleotides 961 to 1000, 1730 to 1770, 1770 to 1800, and/or 1800 to 1840 of SEQ ID NO:1.

As indicated, nucleic acid molecules of the present invention which encode VR2 polypeptides may include, but are not limited to, those encoding the amino acid sequences of the full-length polypeptide (SEQ ID NO:2), by itself, the coding sequence for full-length polypeptide together with additional, non-coding sequences, including for example, but not limited to, introns and non-coding, 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities. Thus, the sequence encoding the polypeptides may be fused to a marker sequence, such as a sequence encoding a peptide which facilitates purification of the fused polypeptide. In certain preferred embodiments, the marker amino acid sequence is a hexa-histidine peptide, such as the tag provided in a pQE vector (Qiagen, Inc.), among others, many of which are commercially available. As described in Gentz et al., *Proc. Natl. Acad. Sci. USA* 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al, *Cell* 37:767 (1984). As discussed below, other such fusion proteins include the VR2 receptors fused to IgG-Fc at the N- or C-terminus.

The present invention further relates to variants of the nucleic acid molecules of the present invention, which encode fragments (i.e., portions), analogs or derivatives of the VR2 receptor. Variants may occur naturally, such as a natural allelic variant. By an "allelic variant" is intended one of several alternate forms of a gene occupying a given locus on a chromosome of an organism. Genes II, Lewin, B., ed., John Wiley & Sons, New York (1985). Non-naturally occurring variants may be produced using art-known mutagenesis techniques.

Such variants include those produced by nucleotide substitutions, deletions or additions, which may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the VR2 receptor or fragments thereof. Also especially preferred in this regard are conservative substitutions.

Further embodiments of the invention include isolated nucleic acid molecules comprising a polynucleotide having a nucleotide sequence at least 90% identical, and more preferably at least 95%, 96%, 97%, 98% or 99% identical to: (a) a nucleotide sequence encoding the VR2 polypeptide having the complete (i.e., full-length) amino acid sequence shown in FIGS. 1A–1D (SEQ ID NO:2); (b) a nucleotide encoding the complete amino sequence shown in FIGS. 1A–1D but lacking the N-terminal methionine (amino acid residues 2 to 889 in (SEQ ID NO:2)); (c) a nucleotide sequence encoding the VR2 polypeptide having the amino acid sequence encoded by the cDNA clone contained in ATCC Deposit Number 203082; (d) a nucleotide sequence encoding the VR2 polypeptide having the amino acid sequence encoded by the cDNA clone contained in ATCC Deposit Number 203082 but lacking the N-terminal methionine; (e) a nucleotide sequence encoding the N-terminal intracellular domain 1 of VR2 (amino acid residues M-1 to about N-520 of FIGS. 1A–1D (SEQ ID NO:2)); (f) a nucleotide sequence encoding ankyrin repeat domain 1 (within N-terminal intracellular domain; amino acid residues from about R-288 to about C-320 of FIGS. 1A–1D (SEQ ID NO:2)); (g) a nucleotide sequence encoding ankyrin repeat domain 2 (within N-terminal intracellular domain; amino acid residues from about F-334 to about A-366 of FIGS. 1A–1D (SEQ ID NO:2)); (h) a nucleotide sequence encoding ankyrin repeat domain 3 (within N-terminal intracellular domain; amino acid residues from about Q-419 to about H-449 of FIGS. 1A–1D (SEQ ID NO:2)); (i) a nucleotide sequence encoding transmembrane domain 1 (amino acid residues from about F-517 to about H-537 of FIGS. 1A–1D (SEQ ID NO:2)); (j) a nucleotide sequence encoding extracellular domain 1 (amino acid residues from about Q-538 to I-562 of FIGS. 1A–1D (SEQ ID NO:2)); (k) a nucleotide sequence encoding transmembrane domain 2 (amino acid residues from about L-563 to about Y-578 of FIGS. 1A–1D (SEQ ID NO:2)); (l) a nucleotide sequence encoding intracellular domain 2 (amino acid residues from about F-579 to about D-592 of FIGS. 1A–1D (SEQ ID NO:2)); (m) a nucleotide sequence encoding transmembrane domain 3 (amino acid residues from about S-593 to about F-614 of FIGS. 1A–D (SEQ ID NO:2)); (n) a nucleotide sequence encoding extracellular domain 2 (amino acid residues from about L-615 to about V-625 of FIGS. 1A–D (SEQ ID NO:2)); (o) a nucleotide sequence encoding transmembrane domain 4 (amino acid residues from about S-626 to about I-652 of FIGS. 1A–1D (SEQ ID NO:2)); (p) a nucleotide sequence encoding intracellular domain 3 (amino acid residues from about Q-653 to about D-659 of FIGS. 1A–1D (SEQ ID NO:2)); (q) a nucleotide sequence encoding transmembrane domain 5 (amino acid residues from about L-660 to about V-679 of FIGS. 1A–1D (SEQ ID NO:2)); (r) a nucleotide sequence encoding extracellular domain 3 (amino acid residues from about S-680 to about N-711 of FIGS. 1A–1D (SEQ ID NO:2)); (s) a nucleotide sequence encoding pore loop (amino acid residues from about G-712 to about G-733 of FIGS. 1A–1D; SEQ ID NO:2)); (t) a nucleotide sequence encoding extracellular domain 4 (amino acid residues from about E-734 to about H-742 of FIGS. 1A–1D (SEQ ID NO:2)); (u) a nucleotide sequence encoding transmembrane domain 6 (amino acid residues from about F-743 to about S-771 of FIGS. 1A–1D (SEQ ID NO:2)); (v) and a nucleotide sequence encoding the C-terminal intracellular domain 4 (amino acid residues from about E-772 to about N-889 of FIGS. 1A–1D (SEQ ID NO:2)); (w) any fragment described herein; (x) the polypeptide sequence of FIGS. 1A–1D (SEQ ID NO:2) minus a portion, or all of, one or more of the extracellular domains, transmembrane domains, intracellular domains, ankyrin repeat domains, and pore loop of the VR2 receptor shown in FIGS. 1A–1D (SEQ ID NO:2); and (y) a nucleotide sequence complementary to any of the nucleotide sequences in (a), (b), (c), (d), (e), (f), (g), (h), (i), (j), (k), (l), (m), (n), (o), (p), (q), (r), (s), (t), (u), (v), or (x).

By a polynucleotide having a nucleotide sequence at least, for example, 95% "identical" to a reference nucleotide sequence encoding a VR2 polypeptide is intended that the nucleotide sequence of the polynucleotide is identical to the reference sequence except that the polynucleotide sequence may include up to five point mutations per each 100 nucleotides of the reference nucleotide sequence encoding the VR2 receptor. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. The reference (query) sequence may be the entire VR2 encoding nucleotide sequence shown in FIGS. 1A–1D (SEQ ID NO:1) or any VR2 polynucleotide fragment as described herein.

As a practical matter, whether any particular nucleic acid molecule is at least 90%, 95%, 96%, 97%, 98% or 99% identical to, for instance, the encoding nucleotide sequence shown in FIGS. 1A–1D (SEQ ID NO:1), or to the nucleotide sequence of the deposited cDNA clone, can be determined conventionally using known computer programs such as the Bestfit program (Wisconsin Sequence Analysis Package, Version 8 for Unix, Genetics Computer Group, University Research Park, 575 Science Drive, Madison, Wis. 53711. Bestfit uses the local homology algorithm of Smith and Waterman, *Advances in Applied Mathematics* 2:482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al., *Comp. App. Biosci.* 6:237–245 (1990)). Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter. According to this embodiment, if the subject sequence is shorter than the query sequence because of 5' or 3' deletions, not because of internal deletions, a manual correction is made to the results to take into consideration the fact that the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. A determination of whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of this embodiment. Only bases outside the 5' and 3' bases of the subject sequence, as displayed by the FASTDB alignment, which are not matched/aligned with the query sequence, are calculated for the purposes of manually adjusting the percent identity score. For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for the purposes of this embodiment.

The present application is directed to nucleic acid molecules at least 90%, 95%, 96%, 97%, 98% or 99% identical to the nucleic acid sequences (i.e., polynucleotides) disclosed herein, irrespective of whether they encode a polypeptide having VR2 functional activity. This is because even where a particular nucleic acid molecule does not encode a polypeptide having VR2 functional activity, one of skill in the art would still know how to use the nucleic acid molecule, for instance, as a hybridization probe or a polymerase chain reaction (PCR) primer. Uses of the nucleic acid molecules of the present invention that do not encode a polypeptide having VR2 functional activity include, but are not limited to, inter alia, (1) isolating a VR2 receptor gene or allelic or splice variants thereof in a cDNA library; (2) in situ hybridization (e.g., "FISH") to metaphase chromosomal spreads to provide precise chromosomal location of a VR2 receptor gene, as described in Verma et al., *Human Chromosomes: A Manual of Basic Techniques*, Pergamon Press, New York (1988); and (3) Northern Blot analysis for detecting VR2 mRNA expression in specific tissues.

Preferred, however, are nucleic acid molecules having sequences at least 90%, 95%, 96%, 97%, 98% or 99% identical to the nucleic acid sequences disclosed herein, which do, in fact, encode a polypeptide having VR2 functional activity. By "a polypeptide having VR2 receptor functional activity" is intended polypeptides exhibiting activity similar, but not necessarily identical, to an activity of the VR2 receptors of the present invention (either the full-length polypeptide, or the splice variants), as measured, for example, in a particular immunoassay or biological assay. For example, VR2 activity can be measured by determining the ability of a VR2 polypeptide to bind a VR2 ligand (e.g., vanilloid compounds, such as, capsaicin) and/or to serve as a thermal and/or chemical activated cation (e.g., calcium) channel. VR2 receptor activity may also be measured by determining the ability of a polypeptide, such as cognate ligand which is free or expressed on a cell surface, to induce cation flux in cells expressing the polypeptide.

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNA, the nucleic acid sequence shown in FIGS. 1A–1D (SEQ ID NO:1), or fragments thereof, will encode polypeptides "having VR2 functional activity." In fact, since degenerate variants of any of these nucleotide sequences all encode the same polypeptide, in many instances, this will be clear to the skilled artisan even without performing the above described comparison assay. It will be further recognized in the art that, for such nucleic acid molecules that are not degenerate variants, a reasonable number will also encode a polypeptide having VR2 functional activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie et al., "Deciphering the Message in Protein Sequences: Tolerance to Amino Acid Substitutions," *Science* 247:1306–13 10 (1990), wherein the authors indicate that proteins are surprisingly tolerant of amino acid substitutions.

Vectors and Host Cells

The present invention also relates to vectors which include the isolated DNA molecules (i.e., polynucleotides) of the present invention, host cells which are genetically engineered with the recombinant vectors, and the production of VR2 polypeptides or fragments thereof using these host cells or host cells that have otherwise been genetically engineered using techniques known in the art to express a polypeptide of the invention.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

In one embodiment, the polynucleotide of the invention is operatively associated with an appropriate heterologous regulatory element (e.g., promoter or enhancer), such as the phage lambda PL promoter, the *E. coli* lac, trp and tac promoters, the SV40 early and late promoters and promoters of retroviral LTRs, to name a few. Other suitable promoters or enhancers will be known to the skilled artisan.

In embodiments in which vectors contain expression constructs, these constructs will further contain sites for transcription initiation, termination and, in the transcribed region, a ribosome binding site for translation. The coding portion of the mature transcripts expressed by the vector expression constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate heterologous hosts include, but are not limited to, bacterial cells, such as *E. coli*, Streptomyces and *Salmonella typhimurium* cells; fungal cells, such as yeast cells; insect cells such as Drosophila S2 and Spodoptera Sf9 cells; animal cells such as CHO, COS and Bowes melanoma cells; and plant cells. Appropriate culture mediums and conditions for the above-described host cells are known in the art.

Among vectors preferred for use in bacteria include pQE70, pQE60 and pQE-9, available from Qiagen; pHE4, pA2; and PO4, pBS vectors, Phagescript vectors, Bluescript vectors, pNH8A, pNH16a, pNH18A, pNH46A, available from Stratagene; and ptrc99a, pKK223-3, pKK233-3, pVR240, pRIT5 available from Pharmacia. Among preferred eukaryotic vectors are pWLNEO, pSV2CAT, pOG44, pXT1 and pSG available from Stratagene; pSVK3, pBPV, pMSG and pSVL available from Pharmacia. Other suitable vectors will be readily apparent to the skilled artisan.

Selection of appropriate vectors and promoters for expression in a host cell is a well known procedure and the requisite techniques for expression vector construction, introduction of the vector into the host and expression in the host are routine skills in the art.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., VR2 coding sequence), and/or to include genetic material (e.g., heterologous polynucleotide sequences) that is operably associated with VR2 polynucleotides of the invention, and which activates, alters, and/or amplifies endogenous VR2 polynucleotides. For example, techniques known in the art may be used to operably associate heterologous control regions (e.g., promoter and/or enhancer) and endogenous VR2 polynucleotide sequences via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., *Proc. Natl. Acad Sci. USA* 86:8932–8935 (1989); and Zijlstra et al., *Nature* 342:435–438 (1989), the disclosures of each of which are incorporated by reference in their entireties).

The host cell can be a higher eukaryotic cell, such as a mammalian cell (e.g., a human derived cell), or a lower eukaryotic cell, such as a yeast cell, or the host cell can be a prokaryotic cell, such as a bacterial cell. The host strain may be chosen which modulates the expression of the inserted gene sequences, or modifies and processes the gene product in the specific fashion desired. Expression from certain promoters can be elevated in the presence of certain inducers; thus expression of the genetically Engineered polypeptide may be controlled. Furthermore, different host cells have characteristics and specific mechanisms for the translational and post-translational processing and modification (e.g., glycosylation, phosphorylation, cleavage) of proteins. Appropriate cell lines can be chosen to ensure the desired modifications and processing of the foreign protein expressed.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

The polypeptide may be expressed in a modified form, such as a fusion protein (comprising the polypeptide joined via a peptide bond to a heterologous protein sequence (of a different protein)), and may include not only secretion signals, but also additional heterologous functional regions. Such a fusion protein can be made by ligating polynucleotides of the invention and the desired nucleic acid sequence encoding the desired amino acid sequence to each other, by methods known in the art, in the proper reading frame, and expressing the fusion protein product by methods known in the art. Alternatively, such a fusion protein can be made by protein synthetic techniques, e.g., by use of a peptide synthesizer. Thus, for instance, a region of additional amino acids, particularly charged amino acids, may be added to the N-terminus of the polypeptide to improve stability and persistence in the host cell, during purification, or during subsequent handling and storage. Additionally, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, human hIL-5 receptor have been fused with Fc portions for the purpose of high-throughput screening assays to identify antagonists of hIL-5. See, Bennett et al., *J. Mol. Recog.* 8:52–58 (1995) and Johanson et al., *J. Biol. Chem.* 270(16):9459–9471 (1995).

VR2 polypeptides (including fragments, variants, derivatives, and analogs thereof) can be recovered and purified from recombinant cell cultures by standard methods which include, but are not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated. or may be non-glycosylated. In addition, polypeptides of the invention may also include an initial modified methionine residue, or alternatively, may be missing the N-terminal methionine, in some cases as a result of host-mediated processes.

VR2 Polypeptides and Fragments

The invention further provides isolated VR2 polypeptides having the amino acid sequence encoded by the deposited cDNA (i.e., clone HMAJI06), the amino acid sequence depicted in FIGS. 1A–1D (SEQ ID NO:2), or a polypeptide comprising a fragment (i.e., portion) of the above polypeptides.

The polypeptides of the invention may be membrane bound or may be in a soluble circulating form. Soluble peptides are defined by amino acid sequence wherein the sequence comprises the polypeptide sequence lacking transmembrane domains.

The polypeptides of the present invention may exist as a membrane bound receptor having a transmembrane region and an intra- and extracellular region or they may exist in soluble form wherein a transmembrane domain is lacking. One example of such a form of the VR2 receptor is the full-length VR2 polypeptide shown in FIG. 1 (SEQ ID NO:2) which contains, transmembrane, intracellular and extracellular domains. Thus, this form of the VR2 polypeptide appears to be integrated in the plasma membrane of cells which express this polypeptide.

The polypeptides of the present invention are preferably provided in an isolated form. By "isolated polypeptide", is intended a polypeptide removed from its native environment. Thus, a polypeptide produced and contained within a recombinant host cell would be considered "isolated" for purposes of the present invention. Also intended as an "isolated polypeptide" are polypeptides that have been purified, partially or substantially, from a recombinant host. For example, recombinantly produced versions of the VR2 polypeptides can be substantially purified by the one-step method described in Smith and Johnson, *Gene* 67:31–40 (1988).

Polypeptide fragments of the present invention include polypeptides comprising or alternatively, consisting of, an amino acid sequence contained in SEQ ID NO:2, encoded by the cDNA contained in the deposited clone, or encoded by nucleic acids which hybridize (e.g., under stringent hybridization conditions) to the nucleotide sequence contained in the deposited clone, or shown in FIGS. 1A–1D (SEQ ID NO:1) or the complementary strand thereto. Protein fragments may be "free-standing," or comprised within a larger polypeptide of which the fragment forms a part or region, most preferably as a single continuous region. Representative examples of polypeptide fragments of the invention, include, for example, fragments that comprise or alternatively, consist of from about amino acid residues: 1 to 50, 51 to 100, 101 to 150, 151 to 200, 201 to 250, 251 to 300, 301 to 350, 321 to 333, 351 to 400, 401 to 450, 451 to 500, 501 to 550, 551 to 600, 576 to 606, 601 to 650, 651 to 700, 701 to 750, 751 to 800, 801 to 850 and/or 851 to 889 of SEQ ID NO:2. Moreover, polypeptide fragments can be at least 10, 20, 30, 40, 50, 60, 70, 80, 90, 100, 110, 120, 130, 140, 150, 175 or 200 amino acids in length.

In additional embodiments, the polypeptide fragments of the invention comprise, or alternatively consist, of one or more VR2 receptor domains. In particular embodiments, such polypeptide fragments comprise, or alternatively, consist of (a) N-terminal intracellular domain 1 (amino acid residues M-1 to about N-520 of SEQ ID NO:2); (b) ankyrin repeat domain 1 (within N-terminal intracellular domain; amino acid residues from about R-288 to about C-320 of SEQ ID NO:2); (c) ankyrin repeat domain 2 (within N-terminal intracellular domain, amino acid residues from about F-334 to about A-366 of SEQ ID NO:2); (d) ankyrin repeat domain 3 (within N-terminal intracellular domain; (e) amino acid residues from about Q-419 to about H-449 of SEQ ID NO:2); (f) transmembrane domain 1 (amino acid residues from about F-517 to about H-537 of SEQ ID NO:2); (g) extracellular domain 1 (amino acid residues from about Q-538 to I562 of SEQ ID NO:2); (h) transmembrane domain 2 (about L-563 to about Y-578 of SEQ ID NO:2); (i) intracellular domain 2 (amino acid residues from about F-579 to about D-592 of SEQ ID NO:2); (n) transmembrane domain 3 (amino acid residues from about S-593 to about F-614 of SEQ ID NO:2); (k) extracellular domain 2 (amino acid residues from about L-615 to about V-625 of SEQ ID NO:2); (l) transmembrane domain 4 (amino acid residues from about S-626 to about I652 of SEQ ID NO:2); (m) intracellular domain 3 (amino acid residues from about Q-653 to about D-659 of SEQ ID NO:2); (n) transmembrane domain 5 (amino acid residues from about L-660 to about V-679 of SEQ ID NO:2); (o) extracellular domain 3 (amino acid residues from about S-680 to about N-711 of SEQ ID NO:2); (p) pore loop (amino acid residues from about G-712 to about G-733 of SEQ ID NO:2); (q) extracellular domain 4 (amino acid residues from about E-734 to about H-742 of SEQ ID NO:2); (r) transmembrane domain 6 (amino acid residues from about F-743 to about S-771 of SEQ ID NO:2); (s) C-terminal intracellular domain 4 (amino acid residues from about E-772 to about N-889 of SEQ ID NO:2); or (t) any combination of polypeptides (a)–(s).

Among the especially preferred fragments of the invention are fragments characterized by structural or functional attributes of VR2. Such fragments include amino acid residues that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, surface forming regions, and high antigenic index regions (i.e., containing four or more contiguous amino acids having an antigenic index of greater than or equal to 1.5, as identified using the default parameters of the Jameson-Wolf program) of full-length VR2 (SEQ ID NO:2). Certain preferred regions are those set out in FIG. 3 and include, but are not limited to, regions of the aforementioned types identified by analysis of the amino acid sequence depicted in FIGS. 1A–1D (SEQ ID NO:2), such preferred regions include; Garnier-Robson predicted alpha-regions, beta-regions, turn-regions, and coil-regions; Chou-Fasman predicted alpha-regions, beta-regions, turn-regions, and coil-regions; Kyte-Doolittle predicted hydrophilic and hydrophobic regions; Eisenberg alpha and beta amphipathic regions; Emini surface-forming regions; and Jameson-Wolf high antigenic index regions, as predicted using the default parameters of these computer programs. Polynucleotides encoding these polypeptides are also encompassed by the invention.

In specific embodiments, polypeptide fragments of the invention comprise, or alternatively consist of, amino acid residues: 231 to 253, 289 to 297, 305 to 329, 321 to 332, 332 to 347, 370 to 385, 402 to 443, 576 to 590, 576 to 613, 590 to 599, 591 to 600, 600 to 613; 606 to 614, 637 to 654, 723 to 735, 772 to 798, and/or 804 to 839 as depicted in FIGS. 1A–1D (SEQ ID NO:2). Polynucleotides encoding these polypeptides are also encompassed by the invention.

The invention also provides polypeptides comprising epitope-bearing portions of the polypeptides of the invention. The epitopes of these polypeptide portions are an immunogenic or antigenic epitopes of the polypeptides described herein. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a polypeptide generally is less than the number of antigenic epitopes. See, for instance, Geysen et al., Proc. Natl. Acad. Sci. USA 81:3998–4002 (1983).

As to the selection of polypeptides bearing an antigenic epitope (i.e., that contain a region of a polypeptide to which an antibody can bind), it is well known in that art that relatively short synthetic polypeptides that mimic part of a polypeptide sequence are routinely capable of eliciting an antiserum that reacts with the partially mimicked polypeptide. See, for instance, Sutcliffe et al., Science 219:660–666 (1983). Polypeptides capable of eliciting protein-reactive sera are frequently represented in the primary sequence of a polypeptide, can be characterized by a set of simple chemical rules, and are confined neither to immunodominant regions of intact polypeptides (i.e., immunogenic epitopes) nor to the amino or carboxyl terminals.

Antigenic epitope-bearing polypeptides of the invention are therefore useful to raise antibodies, including monoclonal antibodies, that bind specifically to a polypeptide of the invention. See, for instance, Wilson et al., Cell 37:767–778 (1984) at 777. Antigenic epitope-bearing peptides and polypeptides of the invention preferably contain a sequence of at least four, at least seven, more preferably at least nine, and most preferably between at least about 15 to about 30 amino acids contained within the amino acid sequence of a polypeptide of the invention.

Non-limiting examples of antigenic polypeptides that can be used to generate VR2 receptor-specific antibodies include: a polypeptide comprising amino acid residues from: C-9 to L-24; from A-28 to C-37; from W-46 to H-65; from T-83 to P-134; from E-139 to P-178; from R-181 to N-207; from V-209 to G-219; from E-222 to L-246; from L-251 to N-258; from Q-266 to P-274; from T-283 to S-291; from I-297 to Q-303; from V-309 to A-313; from R-318 to T-330; from C-344 to D-349; from L-355 to A-362; from Q-365 to N-372; from S-382 to E-387; from Q-411 to E-434; from R-442 to G-446; from L-450 to T-455; from A-470 to V-480; from C-488 to R-495; from P-539 to N-554; from E-684 to Q-714; from R-804 to A-809; from G-816 to E-833; and from E-840 to Y-880, as depicted in FIGS. 1A–1D (SEQ ID NO:2). In a preferred embodiment, the polypeptide fragment of the invention comprises amino acid residues V-309 to A-313 as depicted in FIGS. 1A–1D (SEQ ID NO:2). In further preferred embodiments, polypeptide fragments of the invention compose 2, 3, 4, 5, 6, 7, 8, 9, 10, 15, or 20 of the above recited VR2 antigenic regions. As indicated above, the inventors have determined that the above polypeptide fragments are antigenic regions of the VR2 polypeptide.

The epitope-bearing peptides and polypeptides of the invention may be produced by any conventional means. Houghten, R. A. (1985) General method for the rapid solid-phase synthesis of large numbers of peptides: specificity of antigen-antibody interaction at the level of individual amino acids. Proc. Natl. Acad. Sci. USA 82:5131–5135. This "Simultaneous Multiple Peptide Synthesis (SMPS)" process is further described in U.S. Pat. No. 4,631,211 to Houghten et al. (986).

As one of skill in the art will appreciate, VR2 polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., Nature 331:84–86 (1988)). Fusion proteins that have a disulfide-linked dimeric structure due to the IgG part can also be more efficient in binding and neutralizing other molecules than the monomeric VR2 receptor polypeptides or polypeptide fragments alone (Fountoulakis et al., J. Biochem 270:3958–3964 (1995)).

For many proteins, including the extracellular domain of a membrane associated protein, it is known in the art that one or more amino acids may be deleted from the N-terminus or C-terminus without substantial loss of biological function. However, even if deletion of one or more amino acids from the N-terminus or C-terminus of a protein results in modification or loss of one or more biological functions of the protein, other VR2 functional activities may still be retained. For example, in many instances, the ability of the shortened protein to induce and/or bind to antibodies which recognize VR2 (preferably antibodies that bind specifically to VR2) will be retained irrespective of the size or location of the deletion. Whether a particular polypeptide lacking N-terminal and/or C-terminal residues of a complete protein retains such immunologic activities can readily be determined by routine methods described herein and otherwise known in the art.

In one embodiment, the present invention further provides polypeptides having one or more residues deleted from the amino terminus of the amino acid sequence of the VR2 polypeptide depicted in FIGS. 1A–1D (SEQ ID NO:2) or encoded by the cDNA of the deposited clone. Particularly, in one embodiment, N-terminal deletions of the VR2 polypeptide can be described by the general formula m to 889, where m is an integer from 1 to 888 corresponding to the position of amino acid identified in SEQ ID NO:2 and preferably, corresponds to one of the N-terminal amino acid residues identified in the N-terminal deletions specified herein. In specific embodiments, N-terminal deletions of the VR2 polypeptide of the invention comprise, or alternatively, consist of, amino acid residues: V-2 to N-889; S-3 to N-889; L-4 to N-889; W-5 to N-889; W-6 to N-889; L-7 to N-889; A-8 to N-889; C-9 to N-889; P-10 to N-889; D-11 to N-889; R-12 to N-889; G-13 to N-889; E-14 to N-889; L-15 to N-889; S-16 to N-889; S-17 to N-889; R-18 to N-889; S-19 to N-889; P-20 to N-889; P-21 to N-889; C-22 to N-889; R-23 to N-889; L-24 to N-889; A-25 to N-889; R-26 to N-889; W-27 to N-889; A-28 to N-889; E-29 to N-889; G-30 to N-889; D-31 to N-889; R-32 to N-889; E-33 to N-889; T-34 to N-889; R-35 to N-889; T-36 to N-889; C-37 to N-889; L-38 to N-889; L-39 to N-889, E-40 to N-889; L-41 to N-889; S-42 to N-889; A-43 to N-889; Q-44 to N-889; S-45 to N-889; W-46 to N-889; G-47 to N-889; G-48 to N-889; R-49 to N-889; F-50 to N-889; R-51 to N-889; R-52 to N-889; S-53 to N-889; S-54 to N-889; A-55 to N-889; V-56 to N-889; S-57 to N-889; T-58 to N-889; G-59 to N-889; S-60 to N-889; P-61 to N-889; S-62 to N-889; R-63 to N-889; L-64 to N-889; H-65 to N-889; F-66 to N-889; L-67 to N-889; P-68 to N-889; Q-69 to N-889; P-70 to N-889; L-71 to N-889; L-72 to N-889; L-73 to N-889; R-74 to N-889; S-75 to N-889; S-76 to N-889; G-77 to N-889; I-78 to N-889; P-79 to N-889; A-80 to N-889; A-81 to N-889; A-82 to N-889; T-83 to N-889; P-84 to N-889; W-85 to N-889; P-86 to N-889; Q-87 to N-889; P-88 to N-889; A-89 to N-889; G-90 to N-889; L-91 to N-889; Q-92 to N-889; S-93 to N-889; G-94 to N-889; Q-95 to N-889; H-96 to N-889; R-97 to N-889; R-98 to N-889; A-99 to N-889; R-100 to N-889; G-101 to N-889; R-102 to N-889; K-103 to N-889; T-104 to N-889; G-105 to N-889; P-106 to N-889; L-107 to N-889; T-108 to N-889; S-109 to N-889; P-110 to N-889; S-111 to N-889; A-112 to N-889; Q-113 to N-889; R-114 to N-889; S-115 to N-889; W-116 to N-889; L-117 to N-889; D-118 to N-889; R-119 to N-889; A-120 to N-889; M-121 to N-889; P-122 to N-889; P-123 to N-889; P-124 to N-889; P-125 to N-889; R-126 to N-889; M-127 to N-889; T-128 to N-889; S-129 to N-889; P-130 to N-889; S-131 to N-889; S-132 to N-889; S-133 to N-889; P-134 to N-889; V-135 to N-889; F-136 to N-889; R-137 to N-889; L-138 to N-889; E-139 to N-889; T-140 to N-889; L-141 to N-889; D-142 to N-889; G-143 to N-889; G-144 to N-889; Q-145 to N-889; E-146 to N-889; D-147 to N-889; G-148 to N-889; S-149 to N-889; E-150 to N-889; A-151 to N-889; D-152 to N-889; R-153 to N-889; G-154 to N-889; K-155 to N-889; L-156 to N-889; D-157 to N-889; F-158 to N-889; G-159 to N-889; S-160 to N-889; G-161 to N-889; L-162 to N-889; P-163 to N-889; P-164 to N-889; M-165 to N-889; E-166 to N-889; S-167 to N-889; Q-168 to N-889; F-169 to N-889; Q-170 to N-889; G-171 to N-889; E-172 to N-889; D-173 to N-889; R-174 to N-889; K-175 to N-889; F-176 to N-889; A-177 to N-889; P-178 to N-889; Q-179 to N-889; I-180 to N-889; R-181 to N-889; V-182 to N-889; N-183 to N-889; L-184 to N-889; N-185 to N-889, Y-186 to N-889; R-187 to N-889; K-188 to N-889; G-189 to N-889; T-190 to N-889; G-191 to N-889; A-192 to N-889; S-193 to N-889; Q-194 to N-889; P-1 95 to N-889; D-196 to N-889; P-197 to N-889; N-198 to N-889; R-199 to N-889; F-200 to N-889; D-201 to N-889; R-202 to N-889; D-203 to N-889; R-204 to N-889; L-205 to N-889; F-206 to N-889; N-207 to N-889; A-208 to N-889; V-209 to N-889; S-210 to N-889; R-211 to N-889; G-212 to N-889; V-213 to N-889; P-214 to N-889; E-215 to N-889; D-216 to N-889; L-217 to N-889; A-218 to N-889; G-219 to N-889; L-220 to N-889; P-221 to N-889; E-222 to N-889; Y-223 to N-889; L-224 to N-889; S-225 to N-889; K-226 to N-889; T-227 to N-889; S-228 to N-889; K-229 to N-889; Y-230 to N-889; L-231 to N-889; T-232 to N-889; D-233 to N-889; S-234 to N-889; E-235 to N-889, Y-236 to N-889; T-237 to N-889; E-238 to N-889; G-239 to N-889; S-240 to N-889; T-241 to N-889; G-242 to N-889; K-243 to N-889; T-244 to N-889; C-245 to N-889; L-246 to N-889; M-247 to N-889; K-248 to N-889; A-249 to N-889; V-250 to N-889; L-251 to N-889; N-252 to N-889; L-253 to N-889; K-254 to N-889; D-255 to N-889; G-256 to N-889; V-257 to N-889; N-258 to N-889; A-259 to N-889; C-260 to N-889; I-261 to N-889; L-262 to N-889; P-263 to N-889; L-264 to N-889; L-265 to N-889; Q-266 to N-889; I-267 to N-889; D-268 to N-889; R-269 to N-889; D-270 to N-889; S-271 to N-889; G-272 to N-889; N-273 to N-889; P-274 to N-889; Q-275 to N-889; P-276 to N-889; L-277 to N-889; V-278 to N-889; N-279 to N-889; A-280 to N-889; Q-281 to N-889; C-282 to N-889; T-283 to N-889; D-284 to N-889; D-285 to N-889; Y-286 to N-889; Y-287 to N-889; R-288 to N-889; G-289 to N-889; H-290 to N-889; S-291 to N-889; A-292 to N-889; L-293 to N-889; H-294 to N-889; I-295 to N-889; A-296 to N-889; I-297 to N-889; E-298 to N-889; K-299 to N-889; R-300 to N-889; S-301 to N-889; L-302 to N-889; Q-303 to N-889; C-304 to N-889; V-305 to N-889; K-306 to N-889; L-307 to N-889; L-308 to N-889; V-309 to N-889; E-310 to N-889; N-311 to N-889; G-312 to N-889; A-313 to N-889; N-314 to N-889; V-315 to N-889; H-316 to N-889; A-317 to N-889; R-318 to N-889; A-319 to N-889; C-320 to N-889; G-321 to N-889; R-322 to N-889; F-323 to N-889; F-324 to N-889; Q-325 to N-889; K-326 to N-889; G-327 to N-889; Q-328 to N-889; G-329 to N-889; T-330 to N-889; C-331 to N-889; F-332 to N-889; Y-333 to N-889; F-334 to N-889; G-335 to N-889; E-336 to N-889; L-337 to N-889; P-338 to N-889; L-339 to N-889; S-340 to N-889; L-341 to N-889; A-342 to N-889; A-343 to N-889; C-344 to N-889; T-345 to N-889; K-346 to N-889; Q-347 to N-889; W-348 to N-889; D-349 to N-889; V-350 to N-889; V-351 to N-889; S-352 to N-889; Y-353 to N-889; L-354 to N-889; L-355 to N-889; E-356 to N-889; N-357 to N-889; P-358 to N-889; H-359 to N-889; Q-360 to N-889; P-361 to N-889; A-362 to N-889; S-363 to N-889; L-364 to N-889; Q-365 to N-889; A-366 to N-889; T-367 to N-889; D-368 to N-889; S-369 to N-889; Q-370 to N-889; G-371 to N-889; N-372 to N-889; T-373 to N-889; V-374 to N-889; L-375 to N-889; H-376 to N-889; A-377 to N-889; L-378 to N-889; V-379 to N-889; M-380 to N-889; I-381 to N-889; S-382 to N-889; D-383 to N-889; N-384 to N-889; S-385 to N-889; A-386 to N-889; E-387 to N-889; N-388 to N-889; I-389 to N-889; A-390 to N-889; L-391 to N-889; V-392 to N-889; T-393 to N-889; S-394 to N-889; M-395 to N-889; Y-396 to N-889; D-397 to N-889; G-398 to N-889; L-399 to N-889; L-400 to N-889; Q-401 to N-889; A-402 to N-889; G-403 to N-889; A-404 to N-889; R-405 to N-889; L-406 to N-889; C-407 to N-889; P-408 to N-889; T-409 to N-889; V-410 to N-889; Q-411 to N-889; L-412 to N-889; E-413 to N-889; D-414 to N-889; I-415 to N-889; R-416 to N-889; N-417 to N-889; L-418 to N-889; Q-419 to N-889; D-420 to N-889; L-421 to N-889; T-422 to N-889; P-423 to N-889; L-424 to N-889; K-425 to N-889; L-426 to N-889; A-427 to N-889; A-428 to N-889; K-429 to N-889; E-430 to N-889; G-431 to N-889; K-432 to N-889; I-433 to N-889; E-434 to N-889; I-435 to N-889; F-436 to N-889; R-437 to N-889; H-438 to N-889; I-439 to N-889; L-440 to N-889; Q-441 to N-889; R-442 to N-889; E-443 to N-889; F-444 to N-889; S-445 to N-889; G-446 to N-889; L-447 to N-889; S-448 to N-889; H-449 to N-889; L-450 to N-889; S-451 to N-889; R-452 to N-889; K-453 to N-889; F-454 to N-889; T-455 to N-889; E-456 to N-889; W-457 to N-889; C-458 to N-889; Y-459 to N-889; G-460 to N-889; P-461 to N-889; V-462 to N-889; R-463 to N-889; V-464 to N-889; S-465 to N-889; L-466 to N-889; Y-467 to N-889; D-468 to N-889; L-469 to N-889; A-470 to N-889; S-471 to N-889; V-472 to N-889; D-473 to N-889; S-474 to N-889; C-475 to N-889; E-476 to N-889; E-477 to N-889; N-478 to N-889; S-479 to N-889; V-480 to N-889; L-481 to N-889; E-482 to N-889; I-483 to N-889; I-484 to N-889; A-485 to N-889; F-486 to N-889; H-487 to N-889; C-488 to N-889; K-489 to N-889; S-490 to N-889; P-491 to N-889; H-492 to N-889; R-493 to N-889; H-494 to N-889; R-495 to N-889; M-496 to N-889; V-497 to N-889; V-498 to N-889; L-499 to N-889; E-500 to N-889; P-501 to N-889; L-502 to N-889; N-503 to N-889; K-504 to N-889; L-505 to N-889; L-506 to N-889; Q-507 to N-889; A-508 to N-889; K-509 to N-889; W-510 to N-889; D-511 to N-889; L-512 to N-889; L-513 to N-889; I-514 to N-889; P-515 to N-889; K-516 to N-889; F-517 to N-889; F-518 to N-889; L-519 to N-889; N-520 to N-889; F-521 to N-889; L-522 to N-889; C-523 to N-889; of SEQ ID NO:2. Polynucleotides encoding these polypeptides are also encompassed by the invention.

Further embodiments of the invention are directed to C-terminal deletions of the VR2 polypeptide described by the general formula 1 to n, where n is an integer from 2–888 corresponding to the position of amino acid residue identified in SEQ ID NO:2 and preferably, corresponds to one of the C-terminal amino acid residues identified in the C-terminal deletions specified herein. In specific embodiments, C terminal deletions of the VR2 polypeptide of the invention comprise, or alternatively, consist of, amino acid residues: M-1 to S-888; M-1 to Q-887; M-1 to L-886; M-1 to L-885; M-1 to Q-884; M-1 to V-883; M-1 to P-882; M-1 to V-881; M-1 to Y-880; M-1 to N-879; M-1 to E-878; M-1 to E-877; M-1 to S-876; M-1 to A-875; M-1 to G-874; M-1 to D-873; M-1 to E-872; M-1 to D-871; M-1 to E-870; M-1 to K-869; M-1 to P-868; M-1 to P-867; M-1 to S-866; M-1 to A-865; M-1 to L-864; M-1 to V-863; M-1 to P-862; M-1 to N-861; M-1 to E-860; M-1 to L-859; M-1 to T-858; M-1 to R-857; M-1 to P-856; M-1 to V-855; M-1 to G-854; M-1 to A-853; M-1 to G-852; M-1 to S-851; M-1 to P-850; M-1 to D-849; M-1 to E-848; M-1 to C-847; M-1 to L-846; M-1 to T-845; M-1 to P-844; M-1 to L-843; M-1 to T-842; M-1 to Q-841; M-1 to E-840; M-1 to W-839; M-1 to S-838; M-1 to A-837; M-1 to W-836; M-1 to N-835; M-1 to V-834; M-1 to E-833, M-1 to E-832; M-1 to V-831; M-1 to R-830; M-1 to F-829; M-1 to C-828; M-1 to W-827; M-1 to R-826; M-1 to E-825; M-1 to D-824; M-1 to P-823; M-1 to S-822; M-1 to G-821; M-1 to D-820; M-1 to P-819; M-1 to K-818; M-1 to T-817; M-1 to G-816; M-1 to V-815; M-1 to T-814; M-1 to L-813; M-1 to M-812; M-1 to V-811; M-1 to G-810; M-1 to A-809; M-1 to R-808; M-1 to Q-807; M-1 to K-806; M-1 to K-805; M-1 to R-804; M-1 to C-803; M-1 to W-802; M-1 to W-801; M-1 to Y-800; M-1 to G-799; M-1 to N-798; M-1 to E-797; M-1 to M-796; M-1 to E-795; M-1 to L-794; M-1 to V-793; M-1 to S-792; M-1 to I-791; M-1 to A-790; M-1 to K-789; M-1 to Q-788; M-1 to L-787; M-1 to K-786; M-1 to W-785; M-1 to I-784; M-1 to S-783; M-1 to W-782; M-1 to S-781; M-1 to D-780; M-1 to T-779; M-1 to A-778; M-1 to V-777; M-1 to S-776; M-1 to N-775; M-1 to V-774; M-1 to T-773; M-1 to E-772; M-1 to S-771; M-1 to M-770; M-1 to L-769; M-1 to A-768; M-1 to I-767; M-1 to L-766; M-1 to M-765; of SEQ ID NO:2. Polynucleotides encoding these polypeptides are also encompassed by the invention.

Further embodiments of the invention are directed to polypeptide fragments comprising, or alternatively, consisting of, amino acids described by the general formula m to n, where m and n are integers corresponding to any one of the amino acid residues specified above for these symbols, respectively.

It will be recognized in the art that some amino acid sequences of the VR2 receptors can be varied without significant effect to the structure or function of the protein. If such differences in sequence are contemplated, it should be remembered that there will be critical areas on the protein which determine activity. Thus, the invention further includes variations of the VR2 receptors which show substantial VR2 receptor activity or which include regions of VR2 proteins such as the polypeptide portions discussed below. Such mutants include deletions, insertions, inversions, repeats, and type substitutions. As indicated above, guidance concerning which amino acid changes are likely to be phenotypically silent can be found in Bowie et al, "Deciphering the Message in Protein Sequences: Tolerance to Amino Acid Substitutions," *Science* 247:1306–1310 (1990).

Thus, the fragment, derivative or analog of the polypeptide of FIGS. 1A–1D (SEQ ID NO:2), or that encoded by the deposited cDNA, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the VR2 polypeptide is fused with another compound, such as a compound to increase the half-life of the polypeptide (for example, polyethylene glycol), or (iv) one in which the additional amino acids are fused to the full length polypeptide, such as an IgG Fc fusion region peptide or leader or secretory sequence or a sequence which is employed for purification of the VR2 polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in polypeptides with reduced positive charge to improve the characteristics of the VR2 polypeptides. The prevention of aggregation is highly desirable. Aggregation of polypeptides not only results in a loss of activity but can also be problematic when preparing pharmaceutical formulations, because they can be immunogenic. (Pinckard et al., *Clin. Exp. Immunol.* 2:331–340 (1967); Robbins et al., *Diabetes* 36:838–845 (1987); Cleland et al., *Crit. Rev. Therapeutic Drug Carrier Systems* 10:307–377 (1993)).

The replacement of amino acids can also change the selectivity of binding to cell surface receptors. For example, Ostade et al., *Nature* 361:266–268 (1993)) describes certain mutations resulting in selective binding of TNF-a to only one of the two known types of TNF receptors. Thus, the VR2 receptors of the present invention may include one or more amino acid substitutions, deletions or additions, either from natural mutations or human manipulation.

As indicated, changes are preferably of a minor nature, such as conservative amino acid substitutions that do not significantly affect the folding or activity of the protein (see Table 1).

TABLE 1

| Conservative Amino Acid Substitutions | |
|---|---|
| Aromatic | Phenylalanine |
|  | Tryptophan |
|  | Tyrosine |
| Hydrophobic | Leucine |
|  | Isoleucine |
|  | Valine |

TABLE 1-continued

Conservative Amino Acid Substitutions

| | |
|---|---|
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

In specific embodiments, the number of substitutions, additions or deletions in the amino acid sequence of FIGS. 1A–1D (SEQ ID NO:2) and/or any of the polypeptide fragments described herein (e.g., the extracellular domains or intracellular domains) is 100, 90, 80, 75, 70, 60, 50, 40, 35, 30, 25, 20, 15, 10, 9, 8, 7, 6, 5, 4, 3, 2, 1 or 150-100, 100-50, 50-20, 20-10, 5-10, 1-5, 1-3 or 1-2.

Amino acids in the VR2 polypeptides of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as receptor binding in vitro, or in vitro ion (e.g., calcium) flux. Sites that are critical for ligand-receptor binding can also be determined by structural analysis such as crystallization, nuclear magnetic resonance or photoaffinity labeling (Smith et al., *J. Mol. Biol.* 224:899–904 (1992) and de Vos et al., *Science* 255:306–312 (1992)).

The polypeptides of the present invention also include the polypeptide encoded by the deposited cDNA; the polypeptide of FIGS. 1A–1D (SEQ ID NO:2); the polypeptides of FIGS. 1A–1D (SEQ ID NO:2) minus the N-terminal methionine; the polypeptide sequence of any of the VR2 domains described herein; the polypeptide sequence of FIGS. 1A–1D (SEQ ID NO:2) minus a portion, or all of, one or more of the extracellular domains, transmembrane domains, intracellular domains, ankyrin repeat domains, and pore loop of the VR2 receptor shown in FIGS. 1A–1D (SEQ ID NO:2); and polypeptides which are at least 80% identical, more preferably at least 85%, 90% or 95% identical, still more preferably at least 96%, 97%, 98% or 99% identical to the polypeptides described above, and also include portions of such polypeptides with at least 30 amino acids and more preferably at least 50 amino acids.

By a polypeptide having an amino acid sequence at least, for example, 95% "identical" to a reference amino acid sequence of a VR2 polypeptide is intended that the amino acid sequence of the polypeptide is identical to the reference sequence except that the polypeptide sequence may include up to five amino acid alterations per each 100 amino acids of the reference amino acid of a VR2 receptor. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in FIGS. 1A–1D (SEQ ID NO:2), the amino acid sequence encoded by the deposited cDNA clone, or fragments thereof, can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present 20 invention, the parameters are set, of course, such that the percentage of identity is calculated over the full length of the reference amino acid sequence and that gaps in homology of up to 5% of the total number of amino acid residues in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al, *Comp. App. Biosci.* 6:237–245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

The polypeptides of the present invention have uses which include, but are not limited to, molecular weight marker on SDS-PAGE gels or on molecular sieve gel filtration columns using methods well known to those of skill in the art.

Detection of Disease States

Cells which express the VR2 polypeptides and are believed to have a potent cellular response to vanilloid receptor family ligand include, for example, hematopoietic cells, blood cells and cells and tissue of the immune system. In addition, Northern blots revealed an approximately 2.5 to 3.5 kb mRNA observed most abundantly in spleen, lymph node, peripheral blood leukocytes, and lung, and next highest levels were observed in thymus, heart, placenta, brain, bone marrow, and fetal liver. By "a cellular response to a vanilloid receptor family ligand" is intended any genotypic, phenotypic, and/or morphologic change to a cell, cell line, tissue, tissue culture or patient that is induced by a vanilloid receptor family ligand or stimuli (e.g., heat). As indicated, such cellular responses include not only normal physiological responses to vanilloid receptor family ligands or stimuli (e.g., heat), but also diseases associated with aberrant pain sensitivity, and aberrant cell secretion, activation, survival, migration and differentiation.

Thus, it is believed that certain tissues in mammals with certain diseases (e.g., pain syndromes and insensitivities, diseases associated with increased or decreased cell survival, secretion, activation, migration, differentiation, and proliferation; inflammatory diseases; ischemia; aberrant host defense; aberrant immune surveillance; arthritis; autoimmunity; (e.g., lupus erythematosus (SLE), rheumatoid arthritis (RA), insulin-dependent diabetes, multiple sclerosis (MS), giant cell arteritis, polyarteritis nodosa, myasthenia gravis, scleroderma, and graft versus host disease): immune dysfunction; and allergy), express significantly altered (e.g., enhanced or decreased) levels of the VR2 polypeptide and mRNA encoding the VR2 polypeptide when compared to a corresponding "standard" mammal, i.e., a mammal of the same species not having the disease. Diseases associated with increased cell survival, include cancers (such as follicular lymphomas, carcinomas with p53 mutations, and hormone-dependent tumors); autoimmune disorders (such as systemic lupus erythematosus and immune-related glomerulonephritis rheumatoid arthritis) and viral infections (such as herpes viruses, pox viruses and adenoviruses), information graft v. host disease, acute graft rejection, and chronic graft rejection. Diseases associated with decreased cell survival, include AIDS; neurodegenerative disorders (such as Alzheimer's disease, Parkinson's disease, Amyotrophic lateral sclerosis, Retinitis pigmentosa, Cerebellar degeneration); myelodysplastic syndromes (such as aplastic anemia), ischemic injury (such as that caused by myocardial infarction, stroke and reperfusion injury), toxin-induced liver disease (such as that caused by alcohol), septic shock, cachexia and anorexia.

Further, it is believed that altered levels of the VR2 polypeptide can be detected in certain body fluids (e.g., sera, plasma, urine, and spinal fluid) from mammals with the disorder when compared to sera from mammals of the same species not having the disorder. Thus, the invention provides a diagnostic method useful during diagnosis, which involves assaying the expression level of the gene encoding the VR2 polypeptide in mammalian cells or body fluid and comparing the gene expression level with a standard VR2 gene expression level, whereby an increase or decrease in the gene expression level over the standard is indicative of the disease.

By "assaying" the expression level of the gene encoding the VR2 polypeptide" is intended qualitatively or quantitatively measuring or estimating the level of the VR2 polypeptide or the level of the mRNA encoding the VR2 polypeptide in a first biological sample either directly (e.g., by determining or estimating absolute polypeptide or mRNA level) or relatively (e.g., by comparing to the VR2 polypeptide level or mRNA level in a second biological sample). Preferably, the VR2 receptor protein level or mRNA level in the first biological sample is measured or estimated and compared to a standard VR2 receptor protein level or mRNA level, the standard being taken from a second biological sample obtained from an individual not having the disease state. As will be appreciated in the art, once a standard VR2 receptor protein level or mRNA level is known, it can be used repeatedly as a standard for comparison.

By "biological sample" is intended any biological sample obtained from an individual, cell line, tissue culture, or other source which contains VR2 receptor protein or mRNA. Biological samples include mammalian body fluids (such as sera, plasma, urine, synovial fluid and spinal fluid), and spleen, lymph node, peripheral blood leukocytes, lung, thymus, heart, placenta, brain, bone marrow, and fetal liver, and other tissues. Methods for obtaining tissue biopsies and body fluids from mammals are well known in the art. Where the biological sample is to include mRNA, a tissue biopsy is the preferred source.

Where a diagnosis has already been made according to conventional methods, the present invention is useful as a prognostic indicator, whereby patients exhibiting altered VR2 gene expression will experience a worse clinical outcome relative to patients expressing the gene at a normal level.

Nucleic acids for diagnosis may be obtained from a biological sample of a subject, such as from blood, urine, saliva, tissue biopsy or autopsy material, using techniques known in the art. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled VR2 nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing (see, e.g., Myers et al., *Science* 230:1242 (1985)). Sequence changes at specific locations may also be revealed by nuclease protection assays, such as RNase and S1 protection or the chemical cleavage method (see Cotton et al., *Proc. Natl. Acad. Sci. USA* 85:4397–4401 (1985)). In another embodiment, an array of oligonucleotides probes comprising VR2 polynucleotide sequences or fragments thereof, can be constructed to conduct efficient screening of e.g., genetic mutations. Array technology methods are well known and have general applicability and can be used to address a variety of questions in molecular genetics including gene expression, genetic linkage, and genetic variability (see for example, Chee et al., *Science* 274:610–613 (1996)).

The diagnostic assays offer a process for diagnosing or determining a susceptibility to specific diseases through detection of mutation in the VR2 gene by the methods described herein or otherwise known in the art.

In addition, specific diseases can be diagnosed by methods comprising determining from a sample derived from a subject an abnormally decreased or increased level of VR2 polypeptide or mRNA. Decreased or increased expression can be measured at the RNA level using any of the methods well known in the art, which include, but are not limited to, Northern blot analysis, (Harada et al., *Cell* 63:303–312 (1990)), S1 nuclease mapping (Fijita et al., Cell 49:357–367 (1987)), RNAse protection, the polymerase chain reaction (PCR), reverse transcription in combination with the polymerase chain reaction (RT-PCR) (Makino et al., *Technique* 2:295–301 (1990), reverse transcription in combination with the ligase chain reaction (RT-LCR) and other hybridization methods.

Assaying VR2 polypeptide levels in a biological sample can be by any techniques known in the art, which include, but are not limited to, radioimmunoassays, competitive-binding assays, Western Blot analysis and enzyme linked immunosorbent assays (ELISAs) and other antibody-based techniques. For example, VR2 polypeptide expression in tissues can be studied with classical immunohistological methods (Jalkanen et al., *J. Cell. Biol.* 101:976–985 (1985); Jalkanen et al., *J. Cell. Biol.* 105:3087–3096 (1987)).

Suitable labels are known in the art and include enzyme labels, such as, Glucose oxidase, and radioisotopes, such as iodine ($^{125}$I, $^{121}$I), carbon ($^{14}$C), sulfur ($^{35}$S), tritium ($^{3}$H), indium ($^{112}$In), and technetium ($^{99m}$Tc), and fluorescent labels, such as fluorescein and rhodamine, and biotin.

Antibodies

The VR2 polypeptides, their variants, fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Thus, as used herein, the term "antibody" (Ab) or "monoclonal antibody" (mAb) is meant to include intact molecules as well as antibody fragments (such as, for example, Fab and Fab (ab') fragments) which are capable of specifically binding to VR2 receptor protein. Fab and F(ab') fragments lack the Fc fragment of intact antibody, clear more rapidly from the circulation, and may have less non-specific tissue binding of an intact antibody (Wahl et al., *J. Nucl. Med.* 24:316–325 (1983)). Thus, these fragments are preferred. Various procedures known in the art may be used for the production of the antibodies and fragments described herein.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself In this manner, even a sequence encoding only a fragment of the polypeptides can be used to generate antibodies binding the whole native polypeptides. Such antibodies can then be used to isolate the polypeptide from tissue expressing that polypeptide.

The antibodies of the invention may be prepared by any of a variety of techniques known in the art using VR2 receptor immunogens of the present invention. Such VR2 receptor immunogens include the full-length VR2 polypeptide shown in FIGS. 1A–1D (SEQ ID NO:2) and polypeptide fragments of the receptor comprising the ligand binding domain, all or a portion of one or more of the extracellular domains, transmembrane domains, intracellular domains, ankyrin domains, and pore loop of the VR2 receptors, or any combination thereof. For example, cells expressing the VR2 receptor polypeptide, or an antigenic fragment thereof, can be administered to an animal in order to induce the production of sera containing polyclonal antibodies. In a preferred method, a preparation of VR2 polypeptide is prepared and purified to render it substantially free of natural contaminants. Such a preparation is then introduced into an animal in order to produce polyclonal antisera of greater specific activity. For preparation of monoclonal antibodies, any technique which provides antibodies produced by continuous cell line cultures can be used. Examples include the hybridoma technique (Kohler and Milstein, *Nature* 256:495–497 (1975)), the trioma technique, the human B-cell hybridoma technique (Kozbor et al., *Immunology Today* 4:72(1983)), the EBV-hybridomatechniqueto produce human monoclonal antibodies (Cole, et al., in: *Monoclonal Antibodies and Cancer Therapy*, Alan R. Liss, Inc., pp. 77–96 (1985)). In general, such procedures involve immunizing an animal (preferably a mouse) with a VR2 receptor protein antigen or, more preferably, with a VR2 receptor protein-expressing cell. Suitable cells can be recognized by their capacity to bind anti-VR2 receptor protein antibody. Such cells may be cultured in any suitable tissue culture medium; however, it is preferable to culture cells in Earle's modified Eagle's medium supplemented with 10% fetal bovine serum (inactivated at about 56 C), and supplemented with about 10 g/l of nonessential amino acids, about 1,000 U/ml of penicillin, and about 100 µg/ml of streptomycin. The splenocytes of such mice are extracted and fused with a suitable myeloma cell line. Any suitable myeloma cell line may be employed in accordance with the present invention; however, it is preferable to employ the parent myeloma cell line (SP20), available from the American Type Culture Collection, Manassas, Va. After fusion, the resulting hybridoma cells are selectively maintained in HAT medium, and then cloned by limiting dilution as described by Wands et al., *Gastroenterology* 80:225–232(1981)). The hybridoma cells obtained through such a selection are then assayed to identify clones which secrete antibodies capable of binding the VR2 receptor protein antigen.

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

For in vivo use of anti-TNF-gamma in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art (Morrison, *Science* 229:1202 (1985); Oi, et al., *BioTechniques* 4:214 (1986); Cabilly, et al., U.S. Pat. No. 4,816,567; Taniguchi, et al., EP 171496; Morrison, et al., EP 173494; Neuberger, et al., WO 8601533; Robinson, et al., WO 8702671; Boulianne et al., *Nature* 312:643 (1984); Neuberger et al., *Nature* 314:268 (1985).

Antibodies of the invention can be used in methods known in the art relating to the localization and activity of the polypeptide sequences of the invention, e.g., for imaging these polypeptides, measuring levels thereof in appropriate physiological samples, etc. The antibodies also have use in immunoassays and in therapeutics as agonists and antagonists of VR2.

Agonists and Antagonists of VR2

In one embodiment, the present invention is directed to a method for identifying compounds that interact with (e.g., bind to) VR2 polypeptides (including, but not limited to full-length VR2, and one or more extracellular or intracellular domains of VR2). Compounds identified may be useful, for example, in modulating the activity VR2 gene products; in elaborating the biological function of VR2; in screens for identifying compounds that disrupt normal VR2 interactions; or may in themselves disrupt such interactions and therefore may have uses which include, for example, as analgesic agents regulators of hematopoiesis or as regulators of immune response.

The principle of the assays used to identify compounds that bind to VR2 involves preparing a reaction mixture of VR2 and the test compound under conditions and for a time sufficient to allow the two components to interact and bind, thus forming a complex which can be removed and/or detected in the reaction mixture. The VR2 polypeptide species used can vary depending upon the goal of the screening assay. For example, where agonists of the natural ligand are sought, the full length VR2, or a soluble truncated VR2 (e.g., containing one or more extracellular or intracellular domains, but in which the transmembrane domains are deleted from the molecule, a peptide corresponding to a VR2 extracellular domain or a fusion protein containing a VR2 extracellular domain fused to a polypeptide that affords advantages in the assay system (e.g., labeling, isolation of the resulting complex, etc.) can be utilized. Where compounds that interact with a VR2 intracellular domain are sought to be identified, peptides corresponding to the VR2 intracellular domain and fusion proteins containing a VR2 intracellular domain can be used.

The compounds that may be screened in accordance with the invention include, but are not limited to, soluble peptides, including but not limited to those found in random peptide libraries; (see, e.g., Lam et al., *Nature* 354 82–84 (1991); Houghten, R., et al., *Nature* 354:84–86 (1991)), cell or tissue lysates, and biological samples (e.g,. cells, tissue, sera and lymph). Such compounds may also be found in random peptide expression libraries, and genomic or cDNA expression libraries, or combinatorial chemistry-derived molecular libraries made of D- and/or L-configuration amino acids; phosphopeptides (including, but not limited to members of random or partially degenerate, directed phosphopeptide libraries; see, e.g., Songyang et al., *Cell* 72:767–778 (1993)); antibodies (including, but not limited to, polyclonal, monoclonal, humanized, anti-idiotypic, chimeric or single chain antibodies, and FAb, F(ab')2 and FAb expression library fragments, and epitope-binding fragments thereof); and small organic or inorganic molecules.

Numerous experimental methods may be used to select and detect polypeptides that bind with VR2, including, but not limited to, protein affinity chromatography, affinity blotting, immunoprecipitation, cross-linking, and library based methods such as protein probing, phage display and the two-hybrid system. See generally, Phizicky et al., *Microbiol. Rev.* 59:94–123 (1995). Once isolated, such an VR2-binding polypeptide can be identified and can, in turn, be used, in conjunction with standard techniques, to identify polypeptides with which it interacts. For example, at least a portion of the amino acid sequence of a polypeptide that interacts with VR2 can be ascertained using techniques well known to those of skill in the art, such as via the Edman degradation technique. (See, e.g., Creighton, 1983, "Proteins: Structures and Molecular Principles", W. H. Freeman & Co., N.Y., pp.34–49). The amino acid sequence obtained may be used as a guide for the generation of oligonucleotide mixtures that can be used to screen for gene sequences encoding such polypeptides. Screening may be accomplished, for example, by standard hybridization or PCR techniques. Techniques for the generation of oligonucleotide mixtures and the screening are well-known. (See, e.g., Sambrook et al., *Molecular Cloning: A laboratory Manual*, 2nd Edit., (1989), Cold Spring Harbor Laboratory Press; and PCR Protocols: A Guide to Methods and Applications, 1990, Innis, M. et al., eds. Academic Press, Inc., New York).

Additionally, methods may be employed which result in the simultaneous identification of genes which encode polypeptides interacting with VR2. These methods include, for example, probing expression libraries, in a manner similar to the well known technique of antibody probing of (gt11 libraries, using labeled VR2 polypeptide, such as a VR2 fusion protein wherein a VR2 domain is fused to a marker (e.g., an enzyme, fluor, luminescent protein, or dye), or an Ig-Fc domain. For example, the two-hybrid system may be used to detect interaction between VR2 and candidate proteins for which genes encoding the candidate polypeptides are available by constructing the appropriate hybrids and testing for reporter gene activity. If an interaction is detected using the two-hybrid method, deletions can be made in the DNA encoding the candidate interacting polypeptide or the VR2 polypeptide to identify a minimal domain for interaction. Alternatively, the two-hybrid system can be used to screen available organismal and/or mammalian tissue specific libraries of activation domain hybrids to identify polypeptides that bind to a VR2 polypeptide. These screens result in the immediate availability of the cloned gene for any new polypeptide identified. In addition, since multiple clones that encode overlapping regions of protein are often identified, the minimal domain for interaction may be readily apparent from the initial screen.

Assays may also be used that identify compounds which bind to VR2 gene regulatory sequences (e.g., promoter or enhancer sequences) and which may modulate VR2 gene expression. See e.g., Platt, *J. Biol. Chem.* 269:28558–28562 (1994), which is incorporated herein by reference in its entirety.

The screening assays can be conducted in a variety of ways. For example, one method to conduct such an assay would involve anchoring the VR2 polypeptide (e.g., fusion protein) or the test substance onto a solid phase and detecting VR2/test compound complexes anchored on the solid phase at the end of the reaction. In one embodiment of such a method, the VR2 reactant may be anchored onto a solid surface, and the test compound, which is not anchored, may be labeled, either directly or indirectly.

In practice, microtiter plates may conveniently be utilized as the solid phase. The anchored component may be immobilized by non-covalent or covalent attachments. Non-covalent attachment may be accomplished by simply coating the solid surface with a solution of the polypeptide and drying. Alternatively, an immobilized antibody, preferably a monoclonal antibody, specific for the polypeptide to be immobilized may be used to anchor the polypeptide to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for VR2 polypeptide or fusion protein or the test compound to anchor any complexes formed in solution, and a labeled antibody specific for the other component of the possible complex to detect anchored complexes.

Alternatively, cell-based assays can be used to identify compounds that interact with VR2. Such cell-based systems can include, for example, recombinant or non-recombinant cells, such as cell lines, which express the VR2. For example spleen, lymph node, peripheral blood leukocytes, lung, thymus, heart, placenta, brain, bone marrow, and liver cells, or cell lines derived from spleen, lymph node, peripheral blood leukocytes, lung, thymus, heart, placenta, brain, bone marrow, and liver cells can be used. In addition, expression host cells (e.g., COS cells, CHO cells, HEK293 cells, fibroblasts) genetically engineered (e.g., by transfection or transduction of VR2 DNA) to express a functional VR2 and to respond to activation by the natural VR2 ligand (e.g., a vanilloid compound, such as, for example, capsaicin), e.g., as measured by a chemical or phenotypic change, induction of another host cell gene, change in ion flux (e.g., $Ca^{+2}$), etc., can be used as an end point in the assay. Interaction of the test compound with, for example, one or more VR2 extracellular domains expressed by the host cell can be determined by comparison or competition with VR2 ligands (e.g., vanilloid compounds such as, capsaicin), by the ability to induce a VR2 mediated cellular response (e.g., ion (e.g., $Ca^{+2}$) flux), and other techniques known in the art. (See generally Caterina et al., Nature 389:816–824 (1997) which is herein incorporated by reference in its entirety). Thus, the present invention also provides a screening method for identifying compounds capable eliciting a cellular response induced by VR2 receptors, which involves contacting cells which express VR2 with the candidate compound, and comparing the cellular response to that observed in absence of the candidate compound (i.e., the standard); whereby, an increased cellular response over the standard indicates that the compound is an agonist.

Cellular responses that may be assayed according to this embodiment, include, but are not limited to alterations in the expression of the VR2 gene, e.g., by assaying cell lysates for VR2 mRNA transcripts (e.g., by Northern analysis) or for VR2 expressed in the cell; compounds which regulate or modulate expression of the VR2 gene are good candidates as therapeutics. Additionally, activity of the VR2 signal transduction pathway itself(e.g., cation flux, such as calcium flux) can be routinely assayed using techniques known in the art (see, e.g., Caterina et al., Nature 389:816–824 (1997), the contents of which are herein incorporated by reference in its entirety).

In another embodiment, the present invention is directed to a method for inhibiting an activity (e.g., ion flux (e.g., $Ca^{+2}$) flux), of VR2 induced by a VR2 ligand or VR2 stimulus (e.g., temperature), which involves administering to a cell which expresses a VR2 polypeptide, an effective amount of a VR2 receptor ligand, analog or an antagonist capable of decreasing VR2 mediated signaling. Preferably, VR2 receptor mediated signaling is decreased to treat a disease wherein increased ion flux is exhibited. An antagonist can include soluble forms of the VR2 and antibodies directed against the VR2 polypeptides which block VR2 receptor mediated signaling. Preferably, VR2 receptor mediated signaling is decreased to treat a disease, or to decrease survival, secretion, proliferation, migration and/or differentiation of cells.

In an additional embodiment, the present invention is directed to a method for increasing an activity (e.g., ion (e.g., $Ca^{+2}$) flux), induced by a VR2 ligand (e.g., a vanilloid, such as, capsaicin) or VR2 stimulus (e.g., heat), which involves administering to a cell which expresses a VR2 polypeptide an effective amount of an agonist capable of increasing VR2 receptor mediated signaling. Preferably, VR2 receptor mediated signaling is increased to treat a disease wherein decreased ion flux is exhibited. Agonists of the present invention include monoclonal antibodies directed against the VR2 polypeptides which stimulate VR2 receptor mediated signaling. Preferably, VR2 receptor mediated signaling is increased to treat a disease, and to increase survival, secretion, proliferation, migration, and/or differentiation of cells.

By "agonist" is intended naturally occurring and synthetic compounds capable of eliciting or enhancing ion (e.g., $Ca^{+2}$)flux mediated by VR2 polypeptides. Such agonists include agents which increase expression of VR2 receptors or increase the sensitivity of the expressed receptor. By "antagonist" is intended naturally occurring and synthetic compounds capable of inhibiting VR2 mediated ion (e.g., $Ca^{+2}$) flux. Such antagonists include agents which decrease expression of VR2 receptors or decrease the sensitivity of the expressed receptor. Whether any candidate "agonist" or "antagonist" of the present invention can enhance or inhibit a VR2 mediated cellular response, such as, for example, ion flux, and cell proliferation, survival, and differentiation can be determined using art-known ligand/receptor cellular response assays, and ion flux assays, including those described herein.

Thus, the present invention also provides a screening method for identifying compounds capable of enhancing or inhibiting a cellular response induced by VR2 receptors. The method involves contacting cells which express VR2 polypeptides with the candidate compound in the presence of a VR2 ligand (e.g., a vanilloid compound, such as, capsaicin) or other stimulus (e.g., heat), assaying a cellular response (e.g., ion (e.g., $Ca^{+2}$) flux), and comparing the cellular response to a standard cellular response, the standard being assayed when contact is made between the VR2 ligand and VR2, or when VR2 is exposed to the stimulus, in absence of the candidate compound; whereby, an increased cellular response over the standard indicates that the compound is an agonist of the VR2-mediated signaling pathway and a decreased cellular response over the standard indicates that the compound is an antagonist of the VR2-mediated signaling pathway. By "assaying a cellular response" is intended qualitatively or quantitatively measuring a cellular response to a candidate compound and/or a VR2 ligand or VR2 stimulus (e.g., determining or estimating an increase or decrease in ion (e.g., $Ca^{+2}$) flux). By the invention, a cell expressing a VR2 polypeptide can be contacted with either an endogenous or exogenously administered VR2 ligand.

One such screening technique involves the use of cells which express the receptor (for example, transfected kidney-derived HEK293 cells) in a system which measures intracellular $Ca^{+2}$ changes caused by receptor activation, for example, as described Caterina et al., Nature 389:816–824 (1997). For example, compounds may be contacted with a cell which expresses the VR2 polypeptide of the present invention and ion (e.g., $Ca^{+2}$) flux, may be measured to determine whether the potential compound activates (i.e., leads to elevated ion flux) or inhibits the receptor.

Another method involves screening for compounds which inhibit activation of the receptor polypeptide of the present invention (i.e., antagonists) by determining inhibition of binding of labeled ligand to cells which have the receptor on the surface thereof. Such a method involves transfecting a eukaryotic cell with DNA encoding the VR2 polypeptide such that the cell expresses the receptor on its surface and contacting the cell with a compound in the presence of a labeled form of a VR2 ligand (e.g., a vanilloid compound, such as capsaicin). The ligand can be labeled, e.g., by radioactivity. The amount of labeled ligand bound to the receptors is measured, e.g., by measuring radioactivity of the VR2 polypeptide. If the compound binds to the receptor as determined by a reduction of labeled ligand which binds to the receptors, the binding of labeled ligand to the VR2 polypeptide is inhibited.

Soluble forms of the polypeptides of the present invention may be utilized in the ligand binding assay described above. These forms of the VR2 receptor are contacted with ligands in the extracellular medium after they are secreted. A determination is then made as to whether the secreted protein will bind to VR2 receptor ligands.

Agonists according to the present invention include compounds such as, for example, vanilloid receptor ligand peptide fragments, and neurotransmitters. Preferred agonists include VR2 polypeptide fragments of the invention and/or polyclonal and monoclonal antibodies raised against a VR2 polypeptide, or a fragment thereof.

VR2 polypeptides and polynucleotides and compounds identified as VR2 agonists or antagonists using assays described herein or otherwise known in the art, have uses which include, but are not limited to, treating diseases, regulating hematopoiesis, regulating immune responses, regulating cell survival, activation, secretion, migration and differentiation, regulating pain, and in developing analgesic agents and in furthering our understanding of pain insensitivity and pain syndromes.

Prophylactic and Therapeutic Methods

It is to be understood that although the following discussion is specifically directed to human patients, the teachings are also applicable to any animal that expresses VR2.

As noted above, VR2 is structurally related to members of the TRP family of ion channels and shares significant homology with rat vanilloid receptor-1 which has been demonstrated to mediate influx of calcium ions into the cytoplasm of cells expressing VR2 and is believed to be involved in diverse human diseases ranging from congenital pain insensitivity to chronic pain. Thus, it is likely that VR2 is active in modulating growth regulatory activities (e.g., cell survival, secretion, differentiation and/or cell proliferation) and pain perception. Further, VR2, like VR1, might be involved in detection of noxious stimuli that accompany such conditions as inflammation and ischemia. Additionally, the expression profile of VR2 suggests that it may play a role in a broader variety of cell types than observed for VR1. Particularly, VR2 is expressed on non-neuronal cells in addition to neuronal cells, most notably hematopoietic tissue, cells and tissue of the immune system, and blood cells. Thus VR2 plays a role in regulating the flux of calcium or other cations into other cells, such as, hematopoietic cells (e.g., macrophages), and this flux is likely to result in activation, survival, proliferation, migration, and differentiation, as well as the regulation of cytokine profiles by such cells. Thus VR2 is likely to play a role in influencing various diseases or medical conditions, including, but not limited to, inflammation, host defense, immune surveillance, arthritis, MS, autoimmunity, immune dysfunction, and allergy. Additionally, VR2 appears to be expressed in other cell populations (e.g., endothelial cells, mesenchymal cells, and epithelial cells) and thus VR2 likely regulates ion flux into these cells, thereby regulating their survival, differentiation, morphology, and proliferation. Accordingly, it is likely that VR2 plays a role in other physiological or disease conditions, including, cancer, angiogenesis, wound healing, fibrosis, and tissue regeneration. Any method which neutralizes or enhances VR2 mediated signaling can be used to modulate growth regulatory activities (e.g., cell proliferation), and other activities mediated by VR2 signaling, such as, for example, pain sensitivity, inflammation, host defense, immune surveillance, arthritis, MS, autoimmunity, immune dysfunction, allergy, cancer, angiogenesis, wound healing, fibrosis, and tissue regeneration.

VR2 polynucleotides or polypeptides (including VR2 fragments, variants, derivatives, and analogs, and VR2 agonists and antagonists as described herein) may be useful in treating disorders associated with chronic pain syndromes, congenital pain insensitivity, inflammation, and ischemia. Additionally, these compounds may be useful in treating or preventing cell death (e.g., of hematopoietic cells during processes of inflammation of tissue injury).

VR2 polypeptides or polynucleotides (including VR2 fragments, variants, derivatives, and analogs, and VR2 agonists and antagonists as described herein) may be useful in treating deficiencies or disorders of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune deficiencies or disorders may be genetic, somatic, such as cancer or some autoimmune disorders, acquired (e.g., by chemotherapy or toxins), or infectious. Moreover, VR2 polynucleotides or polypeptides can be used as a marker or detector of a particular immune system disease or disorder.

VR2 polynucleotides or polypeptides (including VR2 fragments, variants, derivatives, and analogs, and VR2 agonists and antagonists as described herein) may be useful in treating or detecting deficiencies or disorders of hematopoietic cells. As further discussed below, VR2 polypeptides, polynucleotides, and/or VR2 agonists or antagonists could be used to increase differentiation and proliferation of hematopoietic cells, including the pluripotent stem cells, in an effort to treat those disorders associated with a decrease in certain (or many) types of hematopoietic cells. Examples of immunologic deficiency syndromes include, but are not limited to: blood protein disorders (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria. Additionally, VR2 polypeptides, polynucleotides and/or VR2 antagonists can be used to treat or prevent the killing of hematopoietic cells and other cells during processes of inflammation or tissue injury.

Moreover, VR2 polypeptides or polynucleotides (including VR2 fragments, variants, derivatives, and analogs, and VR2 agonists and antagonists as described herein) can also be used to modulate hemostatic (the stopping of bleeding) or thrombolytic activity (clot formation). For example, by increasing hemostatic or thrombolytic activity, VR2 polynucleotides or polypeptides could be used to treat blood coagulation disorders (e.g., afibrinogenemia, factor deficiencies), blood platelet disorders (e.g. thrombocytopenia), or wounds resulting from trauma, surgery, or other causes. Alternatively, VR2 polynucleotides, polypeptides and/or VR2 agonists or antagonists that can decrease hemostatic or thrombolytic activity could be used to inhibit or dissolve clotting, important in the treatment of heart attacks (infarction), strokes, or scarring.

VR2 polynucleotides or polypeptides (including VR2 fragments, variants, derivatives, and analogs, and VR2 agonists or VR2 antagonists as described herein) may also be useful in treating or detecting autoimmune disorders. Many autoimmune disorders result from inappropriate recognition of self as foreign material by immune cells. This inappropriate recognition results in an immune response leading to the destruction of the host tissue. Therefore, the administration of VR2 polypeptides or polynucleotides and/or VR2 agonists or VR2 antagonists that can inhibit an immune response, particularly the proliferation, differentiation, or chemotaxis of T-cells, may be an effective therapy in preventing autoimmune disorders. Examples of autoimmune disorders that can be treated or detected by VR2 include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitus, and autoimmune inflammatory eye disease.

Similarly, allergic reactions and conditions, such as asthma (particularly allergic asthma) or other respiratory problems may also be treated by VR2 polypeptides, VR2 polynucleotides or VR2 agonists or VR2 antagonists. Moreover, VR2 can be used to treat anaphylaxis, hypersensitivity to an antigenic molecule, or blood group incompatibility.

VR2 polynucleotides or polypeptides (including VR2 fragments, variants, derivatives, and analogs, and VR2 agonists and VR2 antagonists as described herein) may also be used to treat and/or prevent organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of VR2 polypeptides or polynucleotides and/or VR2 agonists or antagonists that inhibits an immune response, particularly the proliferation, differentiation, or chemotaxis of T-cells, may be an effective therapy in preventing organ rejection or GVHD.

Similarly, VR2 polypeptides or polynucleotides (including VR2 fragments, variants, derivatives, and analogs, and VR2 agonists and VR2 antagonists as described herein) may also be used to modulate inflammation. For example, VR2 polypeptides or polynucleotides and/or VR2 agonists and antagonists of the invention may inhibit the proliferation and differentiation of cells involved in an inflammatory response or alternatively may be involved in killing of hematopoietic cells during processes of inflammation or tissue injury. These molecules can be used to treat inflammatory conditions, both chronic and acute conditions, including inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1). Additionally, these molecules may be used to treat or prevent killing of hematopoietic cells and/or other cells during processes of inflammation or tissue injury.

VR2 polypeptides or polynucleotides (including VR2 fragments, variants, derivatives, and analogs, and VR2 agonists and antagonists as described herein) can be used to treat or detect hyperproliferative disorders, including neoplasms. VR2 polypeptides or polynucleotides and/or VR2 agonists or antagonists, may inhibit the proliferation of the disorder through direct or indirect interactions. Alternatively, VR2 polypeptides or polynucleotides and/or VR2 agonists or antagonists may proliferate other cells which can inhibit the hyperproliferative disorder. For example, by increasing an immune response, particularly increasing antigenic qualities of the hyperproliferative disorder or by proliferating, differentiating, or mobilizing T-cells, hyperproliferative disorders can be treated. This immune response may be increased by either enhancing an existing immune response, or by initiating a new immune response. Alternatively, decreasing an immune response may also be a method of treating hyperproliferative disorders, such as a chemotherapeutic agent.

Examples of hyperproliferative disorders that can be treated or detected by VR2 polynucleotides or polypeptides and/or VR2 agonists or antagonists include, but are not limited to, neoplasms located in the: blood, abdomen, bone, lung, breast, digestive system, liver, pancreas, prostate, peritoneum, endocrine glands (adrenal, parathyroid, pituitary, testicles, ovary, thymus, thyroid), eye, head and neck, nervous (central and peripheral), lymphatic system, hematopoietic tissue, pelvic, skin, soft tissue, spleen, thoracic, and urogenital.

Similarly, other hyperproliferative disorders can also be treated or detected by VR2 polynucleotides or polypeptides and/or VR2 agonists or antagonists. Examples of such hyperproliferative disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

VR2 polypeptides or polynucleotides (including VR2 fragments, variants, derivatives, and analogs, and VR2 agonists and antagonists as described herein) can be used to treat or detect infectious agents. For example, by increasing the immune response, particularly increasing the proliferation and differentiation of B and/or T cells, infectious diseases may be treated. The immune response may be increased by either enhancing an existing immune response, or by initiating a new immune response. Alternatively, VR2 polypeptides or polynucleotides and/or VR2 agonists or antagonists may also directly inhibit the infectious agent, without necessarily eliciting an immune response.

Viruses are one example of an infectious agent that can cause disease or symptoms that can be treated by VR2 polynucleotides or polypeptides and/or VR2 agonists or antagonists. Examples of viruses, include, but are not limited to, the following DNA and RNA viral families: Arbovirus, Adenoviridae, Arenaviridae, Arterivirus, Bimaviridae, Bunyaviridae, Caliciviridae, Circoviridae, Coronaviridae, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza), Papovaviridae, Parvoviridae, Picornaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, encephalitis, eye infections (e.g., conjunctivitis, keratitis), chronic fatigue syndrome, hepatitis (A, B, C, E, Chronic Active, Delta), meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. VR2 polypeptides or polynucleotides and/or VR2 agonists or antagonists can be used to treat any of these symptoms or diseases.

Similarly, bacterial or fungal agents that can cause disease or symptoms and that can be treated by VR2 polynucleotides or polypeptides and/or VR2 agonists or antagonists include, but are not limited to, the following Gram-Negative and Gram-positive bacterial families and fungi: Actinomycetales (e.g., Corynebacterium, Mycobacterium, Norcardia), Aspergillosis, Bacillaceae (e.g., Anthrax, Clostridium), Bacteroidaceae, Blastomycosis, Bordetella, Borrelia, Brucellosis, Candidiasis, Campylobacter, Coccidioidomycosis, Cryptococcosis, Dermatocycoses, Enterobacteriaceae (Kiebsiella, Salmonella, Serratia, Yersinia), Erysipelothrix, Helicobacter, Legionellosis, Leptospirosis, Listeria, Mycoplasmatales, Neisseriaceae (e.g., Acinetobacter, Gonorrhea, Menigococcal), Pasteurellacea Infections (e.g., Actinobacillus, Heamophilus, Pasteurella), Pseudomonas, Rickettsiaceae, Chlamydiaceae, Syphilis, and Staphylococcal. These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis, Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. VR2 polypeptides or polynucleotides and/or VR2 agonists or antagonists can be used to treat or detect any of these symptoms or diseases.

Moreover, parasitic agents causing disease or symptoms that can be treated VR2 polynucleotides or polypeptides and/or VR2 agonists or antagonists include, but are not limited to, the following families: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas. These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), Malaria, pregnancy complications, and toxoplasmosis. VR2 polypeptides or polynucleotides and/or VR2 agonists or antagonists can be used to treat or detect any of these symptoms or diseases.

VR2 polynucleotides or polypeptides (including VR2 fragments, variants, derivatives, and analogs, and VR2 agonists and antagonists as described herein) can be used to differentiate, proliferate, and attract cells, leading to the regeneration of tissues. (See, *Science* 276:59–87 (1997). The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage. Tissues that may be regenerated using the present invention include organs (e.g., pancreas, liver, intestine, kidney, skin, endothelium), muscle (smooth, skeletal or cardiac), vascular (including vascular endothelium), nervous, hematopoietic, and skeletal (bone, cartilage, tendon, and ligament) tissue. Preferably, regeneration occurs without or decreased scarring. Regeneration also may include angiogenesis. Additionally, these compounds can be used to treat or prevent cell death (e.g., hematopoletic cell death) during processes of inflammation or tissue injury.

Moreover, VR2 polynucleotides or polypeptides (including VR2 fragments, variants, derivatives, and analogs, and VR2 agonists and antagonists as described herein) may increase regeneration of tissues difficult to heal. For example, increased tendon/ligament regeneration would quicken recovery time after damage. VR2 polynucleotides or polypeptides and/or VR2 agonists or antagonists of the present invention could also be used prophylactically in an effort to avoid damage. Specific diseases that could be treated include tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using VR2 polynucleotides or polypeptides and/or VR2 agonists or antagonists to proliferate and differentiate nerve cells. Diseases that could be treated using this method include central and peripheral nervous system diseases, neuropathies, or mechanical and traumatic disorders (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated using the VR2 polynucleotides or polypeptides and/or VR2 agonists or antagonists.

Given the activities modulated by VR2, it is readily apparent that a substantially altered (increased or decreased) level of expression of VR2 in an individual compared to the standard or "normal" level produces pathological conditions such as those described above. It will also be appreciated by one of ordinary skill that the VR2 agonists of the invention will exert modulating activities on any of its target cells. Therefore, it will be appreciated that conditions caused by a decrease in the standard or normal level of VR2 mediated activity in an individual, can be treated by administration of VR2 polypeptide or an agonist thereof.

Thus, in one embodiment, the present invention is directed to a method for enhancing (i.e., increasing) VR2 mediated activity (e.g., ion ($Ca^{+2}$) flux) which involves administering to an individual in need of an increased level of VR2 mediated activity, a therapeutically effective amount of VR2 polypeptide, fragment, variant, derivative, or analog, or an agonist capable of increasing VR2 mediated activity. In specific embodiments, VR2 mediated signaling is increased to treat a disease or condition wherein decreased cell survival, secretion, proliferation, migration, and/or differentiation is exhibited.

In another embodiment, the present invention is directed to a method for suppressing (i.e., decreasing) VR2 mediated activity (e.g., ion ($Ca^{+2}$) flux), which involves administering to an individual in need of a decreased level of VR2 mediated activity, a therapeutically effective amount of VR2 polypeptide, fragment, variant, derivative, or analog or an antagonist capable of decreasing VR2 mediated activity. In specific embodiments, VR2 mediated signaling is decreased to treat a disease or condition wherein increased cell survival, secretion, proliferation, migration and/or differentiation is exhibited.

In addition to treating diseases associated with elevated or decreased levels of VR2 mediated activity, the invention encompasses methods of administering VR2 agonists or antagonists to elevate or reduce VR2 mediated biological activity, respectively.

For example, any method which elevates VR2 concentration and/or activity can be used to stimulate hematopoiesis. Using these methods, the VR2 polypeptide and nucleotide sequences and VR2 agonists as described herein may be used to stimulate hematopoiesis. In a specific embodiment, VR2 polypeptides and polynucleotides and/or VR2 agonists are used in erythropoietin therapy, which is directed toward supplementing the oxygen carrying capacity of blood. VR2 treatment within the scope of the invention includes, but is not limited, to patients generally requiring blood transfusions, such as, for example, trauma victims, surgical patients, dialysis patients, and patients with a variety of blood composition-affecting disorders, such as hemophilia, cystic fibrosis, pregnancy, menstrual disorders, early anemia of prematurity, spinal cord injury, space flight, aging, various neoplastic disease states, and the like. Examples of patient conditions that require supplementation of the oxygen carrying capacity of blood and which are within the scope of this invention, include but are not limited to: treatment of blood disorders characterized by low or defective red blood cell production, anemia associated with chronic renal failure, stimulation of reticulocyte response, development of ferrokinetic effects (such as plasma iron turnover effects and marrow transit time effects), erythrocyte mass changes, stimulation of hemoglobin C synthesis, and increasing levels of hematocrit in vertebrates. The invention also provides for treatment to enhance the oxygen-carrying capacity of an individual, such as for example, an individual encountering hypoxic environmental conditions, The invention also encompasses combining the VR2 polypeptides and polynucleotides and/or VR2 agonists described herein with other proposed or conventional hematopoietic therapies. Thus, for example, VR2 agonists can be combined with compounds that singly exhibit erythropoietic stimulatory effects, such as erythropoietin, testosterone, progenitor cell stimulators, insulin-like growth factor, prostaglandins, serotonin, cyclic AMP, prolactin, and triiodothyzonine. Also encompassed are combinations with compounds generally used to treat aplastic anemia, such as methenolene, stanozolol, and nandrolone; to treat iron-deficiency anemia, such as iron preparations; to treat malignant anemia, such as vitamin B12 and/or folic acid; and to treat hemolytic anemia, such as adrenocortical steroids, e.g., corticoids. See e.g., Resegotti et al., *Panminerva Medica* 23:243–248 (1981); Kurtz, *FEBS Letters* 14a: 105–108 (1982); McGonigle et al., *Kidney Int*. 25:437–444 (1984); and Pavlovic-Kantera, *Expt. Hematol.*, 8(supp. 8):283–291 (1980).

Compounds that enhance the effects of or synergize with erythropoietin are also useful as adjuvants herein, and include but are not limited to, adrenergic agonists, thyroid hormones, androgens, hepatic erythropoietic factors, erythrotropins, and erythrogenins, See for e.g., Dunn, "Current Concepts in Erythropoiesis", John Wiley and Sons (Chichester, England, 1983); Weiland et al., *Blut*. 44:173–175 (1982); Kalmani, *Kidney int*. 22:383–391 (1982); Shahidi, *New Eng. J. Med*. 289:72–80 (1973); Urabe et al., *J. Exp. Med*. 149:1314–1325 (1979); Billat et al., *Expt. Hematol*. 10:133–140 (1982); Naughton et al., *Acta Haemat* 69:171–179 (1983); Cognote et al. in abstract 364, Proceedings 7th Intl. Cong. of Endocrinology (Quebec City, Quebec, July 1–7, 1984); and Rothman et al., *J. Surg. Oncol.* 20:105–108 (1982).

Methods for stimulating hematopoiesis comprise administering a hematopoietically effective amount (i.e, an amount which effects the formation of blood cells) of a pharmaceutical composition containing VR2 or a VR2 agonist to a patient. The VR2 or VR2 agonist is administered to the patient by any suitable technique, including but not limited to, parenteral, sublingual, topical, intrapulmonary and intranasal, and those techniques further discussed herein. The pharmaceutical composition optionally contains one or more members of the group consisting of erythropoietin, testosterone, progenitor cell stimulators, insulin-like growth factor, prostaglandins, serotonin, cyclic AMP, prolactin, triiodothyzonine, methenolene, stanozolol, and nandrolone, iron preparations, vitamin B12, folic acid and/or adrenocortical steroids. The VR2 or VR2 agonist and cotreatment drug(s) are suitably delivered by separate or by the same administration route, and at the same or at different times, depending, e.g., on dosing, the clinical condition of the patient, etc.

For treating abnormal conditions related to an under-expression of VR2 and its activity, or in which elevated or decreased levels of VR2 are desired, several approaches are available. One approach comprises administering to an individual in need of an increased level of VR2 mediated activity in the body, a therapeutically effective amount of an isolated VR2 polypeptide, fragment, variant, derivative or analog of the invention, or a compound which activates VR2, i.e., an agonist as described above, optionally in combination with a pharmaceutically acceptable carrier. Alternatively, gene therapy may be employed to effect the endogenous production of VR2 by the relevant cells in the subject. For example, a polynucleotide of the invention may be engineered for expression in a replication defective retroviral vector using techniques known in the art. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For an overview of gene therapy, see Chapter 20, Gene Therapy and other Molecular Genetic-based Therapeutic Approaches, (and references cited therein) in Human Molecular Genetics, T Strachan and A P Read, BIOS Scientific Publishers Ltd (1996).

Further, treatment can be administered, for example, in the form of gene replacement therapy. Specifically, one or more copies of a VR2 nucleotide sequence of the invention that directs the production of a VR2 gene product exhibiting normal function, may be inserted into the appropriate cells within a patient or animal subject, using vectors which include, but are not limited to, adenovirus, adeno-associated virus, retrovirus and herpesvirus vectors, in addition to other particles that introduce DNA into cells, such as liposomes and gene activated matrices. Because the VR2 gene is expressed in hematopoietic tissue, lymph, bone, peripheral blood leukocytes etc, such gene replacement techniques should be capable of delivering VR2 gene sequence to these cells within patients, or, alternatively, should involve direct administration of such VR2 polynucleotide sequences to the site of the cells in which the VR2 gene sequences are to be expressed. Alternatively, targeted homologous recombination can be utilized to correct the defective endogenous VR2 gene and/or regulatory sequences thereof (e.g., promoter and enhancer sequences), or alternatively, to "turn on" other dormant VR2 activity in the appropriate tissue or cell type.

Additional methods which may be utilized to increase the overall level of VR2 expression and/or VR2 activity include the introduction of appropriate VR2-expressing cells, preferably autologous cells, into a patient at positions and in numbers which are sufficient to ameliorate the symptoms of abnormalities in cell growth regulation, cell signaling, and other VR2 mediated activities. Such cells may be either recombinant or non-recombinant. Among the cells which can be administered to increase the overall level of VR2 gene expression in a patient are normal cells, which express the VR2 gene. Cell-based gene therapy techniques are well known to those skilled in the art, see, e.g., Anderson et al., U.S. Pat. No. 5,399,349; and Mulligan & Wilson, U.S. Pat. No. 5,460,959.

Thus, one embodiment of the invention comprises administering to in individual in need of an increased level of VR2 mediated activity compound that stimulates VR2 mediated activity (agonist), such as for example, an antibody or VR2 fragment, variant, derivative or analog of the invention, along with a pharmaceutically acceptable carrier in an amount effective to enhance (i.e., increase) VR2 mediated activity.

If the activity of VR2 is in excess, several approaches are available to reduce or inhibit VR2 activity using molecules derived from the polypeptide and polynucleotide sequences described above. Accordingly, a further aspect of the invention is related to a method for treating an individual in need of a decreased level of VR2 mediated activity in the body comprising, administering to such an individual a composition comprising a therapeutically effective amount of a VR2 polypeptide, fragment, variant, derivative or analog of the invention which acts as a VR2 antagonist or VR2 antagonist identified using the methods described herein, optionally, in combination with a pharmaceutically acceptable carrier. Preferably, VR2 activity is decreased to treat a disease wherein increased cell survival, secretion, proliferation, migration, and/or differentiation is exhibited. Polypeptides, derivatives, variants and analogs of the invention and other compounds which function as antagonists of VR2 can routinely be identified using the assays described infra and other techniques known in the art. Preferred antagonists for use in the present invention are VR2-specific antibodies.

In another approach, VR2 activity can be reduced or inhibited by decreasing the level of VR2 gene expression. In one embodiment, this is accomplished through the use of antisense sequences, either internally generated or separately administered (see, for example, O'Connor, *J. Neurochem.* 56:560 (1991) in Oligodeoxynucleotides as Antisense Inhibitors of Gene Expression, CRC Press, Boca Raton, Fla. (1988).) Antisense technology can be used to control gene expression through antisense DNA or RNA or through triple-helix formation. Antisense techniques are discussed, for example, in Okano, *J. Neurochem.* 56:560 (1991); *Oligodeoxynucleotides as Antisense Inhibitors of Gene Expression*, CRC Press, Boca Raton, Fla. (1988). Triple helix formation is discussed in, for instance, Lee et al., *Nucleic Acids Research* 6:3073 (1979); Cooney et al., *Science* 241:456 (1988); and Dervan et al., *Science* 251:1360 (1991). The methods are based on binding of a polynucleotide to a complementary DNA or RNA. For example, the 5' coding portion of a polynucleotide that encodes VR2 polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the VR2 polypeptide. The antisense RNA oligonucleotide hybridizes to the mRNA in vivo and blocks translation of the mRNA molecule into polypeptide.

In one embodiment, the VR2 antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the VR2 antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others know in the art, used for replication and expression in vertebrate cells. Expression of the sequence encoding VR2, or fragments thereof, can be by any promoter known in the art to act in vertebrate, preferably human cells. Such promoters can be inducible or constitutive. Such promoters include, but are not limited to, the SV40 early promoter region (Bernoist and Chambon, *Nature* 29:304–310 (1981), the promoter contained in the 3' long terminal repeat of Rous sarcoma virus (Yamamoto et al., *Cell* 22:787–797 (1980)), the herpes thymidine promoter (Wagner et al., *Proc. Natl. Acad. Sci. U.S.A.* 78:1441–1445

(1981)), the regulatory sequences of the metallothionein gene (Brinster et al., *Nature* 296:39–42 (1982)), etc.

The antisense nucleic acids of the invention comprise a sequence complementary to at least a portion of an RNA transcript of a VR2 gene. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded VR2 antisense nucleic acids, a single strand of the duplex DNA may thus be tested, or triplex formation may be assayed. The ability to hybridize will depend on both the degree of complementarity and the length of the antisense nucleic acid. Generally, the larger the hybridizing nucleic acid, the more base mismatches with a VR2 RNA it may contain and still form a stable duplex (or triplex as the case may be). One skilled in the art can ascertain a tolerable degree of mismatch by use of standard procedures to determine the melting point of the hybridized complex.

Potential VR2 antagonists according to the invention also include catalytic RNA, or a ribozyme (See, e.g., PCT International Publication WO 90/11364, published Oct. 4, 1990; Sarver et al., *Science* 247:1222–1225 (1990).) While ribozymes that cleave mRNA at site specific recognition sequences can be used to destroy VR2 mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, *Nature* 334:585–591 (1988). There are numerous potential hammerhead ribozyme cleavage sites within the nucleotide sequence of VR2 (FIGS. 1A–1D; SEQ ID NO:1). Preferably, the ribozyme is engineered so that the cleavage recognition site is located near the 5' end of the VR2 mRNA; i.e., to increase efficiency and minimize the intracellular accumulation of non-functional mRNA transcripts. DNA constructs encoding the ribozyme may be introduced into the cell in the same manner as described above for the introduction of antisense encoding DNA. Since ribozymes, unlike antisense molecules are catalytic, a lower intracellular concentration is required for efficiency.

Endogenous VR2 gene expression can also be reduced by inactivating or "knocking out" the VR2 gene or its promoter using targeted homologous recombination (e.g., see Smithies et al, *Nature* 317:330–234 (1985); Thomas et al., *Cell* 51:503–512 (1987); Thompson et al., *Cell* 5:313–321 (1989); each of which is incorporated by reference herein in its entirety). Such approach can be adapted for use in humans provided the recombinant DNA constructs are directly administered or targeted to the required site in vivo using appropriate viral vectors.

Alternatively, endogenous VR2 gene expression can be reduced by targeted deoxyribonucleotide sequences complementary to the regulatory region of the VR2 gene (i.e., the VR2 promoter and/or enhancers) to form triple helical structures that prevent transcription of the VR2 gene in target cells in the body, (see, generally, Helene et al., *Ann, N.Y. Acad. Sci*. 660:27–36 (1992); Helene, C., *Anticancer Drug Des*., 6(6):569–584 (1991); and Maher, L. J., *Bioassays* 14(12):807–815 (1992)). Thus, one embodiment of the invention comprises administering to an individual in need of a decreased level of VR2 mediated activity, a VR2 inhibitor compound (antagonist), such as for example, an antibody or VR2 fragment, variant, derivative or analog of the invention, along with a pharmaceutically acceptable carrier in an amount effective to suppress (i.e., lower) VR2 mediated activity.

Formulation and administration

It will be appreciated that conditions caused by a decrease in the standard or normal level of VR2 mediated activity in an individual, can be treated by administration of VR2 polypeptide or fragment, variant, derivative, or analog of the invention or an agonist thereof. Thus, the invention further provides a method of treating an individual in need of an increased level of VR2 mediated activity comprising administering to such an individual a pharmaceutical composition comprising an effective amount of an isolated VR2 polynucleotide or polypeptide; or fragment, variant, derivative, or analog of the invention, such as for example, the full length form of the VR2 encoding polynucleotide, effective to increase the VR2 mediated activity level in such an individual.

The dosage range required depends on the choice of peptide, the route of administration, the nature of the formulation, the nature of the subject's condition, and the judgment of the attending practitioner. As a general proposition, the total pharmaceutically effective amount of VR2 polypeptide administered parenterally per dose will be in the range of about 1 μμg/kg/day to 10 mg/kg/day of patient body weight, although, as noted above, this will be subject to therapeutic discretion. More preferably, this dose is at least 0.01 mg/kg/day, and most preferably for humans this dose is in the range of 0.1–100 mg/kg of subject, or between about 0.01 and 1 mg/kg/day. If given continuously, the VR2 polypeptide is typically administered at a dose rate of about 1 μg/kg/hour to about 50 μg/kg/hour, either by 1–4 injections per day or by continuous subcutaneous infusions, for example, using a mini-pump. An intravenous bag solution may also be employed. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Pharmaceutical compositions containing the VR2 polypeptides and polynucleotides of the invention (including fragments, variants, derivatives or analogs), and VR2 agonists and antagonists may be routinely formulated in combination with a pharmaceutically acceptable carrier. By "pharmaceutically acceptable carrier" is meant a non-toxic solid, semisolid or liquid filler, diluent, encapsulating material or formulation auxiliary of any type. In a specific embodiment, "pharmaceutically acceptable" means approved by a regulatory agency of the federal or a state government or listed in the U.S. Pharmacopeia or other generally recognized pharmacopeia for use in animals, and more particularly humans. Nonlimiting examples of suitable pharmaceutical carriers according to this embodiment are provided in "Remington's Pharmaceutical Sciences" by E. W. Martin, and include sterile liquids, such as water, saline, buffered saline, glycerol, ethanol, and oils, including those of petroleum, animal, vegetable or synthetic origin, such as peanut oil, soybean oil, mineral oil, sesame oil and the like. Formulation should suit the mode of administration, and is well within the skill of the art. For example, water is a preferred carrier when the pharmaceutical composition is administered intravenously. Saline solutions and aqueous dextrose and glycerol solutions can be employed as liquid carriers, particularly for injectable solutions. The invention additionally relates to pharmaceutical packs and kits comprising one or more containers filled with one or more of the ingredients of the aforementioned compositions of the invention.

Polypeptides and other compounds of the present invention may be administered alone or in conjunction with other compounds, such as therapeutic compounds. The pharmaceutical composition of the invention may be administered orally, rectally, parenterally, intracistemally, intravaginally, intraperitoneally, topically (as by powders, ointments, drops or transdermal patch), bucally, or as an oral or nasal spray. Preferred forms of systemic administration of the pharmaceutical compositions include parenteral injection, typically by intravenous injection. Other injection routes, such as subcutaneous, intramuscular, intrasternal, intraarticular or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

Gene Mapping

The nucleic acid molecules of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of a VR2 gene. This can be accomplished using a variety of well known techniques and libraries, which generally are available commercially. The genomic DNA then is used for in situ chromosome mapping using well known techniques for this purpose.

In addition, in some cases, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al., *Human Chromosomes: A Manual Of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance In Man*, available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

Having generally described the invention, the same will be more readily understood by reference to the following examples, which are provided by way of illustration and are not intended as limiting. Thus, the present invention is not to be limited in scope by the specific embodiments described herein, which are intended as single illustrations of individual aspects of the invention. Indeed, various modifications of the invention, in addition to those shown and described herein will become apparent to those skilled in the art from the foregoing description and accompanying drawings. Such modifications are intended to fall within the scope of the appended claims.

The entire disclosure of all publications (including patents, patent applications, journal articles, laboratory manuals, books, or other documents) cited herein are hereby incorporated by reference.

Further, the Sequence Listing submitted herewith in paper and computer readable form is herein incorporated by reference in their entireties.

EXAMPLES

Example 1

Isolation of the VR2 CDNA Clone From the Deposited Sample

The cDNA for VR2 is inserted into the EcoRI and Xho I multiple cloning site of UniZAP XR (Stratagene). UniZAP XR contains an ampicillin resistance gene and may be transformed into *E. coli* strain DH10B, available from Life Technologies. (See, for instance, Gruber, C. E., et al., *Focus* 15:59- (1993)).

Two approaches can be used to isolate VR2 from the deposited sample. First, a specific polynucleotide of SEQ ID NO:1 with 30–40 nucleotides is synthesized using an Applied Biosystems DNA synthesizer according to the sequence reported. The oligonucleotide is labeled, for instance, with $^{32}$P-g-ATP using T4 polynucleotide kinase and purified according to routine methods. (E.g., Maniatis et al, *Molecular Cloning: A Laboratory Manual*, Cold Spring Harbor Press, Cold Spring, N.Y. (1982)). The plasmid mixture is transformed into a suitable host (such as XL-1 Blue (Stratagene)) using techniques known to those of skill in the art, such as those provided by the vector supplier or in related publications or patents. The transformants are plated on 1.5% agar plates (containing the appropriate selection agent, e.g., ampicillin) to a density of about 150 transformants (colonies) per plate. These plates are screened using Nylon membranes according to routine methods for bacterial colony screening (e.g., Sambrook et al., *Molecular Cloning: A Laboratory Manual*, 2nd Edit., (1989), Cold Spring Harbor Laboratory Press, pages 1.93 to 1.104), or other techniques known to those of skill in the art.

Alternatively, two primers of 17–20 nucleotides derived from both ends of the SEQ ID NO:1 (i.e., within the region of SEQ ID NO:1 bounded by the 5' NT and the 3' NT of the clone) are synthesized and used to amplify the VR2 cDNA using the deposited cDNA plasmid as a template. The polymerase chain reaction is carried out under routine conditions, for instance, in 25 ul of reaction mixture with 0.5 ug of the above cDNA template. A convenient reaction mixture is 1.5–5 mM $MgCl_2$, 0.01% (w/v) gelatin, 20 uM each of dATP, dCTP, dGTP, dTTP, 25 pmol of each primer and 0.25 Unit of Taq polymerase. Thirty five cycles of PCR (denaturation at 94 degree C for 1 min; annealing at 55 degree C for 1 min; elongation at 72 degree C for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

Several methods are available for the identification of the 5' or 3' non-coding portions of the VR2 gene which may not be present in the deposited clone. These methods include but are not limited to, filter probing, clone enrichment using specific probes, and protocols similar or identical to 5' and 3' "RACE" protocols which are well known in the art. For instance, a method similar to 5' RACE is available for generating the missing 5' end of a desired full-length transcript. (Fromont-Racine et al., *Nucleic Acids Res.* 21(7):1683–1684 (1993)).

Briefly, a specific RNA oligonucleotide is ligated to the 5' ends of a population of RNA presumably containing full-length gene RNA transcripts. A primer set containing a primer specific to the ligated RNA oligonucleotide and a primer specific to a known sequence of the VR2 gene of interest is used to PCR amplify the 5' portion of the VR2 full-length gene. This amplified product may then be sequenced and used to generate the full length gene.

This above method starts with total RNA isolated from the desired source, although poly-A+RNA can be used. The RNA preparation can then be treated with phosphatase if necessary to eliminate 5' phosphate groups on degraded or damaged RNA which may interfere with the later RNA ligase step. The phosphatase should then be inactivated and the RNA treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase.

This modified RNA preparation is used as a template for first strand cDNA synthesis using a gene specific oligonucleotide. The first strand synthesis reaction is used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the VR2 gene.

Example 2
Isolation of VR2 Genomic Clones

A human genomic P1 library (Genomic Systems, Inc.) is screened by PCR using primers selected for the cDNA sequence corresponding to SEQ ID NO:1., according to the method described in Example 1. (See also, Sambrook.)

Example 3
Chromosomal Mapping of VR2

An oligonucleotide primer set is designed according to the sequence at the 5' end of SEQ ID NO:1. This primer preferably spans about 100 nucleotides. This primer set is then used in a polymerase chain reaction under the following set of conditions: 30 seconds, 95 degree C; 1 minute, 56 degree C; 1 minute, 70 degree C. This cycle is repeated 32 times followed by one 5 minute cycle at 70 degree C. Human, mouse, and hamster DNA is used as template in addition to a somatic cell hybrid panel containing individual chromosomes or chromosome fragments (Bios, Inc). The reactions is analyzed on either 8% polyacrylamide gels or 3.5% agarose gels. Chromosome mapping is determined by the presence of an approximately 100 bp PCR fragment in the particular somatic cell hybrid.

Example 4
Bacterial Expression of VR2

VR2 polynucleotide encoding a VR2 polypeptide of the invention is amplified using PCR oligonucleotide primers corresponding to the 5' and 3' ends of the DNA sequence, as outlined in Example 1, to synthesize insertion fragments. The primers used to amplify the cDNA insert should preferably contain restriction sites, such as BamHI and XbaI, at the 5' end of the primers in order to clone the amplified product into the expression vector. For example, BamHI and XbaI correspond to the restriction enzyme sites on the bacterial expression vector pQE-9. (Qiagen, Inc., Chatsworth, Calif.). This plasmid vector encodes antibiotic resistance ($Amp^r$, a bacterial origin of replication (ori), an IPTG-regulatable promoter/operator (P/O), a ribosome binding site (RBS), a 6-histidine tag (6-His), and restriction enzyme cloning sites.

Specifically, to clone the full-length VR2 polypeptide in a bacterial vector, the 5' primer has the sequence 5' GCAGCA <u>CATATG</u>GTCAGTCTC TGGTGGCTAGCCTGTCCTGA- CAG 3' (SEQ ID NO:4) containing the underlined NdeI restriction site followed by a number of nucleotides of the amino terminal coding sequence of the full-length VR2 sequence in SEQ ID NO:1. One of ordinary skill in the art would appreciate, of course, that the point in the protein coding sequence where the 5' primer begins may be varied to amplify a DNA segment encoding any desired portion of the complete VR2 protein shorter or longer than the full-length form of the protein. The 3' primer has the sequence 5'GCAGCA<u>GGTACCT</u>CAGTTGGACTGGAGG AGCTG GACGGGCACATAG 3' (SEQ ID NO:5) containing the underlined Asp718 restriction site followed by a number nucleotides complementary to the 3' end of the coding sequence of the VR2 DNA sequence of SEQ ID NO:1.

The pQE-9 vector is digested with NdeI and Asp718 and the amplified fragment is ligated into the pQE-9 vector maintaining the reading frame initiated at the bacterial RBS. The ligation mixture is then used to transform the *E. coli* strain M15/rep4 (Qiagen, Inc.) which contains multiple copies of the plasmid pREP4, which expresses the lacI repressor and also confers kanamycin resistance ($Kan^r$). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 ($O.D.^{600}$) of between 0.4 and 0.6. IPTG (Isopropyl-B-D-thiogalacto pyranoside) is then added to a final concentration of 1 mM. IPTG induces by inactivating the lacI repressor, clearing the P/O leading to increased gene expression.

Cells are grown for an extra 3 to 4 hours. Cells are then harvested by centrifugation (20 mins at 6000×g).

In addition to the above expression vector, the present invention further includes an expression vector comprising phage operator and promoter elements operatively linked to a VR2 polynucleotide, called pHE4a. (ATCC Accession Number 209645, deposited Feb. 25, 1998.) This vector contains: 1) a neomycinphosphotransferase gene as a selection marker, 2) an *E. coli* origin of replication, 3) a T5 phage promoter sequence, 4) two lac operator sequences, 5) a Shine-Delgarno sequence, and 6) the lactose operon repressor gene (lacIq). The origin of replication (oriC) is derived from pUC19 (LTI, Gaithersburg, Md.). The promoter sequence and operator sequences are made synthetically.

DNA can be inserted into the pHEa by restricting the vector with NdeI and KpnI, BamHII, XhoI, or Asp718, running the restricted product on a gel, and isolating the larger fragment (the stuffer fragment should be about 310 base pairs). The DNA insert is generated according to the PCR protocol described in Example 1, using PCR primers having restriction sites for NdeI (5' primer) and XbaI, BamHI, XhoI, or Asp718 (3' primer). The PCR insert is gel purified and restricted with compatible enzymes. The insert and vector are ligated according to standard protocols.

The engineered vector could easily be substituted in the above protocol to express protein in a bacterial system.

Example 5

Cloning and Expression of VR2 in a Baculovirus Expression System

In this example, the plasmid shuttle vector pA2 is used to insert VR2 polynucleotide into a baculovirus to express VR2. This expression vector contains the strong polyhedrin promoter of the *Autographa californica* nuclear polyhedrosis virus (AcMNPV) followed by convenient restriction sites such as BamHI, XbaI and Asp718. The polyadenylation site of the simian virus 40 ("SV40") is used for efficient polyadenylation. For easy selection of recombinant virus, the plasmid contains the beta-galactosidase gene from *E. coli* under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned VR2 polynucleotide.

Many other baculovirus vectors can be used in place of the vector above, such as pAc373, pVL941, and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., *Virology* 170:31–39 (1989).

Specifically, the VR2 cDNA sequence contained in the deposited clone, including the AUG initiation codon and any naturally associated leader sequence, is amplified using the PCR protocol described in Example 1. If the naturally occurring signal sequence is used to produce the secreted protein, the pA2 vector does not need a second signal peptide. Alternatively, the vector can be modified (pA2 GP) to include a baculovirus leader sequence, using the standard methods described in Summers et al., "A Manual of Methods for Baculovirus Vectors and Insect Cell Culture Procedures," Texas Agricultural Experimental Station Bulletin No. 1555 (1987).

More specifically, the cDNA sequence encoding the full length VR2 protein in the deposited clone, including the AUG initiation codon and the naturally associated leader sequence shown in SEQ ID NO:1, is amplified using PCR oligonucleotide primers corresponding to the 5' and 3' sequences of the gene. The 5' primer has the sequence 5 ' GCA GCA AGATCT GCC ATC ATG GTC AGT CTC TGG TGG CTA GCC TGT CCT GAC AG 3 ' (SEQ ID NO:6) containing the BglII restriction enzyme site, an efficient signal for initiation of translation in eukaryotic cells (Kozak, M., *J. Mol. Biol.* 196:947–950 (1987)), followed by a number of nucleotides of the sequence of the complete VR2 protein shown in FIGS. 1A–1D, beginning with the AUG initiation codon. The 3' primer has the sequence 5' GCA GCA TCTAGAT CAG TTG GAC TGG AGG AGC TGG ACG GGC ACA TAG 3' (SEQ ID NO:7) containing the XbaI restriction site followed by a number of nucleotides complementary to the 3 'noncoding sequence in FIGS. 1A–1D.

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.).

The fragment and the dephosphorylated plasmid are ligated together with T4 DNA ligase. *E. coli* HB 101 or other suitable *E. coli* hosts such as XL-1 Blue (Stratagene Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five ug of a plasmid containing the polynucleotide is co-transfected with 1.0 ug of a commercially available linearized baculovirus DNA ("BaculoGold™ baculovirus DNA", Pharmingen, San Diego, Calif.), using the lipofection method described by Felgner et al., *Proc. Natl. Acad. Sci. USA* 84:7413–7417 (1987). One ug of BaculoGold™ virus DNA and 5 ug of the plasmid are mixed in a sterile well of a microtiter plate containing 50 ul of serum-free Grace's medium (Life Technologies Inc., Gaithersburg, Md.). Afterwards, 10 ul Lipofectin plus 90 ul Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Graces medium without serum. The plate is then incubated for 5 hours at 27 degrees C. The transfection solution is then removed from the plate and 1 ml of Grace's insect medium supplemented with 10% fetal calf serum is added. Cultivation is then continued at 27 degrees C for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10.) After appropriate incubation, blue stained plaques are picked with the tip of a micropipettor (e.g., Eppendorf). The agar containing the recombinant viruses is then resuspended in a microcentrifuge tube containing 200 ul of Grace's medium and the suspension containing the recombinant baculovirus is used to infect Sf9 cells seeded in 35 mm dishes. Four days later the supernatants of these culture dishes are harvested and then they are stored at 4 degree C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 uCi of $^{35}$S-methionine and 5 uCi $^{35}$S-cysteine (available from Amersham) are added. The cells are further incubated for 16 hours and then are harvested by centrifugation. The proteins are analyzed by SDS-PAGE followed by autoradiography (if radiolabeled).

Microsequencing of the amino acid sequence of the amino terminus of purified protein may be used to determine the amino terminal sequence of the produced VR2 polypeptide.

Example 6
Expression of VR2 in Mammalian Cells

VR2 polypeptide can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (Pharmacia, Uppsala, Sweden), pRSVcat (ATCC 37152), pSV2DHFR (ATCC 37146), pBC12MI (ATCC 67109), pCMVSport 2.0, and pCMVSport 3.0. Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, VR2 polypeptide can be expressed in stable cell lines containing the VR2 polynucleotide integrated into a chromosome. The co-transfection with a selectable marker such as DHFR, gpt, neomycin, hygromycin allows the identification and isolation of the transfected cells.

The transfected VR2 gene can also be amplified to express large amounts of the encoded protein. The DHFR (dihydrofolate reductase) marker is useful in developing cell lines that carry several hundred or even several thousand copies of the gene of interest. (See, e.g., Alt, F. W., e al., *J. Biol. Chem.* 253:1357–1370 (1978); Hamlin, J. L. and Ma, C., *Biochem. et Biophys. Acta* 1097:107–143 (1990); Page, M. J. and Sydenham, M. A., *Biotechnology* 9:64–68 (1991)). Another useful selection marker is the enzyme glutamine synthase (GS) (Murphy et al., *Biochem J.* 227:277–279 (1991); Bebbington et al., *Bio/Technology* 10:169–175 (1992). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

Derivatives of the plasmid pSV2-DHFR (ATCC Accession No. 37146), the expression vectors pC4 (ATCC Accession No. 209646) and pC6 (ATCC Accession No.209647) contain the strong promoter (LTR) of the Rous Sarcoma Virus (Cullen et al., *Molecular and Cellular Biology*, 438–447 (March, 1985)) plus a fragment of the CMV-enhancer (Boshart et al., *Cell* 41:521–530 (1985)). Multiple cloning sites, e.g., with the restriction enzyme cleavage sites BamHI, XbaI and Asp718, facilitate the cloning of VR2. The vectors also contain the 3' intron, the polyadenylation and termination signal of the rat preproinsulin gene, and the mouse DHFR gene under control of the SV40 early promoter.

Specifically, the plasmid pC4 is digested with BamHI and XbaI and then dephosphorylated using calf intestinal phosphates by procedures known in the art. The vector is then isolated from a 1% agarose gel.

The cDNA sequence encoding the full length VR2 protein in the deposited clone is amplified using PCR oligonucleotide primers corresponding to the 5' and 3' sequences of the gene. The 5' primer has the sequence 5 ' GCA GCA <u>AGATCT</u> GCC ATC ATG GTC AGT CTC TGG TGG CTA GCC TGT CCT GAC AG 3' (SEQ ID NO:6) containing the BglII restriction enzyme site, an efficient signal for initiation of translation in eukaryotic cells (Kozak, M., *J. Mol. Biol.* 196:947–950 (1987)), followed by a number of nucleotides of the sequence of the complete VR2 protein shown in FIGS. 1A–1D, beginning with the AUG initiation codon. The 3' primer has the sequence 5' GCA GCA <u>TCTAGA</u> TCA GTT GGA CTG GAG GAG CTG GAC GGG CAC ATAG 3' (SEQ ID NO:7) containing the XbaI restriction site followed by a number of nucleotides complementary to the 3' non-coding sequence in FIGS. 1A–1D.

If a naturally occurring signal sequence is used to produce a secreted protein, the vector does not need a second signal peptide. Alternatively, if a naturally occurring signal sequence is not used, the vector can be modified to include a heterologous signal sequence in an effort to secrete the protein from the cell. (See, e.g., WO 96/34891.)

The amplified fragment is then digested with the BglII and XbaI and purified on a 1% agarose gel using a commercially available kit ("Geneclean," BIO 101 Inc., La Jolla, Calif.). The isolated fragment and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary cells lacking an active DHFR gene is used for transfection. Five μg of the expression plasmid pC4 is cotransfected with 0.5 ug of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 uM, 2 uM, 5 uM, 10 mM, 20 mM). The same procedure is repeated until clones are obtained which grow at a concentration of 100–200 uM.

Example 7
Construction of N-Terminal and/or C-Terminal Deletion Mutants

The following general approach may be used to clone a N-terminal or C-terminal deletion VR2 deletion mutant. Generally, two oligonucleotide primers of about 15–25 nucleotides are derived from the desired 5' and 3' positions of a polynucleotide of SEQ ID NO:1. The 5' and 3' positions of the primers are determined based on the desired VR2 polynucleotide fragment. An initiation and stop codon are added to the 5' and 3' primers respectively, if necessary, to express the VR2 polypeptide fragment encoded by the polynucleotide fragment. Preferred VR2 polynucleotide fragments are those encoding the N-terminal and C-terminal deletion mutants disclosed above in the "Polynucleotide and Polypeptide Fragments" section of the Specification.

Additional nucleotides containing restriction sites to facilitate cloning of the VR2 polynucleotide fragment in a desired vector may also be added to the 5' and 3' primer sequences. The VR2 polynucleotide fragment is amplified from genomic DNA or from the deposited cDNA clone using the appropriate PCR oligonucleotide primers and conditions discussed herein or known in the art. The VR2 polypeptide fragments encoded by the VR2 polynucleotide fragments of the present invention may be expressed and purified in the same general manner as the full length polypeptides, although routine modifications may be necessary due to the differences in chemical and physical properties between a particular fragment and full length polypeptide.

As a means of exemplifying but not limiting the present invention, the polynucleotide encoding the VR2 polypeptide fragment L-39 to N-889 is amplified and cloned as follows: A 5' primer is generated comprising a restriction enzyme site followed by an initiation codon in frame with the polynucleotide sequence encoding the N-terminal portion of the polypeptide fragment beginning with L-39. A complementary 3' primer is generated comprising a restriction enzyme site followed by a stop codon in frame with the polynucleotide sequence encoding C-terminal portion of the VR2 polypeptide fragment ending with N-889.

The amplified polynucleotide fragment and the expression vector are digested with restriction enzymes which recognize the sites in the primers. The digested polynucleotides are then ligated together. The VR2 polynucleotide fragment is inserted into the restricted expression vector, preferably in a manner which places the VR2 polypeptide fragment coding region downstream from the promoter. The ligation mixture is transformed into competent *E. coli* cells using standard procedures and as described in the Examples herein. Plasmid DNA is isolated from resistant colonies and the identity of the cloned DNA confirmed by restriction analysis, PCR and DNA sequencing.

Example 8
Protein Fusions of VR2

VR2 polypeptides are preferably fused to other proteins. These fusion proteins can be used for a variety of applications. For example, fusion of VR2 polypeptides to His-tag, HA-tag, protein A, IgG domains, and maltose binding protein facilitates purification. (See Example 5; see also EP A 394,827; Traunecker, et al., Nature 331:84–86 (1988)). Similarly, fusion to IgG-1, IgG-3, and albumin increases the halflife time in vivo. Nuclear localization signals fused to VR2 polypeptides can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector.

For example, if pC4 (Accession No. 209646) is used, the human Fc portion can be ligated into the BamHI cloning site. Note that the 3' BamHI site should be destroyed. Next, the vector containing the human Fc portion is re-restricted with BamHI, linearizing the vector, and VR2 polynucleotide, isolated by the PCR protocol described in Example 1, is ligated into this BamHI site. Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891.)

Human IgG Fc region:
GGGATCCGGAGCCCAAATCTTCTGA-
CAAAACTCACACATGCCCACC GTGCCCAGCACCT-
GAATTCGAGGGTGCACCGTCAGTCTTCCTCTTCC
CCCCAAAACCCAAGGACACCCTCAT-
GATCTCCCGGACTCCTGAGGT CACATGCGTGGTG-
GTGGACGTAAGCCACGAAGACCCTGAGGTCAAG
TTCAACTGGTACGTGGACGGCGTGGAG-
GTGCATAATGCCAAGACAA AGCCGCGGGAGGAG-
CAGTACAACAGCACGTACCGTGTGGTCAGCGT
CCTCACCGTCCTGCACCAGGACTGGCT-
GAATGGCAAGGAGTACAAG TGCAAGGTCTCCAA-
CAAAGCCCTCCCAACCCCCATCGAGAAAACCA
TCTCCAAAGCCAAAGGGCAGC-
CCCGAGAACCACAGGTGTACACCCT GCCCCCATC-
CCGGGATGAGCTGACCAAGAACCAGGT-
CAGCCTGACC
TGCCTGGTCAAAGGCTTCTATCCAAGC-
GACATCGCCGTGGAGTGGG AGAGCAATGGGCAGC-
CGGAGAACAACTACAAGACCACGCCTCCCGT
GCTGGACTCCGACGGCTCCTTCTTCCTC-
TACAGCAAGCTCACCGTGG ACAAGAGCAGGTG-
GCAGCAGGGGAACGTCTTCTCATGCTCCGTGAT
GCATGAGGCTCTGCACAACCACTACACG-
CAGAAGAGCCTCTCCCTG TCTCCGGGTAAAT-
GAGTGCGACGGCCGCGACTCTAGAGGAT (SEQ ID NO:8)

Example 9
Production of an Antibody

The antibodies of the present invention can be prepared by a variety of methods. (See, Current Protocols, Chapter 2.) For example, cells expressing VR2 is administered to an animal to induce the production of sera containing polyclonal antibodies. In a preferred method, a preparation of VR2 protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or protein binding fragments thereof). Such monoclonal antibodies can be prepared using hybridoma technology. (Köhler et al., *Nature* 256:495 (1975); Köhler et al., *Eur. J. Immunol.* 6:511 (1976); Köhler et al., *Eur. J. Immunol.* 6:292 (1976); Hammerling et al., in: *Monoclonal Antibodies and T-Cell Hybridomas*, Elsevier, N.Y., pp. 563–681 (1981)). In general, such procedures involve immunizing an animal (preferably a mouse) with VR2 polypeptide or, more preferably, with a secreted VR2 polypeptide-expressing cell. Such cells may be cultured in any suitable tissue culture medium; however, it is preferable to culture cells in Earle's modified Eagle's medium supplemented with 10% fetal bovine serum (inactivated at about 56 degree C), and supplemented with about 10 g/l of nonessential amino acids, about 1,000 U/ml of penicillin, and about 100 ug/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2O), available from the ATCC. After fusion, the resulting hybridoma cells are selectively maintained in HAT medium, and then cloned by limiting dilution as described by Wands et al., *Gastroenterology* 80:225–232 (1981)). The hybridoma cells obtained through such a selection are then assayed to identify clones which secrete antibodies capable of binding the VR2 polypeptide.

Alternatively, additional antibodies capable of binding to VR2 polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the VR2 specific antibody can be blocked by VR2 Such antibodies comprise anti-idiotypic antibodies to the VR2 specific antibody and can be used to immunize an animal to induce formation of further VR2 specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, secreted VR2 protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. (See, for review, Morrison, *Science* 229:1202(1985); Oi et al., *BioTechniques* 4:214 (1986); Cabilly et al., U.S. Pat. No. 4,816,567; Taniguchi et al. EP 171496; Morrison et al., EP 173494, Neuberger et al, WO 8601533; Robinson et al., WO 8702671; Boulianne et al., *Nature* 312:643 (1984); Neuberger et al., *Nature* 314:268 (1985)).

Example 10

Method of Detecting Abnormal Levels of VR2 in a Biological Sample

VR2 polypeptides can be detected in a biological sample, and if an increased or decreased level of VR2 is detected, this polypeptide is a marker for a particular phenotype. Methods of detection are numerous, and thus, it is understood that one skilled in the art can modify the following assay to fit their particular needs.

For example, antibody-sandwich ELISAs are used to detect VR2 in a sample, preferably a biological sample. Wells of a microtiter plate are coated with specific antibodies to VR2 at a final concentration of 0.2 to 10 ug/ml. The antibodies are either monoclonal or polyclonal and are produced by the method described in Example 11. The wells are blocked so that non-specific binding of VR2 to the well is reduced.

The coated wells are then incubated for >2 hours at RT with a sample containing VR2. Preferably, serial dilutions of the sample should be used to validate results. The plates are then washed three times with deionized or distilled water to remove unbounded VR2.

Next, 50 ul of specific antibody-alkaline phosphatase conjugate, at a concentration of 25–400 ng, is added and incubated for 2 hours at room temperature. The plates are again washed three times with deionized or distilled water to remove unbounded conjugate.

Add 75 ul of 4-methylumbelliferyl phosphate (MUP) or p-nitrophenyl phosphate (NPP) substrate solution to each well and incubate I hour at room temperature. Measure the reaction by a microtiter plate reader. Prepare a standard curve, using serial dilutions of a control sample, and plot VR2 polypeptide concentration on the X-axis (log scale) and fluorescence or absorbance of the Y-axis (linear scale). Interpolate the concentration of the VR2 in the sample using the standard curve.

Example 11

Formulating a Polypeptide

The VR2 composition will be formulated and dosed in a fashion consistent with good medical practice, taking into account the clinical condition of the individual patient (especially the side effects of treatment with the VR2 polypeptide alone), the site of delivery, the method of administration, the scheduling of administration, and other factors known to practitioners. The "effective amount" for purposes herein is thus determined by such considerations.

As a general proposition, the total pharmaceutically effective amount of VR2 administered parenterally per dose will be in the range of about 1 ug/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, VR2 is typically administered at a dose rate of about 1 ug/kg/hour to about 50 ug/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing VR2 are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

VR2 is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman, U., et al., *Biopolymers* 22:547–556 (1983)), poly (2- hydroxyethyl methacrylate) (Langer, R., et al., *J. Biomed. Mater. Res.* 15:167–277 (1981), and Langer, R., *Chem. Tech.* 12:98–105 (1982)), ethylene vinyl acetate (Langer, R., et al.) or poly-D-(–)-3-hydroxybutyric acid (EP 133,988). Sustained-release compositions also include liposomally entrapped VR2 polypeptides. Liposomes containing the VR2 are prepared by methods known per se: DE 3,218,121; Epstein et al., *Proc. Natl. Acad. Sci. USA* 82:3688–3692 (1985); Hwang et al., *Proc. Natl. Acad. Sci. USA* 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal secreted polypeptide therapy.

For parenteral administration, in one embodiment, VR2 is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting VR2 uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

VR2 is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of polypeptide salts.

VR2 used for therapeutic administration can be sterile. Sterility is readily accomplished by filtration through sterile filtration membranes (e.g., 0.2 micron membranes). Therapeutic polypeptide compositions generally are placed into a container having a sterile access port, for example, an intravenous solution bag or vial having a stopper pierceable by a hypodermic injection needle.

VR2 polypeptides ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous VR2 polypeptide solution, and the resulting mixture is lyophilized. The infusion solution is prepared by reconstituting the lyophilized VR2 polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, VR2 may be employed in conjunction with other therapeutic compounds.

Example 12

Method of Treatment Using Gene Therapy—in vivo

Another aspect of the present invention is using in vivo gene therapy methods to treat disorders, diseases and conditions. The gene therapy method relates to the introduction of naked nucleic acid (DNA, RNA, and antisense DNA or RNA) VR2 sequences into an animal to increase or decrease the expression of the VR2 polypeptide. The VR2 polynucleotide may be operatively linked to a promoter or any other genetic elements necessary for the expression of the VR2 polypeptide by the target tissue. Such gene therapy and delivery techniques and methods are known in the art, see, for example, WO90/11092, WO98/11779; U.S. Pat. Nos. 5,693,622, 5,705,151, 5,580,859; Tabata H., et al., *Cardiovasc. Res.* 35(3):470–479 (1997), Chao, J., et al., *Pharmacol. Res.* 35(6):517–522 (1997), Wolff, J. A., *Neuromuscul. Disord.* 7(5):314–318 (1997), Schwartz, B., et al., *Gene Ther.* 3(5):405–411 (1996), Tsurumi, Y., et al., *Circulation* 94(12):3281–3290 (1996) (incorporated herein by reference).

The VR2 polynucleotide constructs may be delivered by any method that delivers injectable materials to the cells of an animal, such as, injection into the interstitial space of tissues (heart, muscle, skin, lung, liver, intestine and the like). The VR2 polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the VR2 polynucleotides may also be delivered in liposome formulations (such as those taught in Felgner, P. L., et al., *Ann. NY Acad. Sci.* 772:126–139 (1995) and Abdallah, B., et at, *Biol. Cell* 85(1):1–7) (1995) which can be prepared by methods well known to those skilled in the art.

The VR2 polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The VR2 polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked VR2 polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked VR2 polynucleotide constructs can be delivered to arteries during angioplasty by the catheter used in the procedure.

The dose response effects of injected VR2 polynucleotide in muscle in vivo is determined as follows. Suitable VR2 template DNA for production of mRNA coding for VR2 polypeptide is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The VR2 template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for VR2 protein expression. A time course for VR2 protein expression may be done in a similar fashion except that quadriceps from different mice are harvested at different times. Persistence of VR2 DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using VR2 naked DNA.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference.

Moreover, the sequence submitted herewith in paper and computer readable form are herein incorporated by reference in their entireties.

What is claimed is:

1. An isolated polynucleotide comprising a nucleic acid selected from the group consisting of:
   (a) a nucleic acid encoding amino acids 1 to 889 of SEQ ID NO:2;
   (b) a nucleic acid encoding amino acids 2 to 889 of SEQ ID NO:2; and
   (c) a nucleic acid encoding the complete amino acid sequence encoded by the cDNA clone contained in ATCC Deposit No. 203082;
      wherein said nucleic acid encodes a protein which mediates intracellular Ca+2 flux in response to thermal stimuli.

2. The isolated polynucleotide of claim 1, wherein said nucleic acid is (a).

3. The isolated polynucleotide of claim 1, wherein said nucleic acid is (b).

4. The isolated polynucleotide of claim 1, wherein said nucleic acid is (c).

5. The isolated polynucleotide of claim 1, further comprising a heterologous polynucleotide.

6. A method of producing a vector comprising inserting the isolated polynucleotide of claim 1, into a vector.

7. A vector comprising the isolated polynucleotide of claim 1.

8. The vector of claim 7, wherein said isolated polynucleotide is operably associated with a heterologous regulatory sequence.

9. A host cell comprising the isolated polynucleotide of claim 1.

10. The host cell of claim 9, wherein said isolated polynucleotide is operably associated with a heterologous regulatory sequence.

11. A method of producing a polypeptide comprising culturing the host cell of claim 10, under conditions such that a polypeptide is expressed, and recovering said polypeptide.

12. A composition comprising the isolated polynucleotide of claim 1 and a pharmaceutically acceptable carrier.

13. An isolated polynucleotide comprising a nucleic acid encoding a first amino acid sequence at least 95% identical to a reference amino acid sequence selected from the group consisting of:
   (a) amino acids 1 to 889 of SEQ ID NO:2;
   (b) amino acids 2 to 889 of SEQ ID NO:2;
   (c) the complete amino acid sequence encoded by the cDNA clone contained in ATCC Deposit No. 203082;
      wherein said nucleic acid encodes a protein which mediates intracellular Ca+2 flux in response to thermal stimuli.

14. The isolated polynucleotide of claim 13, wherein said reference amino acid sequence is (a).

15. The isolated polynucleotide of claim 13, wherein said reference amino acid sequence is (b).

16. The isolated polynucleotide of claim 13, wherein said reference amino acid sequence is (c).

17. The isolated polynucleotide of claim 13, further comprising a heterologous polynucleotide.

18. A method of producing a vector comprising inserting the isolated polynucleotide of claim 13 into a vector.

19. A vector comprising the isolated polynucleotide of claim 13.

20. The vector of claim 19, wherein said isolated polynucleotide is operably associated with a heterologous regulatory sequence.

21. A host cell comprising the isolated polynucleotide of claim 13.

22. The host cell of claim 21, wherein said isolated polynucleotide is operably associated with a heterologous regulatory sequence.

23. A method of producing a polypeptide comprising culturing the host cell of claim 22 under conditions such that a polypeptide is expressed, and recovering said polypeptide.

24. A composition comprising the isolated polynucleotide of claim 13 and a pharmaceutically acceptable carrier.

25. An isolated polynucleotide comprising a first nucleic acid which hybridizes in a wash solution consisting of 0.1×SSC at 65° C., to a second nucleic acid selected from the group consisting of:
   (a) a nucleic acid consisting of the coding region of the cDNA clone contained in ATCC Deposit No. 203082 or the complement thereof; and
   (b) a nucleic acid consisting of the coding region of SEQ ID NO:1 or the complement thereof;
      wherein said first nucleic acid is 150 or more nucleotides long and said first nucleic acid does not comprise any one of SEQ ID NOs:18–67; and
      wherein said first nucleic acid encodes a protein which mediates intracellular Ca+2 flux in response to thermal stimuli.

26. The isolated polynucleotide of claim 25, further comprising a heterologous polynucleotide.

27. A method of producing a vector comprising inserting the isolated polynucleotide of claim 25 into a vector.

28. A vector comprising the isolated polynucleotide of claim 25.

29. The vector of claim 28, wherein said isolated polynucleotide is operably associated with a heterologous regulatory sequence.

30. A host cell comprising the isolated polynucleotide of claim 25.

31. The host cell of claim herein said isolated polynucleotide is operably associated with a heterologous regulatory sequence.

32. A method of producing a polypeptide comprising culturing the host cell of claim under conditions such that a polypeptide is expressed, and recovering said polypeptide.

33. A composition comprising the isolated polynucleotide of claim 25 and a pharmaceutically acceptable carrier.

* * * * *

UNITED STATES PATENT AND TRADEMARK OFFICE
CERTIFICATE OF CORRECTION

PATENT NO. : 6,444,440 B1
DATED : September 3, 2002
INVENTOR(S) : Paul E. Young and Steven M. Ruben It is certified that error appears in the above-identified patent and that said Letters Patent is hereby corrected as shown below:

Title page,
Item [67] and [63], Related U.S. Application Data, please delete the priority claim to both PCT/US98/04493 and United States Provisional Application No. 60/040,163.

Column 1,
Lines 3-7, please delete the priority claim.

Column 5,
Line 9, please replace "263052" with -- 203082 --.

Column 134,
Line 56, please replace "herein" with -- 30, wherein --;
Line 60, please insert -- 31 -- after the word "claim."

Signed and Sealed this

Eleventh Day of March, 2003

JAMES E. ROGAN
*Director of the United States Patent and Trademark Office*